Figure 1A:
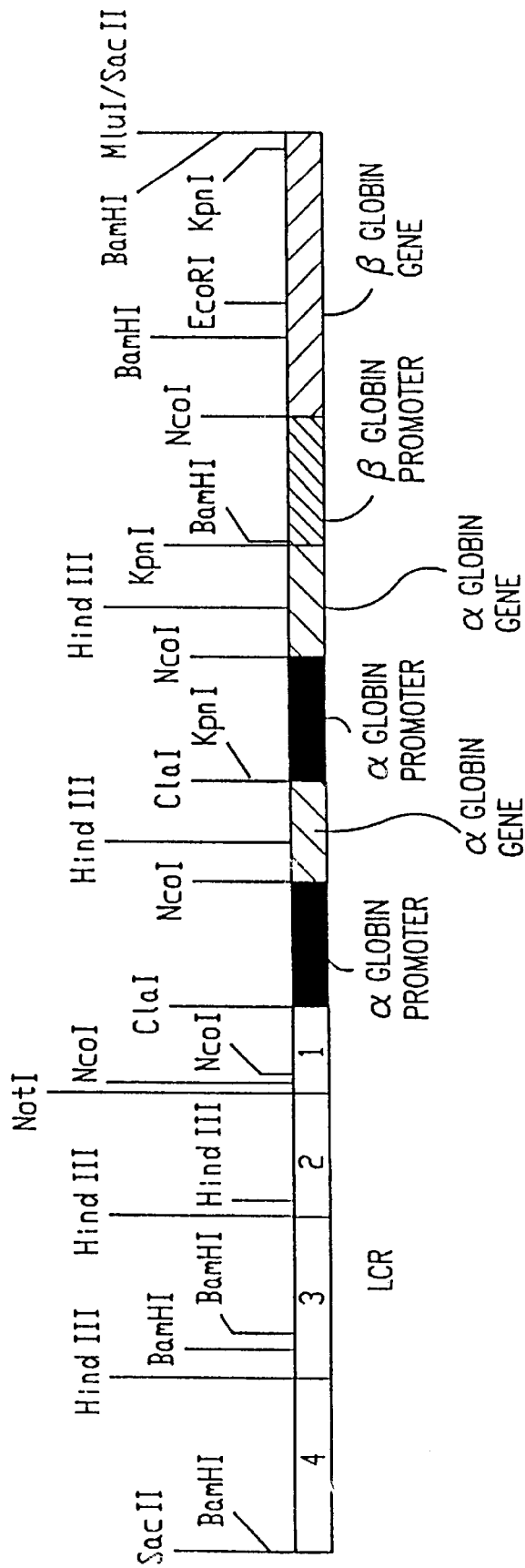

US005922854A

United States Patent [19]
Kumar et al.

[11] Patent Number: 5,922,854
[45] Date of Patent: Jul. 13, 1999

[54] PURIFYING HUMAN HEMOGLOBLIN FROM TRANSGENIC PIG RED CELLS AND PLASMIDS CONTAINING PIG GLOBIN NUCLEIC ACIDS

[76] Inventors: Ramesh Kumar, 60 Yard Rd., Pennington, N.J. 08534; Ajay Sharma, 24 Feiler Ct., Lawrenceville, N.J. 08648; Clara Paulhiac, 22 Madison St., Princeton, N.J. 08542; Anastasia P. Khoury-Christianson, 622 S. 21st St., Philadelphia, Pa. 19146; Sunita Midha, 30 Jeffrey Ct., Dayton, N.J. 08810

[21] Appl. No.: 08/105,989

[22] Filed: Aug. 11, 1993

Related U.S. Application Data

[63] Continuation-in-part of application No. 08/030,897, Mar. 15, 1993, abandoned, which is a continuation-in-part of application No. 07/897,648, Jun. 12, 1992, abandoned, which is a continuation-in-part of application No. 07/717,774, Jun. 14, 1991, abandoned.

[51] Int. Cl.$^6$ ............................. C07H 21/04; C07K 1/00; C07K 14/00; A61K 35/14
[52] U.S. Cl. ...................... 536/23.5; 536/24.1; 530/385; 530/416; 514/21
[58] Field of Search .............................. 800/2; 530/416; 435/320.1

[56] References Cited

U.S. PATENT DOCUMENTS

| 5,028,588 | 7/1991 | Hoffman et al. | 514/6 |
| 5,602,306 | 2/1997 | Townes et al. | |

FOREIGN PATENT DOCUMENTS

| WO 89/01517 | 2/1989 | WIPO . |
| WO 91/05041 | 4/1991 | WIPO . |

OTHER PUBLICATIONS

Wilmut et al (1982) Nature 300, 611–615.
Ishimoro et al (1989) J. Biol. Chem. 264, 14624–14626.
Constantoulakis et al., 1991, "Locus Control Region–Aγ Transgenic Mice: A New Model for udying the Induction of Fetal Hemoglobin in the Adult", *Blood* 77: 1326–1333.
Rubin et al., 1991, "Hypoxia–induced In Vivo Sickling of Transgenic Mouse Red Cells", *J. Clin. Invest.* 87: 639–647.
Ryan et al., 1990, "Human Sickle Hemoglobin in Transgenic Mice", *Science* 247: 566–568.
Tanaka et al., 1990, "Expression of Human Globin Genes in Transgenic Mice Carrying the β–Globin Gene Cluster with a Mutation Causing $^G\gamma\beta^+$Hereditary Persistence of Fetal Hemoglobin$^{a"}$", *Ann. New York Acad. Sci.* 612: 167–178.
Raich et al., 1990, Autonomous Developmental Control of Human Embryonic Globin Gene Switching in Transgenic Mice, *Science* 250:1147–1149.
Greaves et al., 1990, "A transgenic mouse model of sickle cell disorder", *Nature* 343: 183–185.
Townes et al., 1989, "Hemoglobin Switching Part A: Transcriptional Regulation", Alan R. Liss, Inc., pp. 47–61.
Behringer et al., 1989, "Synthesis of Functional Human Hemoglobin in Transgenic Mice", *Science* 245: 971–973.

Hanscombe, 1989, "High–Level, erythroid–specific expression of the human α–globin gene in transgenic mice and the production of human hemoglobin in murine erythrocytes", *Genes and Development* 3: 1572–1581.
Kutlar et al., 1989, Quantitation of Hemoglobins Bart's, H. Portland–I, Portland–II and Constant Spring by Anion–Exchange High–Performance Liquid Chromatography,*Journal of Chromatography* 487: 265–274.
Enver et al., 1989, "The human β–globin locus activation region alters the developmental fate of a human fetal globin gene in transgenic mice", *Proc. Natl. Acad. Sci. USA* 86: 7033–7037.
Christensen et al., 1988, Preparation of human hemoglobin $A_o$ for possible use as a blood substitute, *Journal of Biochemical and Biophysical Methods* 17: 143–154.
Rubin et al., 1988, "Introduction and Expression of the Human B$^s$–Globin Gene in Transgenic Mice", *Am. J. Hum. Genet.* 42: 585–591.
Evelo et al., 1988, "Separation of human haemoglobin alkylated at β93 cysteine from its native form by fast protein liquid chromatography", *Journal of Chromatography* 427: 335–340.
Gelfi et al., 1987, "Purification of human hemoglobin valence intermediates by preparative immobilized pH gradients", *Journal of Biochemical and Biophysical Methods* 14: 139–147.
Kollias et al., 1986, "Regulated Expression of Human $^{A\gamma}$–, β–, and Hybrid γβ–Globin Genes in Transgenic Mice: Manipulation of the Developmental Expression Patterns", *Cell* 46: 89–94.
Burke et al., 1986, "Rapid Cation–Exchange Chromatography of Hemoglobins and Other Proteins", *Journal of Chromatography* 359: 533–540.
Magram et al., 1985, Developmental regulation of a cloned adult β–globin gene in transgenic mice, *Nature* 315: 338–340.
Hammer et al., 1985, "Production of Transgenic Rabbits, sheep and pigs by microinjection", *Nature* 315: 680–683.
Anderson et al., 1985, "Attempts at Gene Therapy in β–Thalassemic Mice", *Ann. New York Acad. Sci.* 445: 445–451.
Wright et al., 1984, "DNA Sequences Required for Regulated Expression of β–Globin Genes in Murine Erythroleukemia Cells", *Cell* 38: 265–273.
Bucci, 1981, "Preparation of Isolated Chains of Human Hemoglobin", as found in *Methods in Enzymology vol. 76 Hemoglobins* (Academic Press, New York) pp. 97–125.

(List continued on next page.)

*Primary Examiner*—Deborah Crouch
*Attorney, Agent, or Firm*—Janice Guthrie

[57] ABSTRACT

The present invention relates to the use of transgenic pigs for the production of human hemoglobin. The transgenic pigs of the invention may be used as an efficient and economical source of cell-free human hemoglobin that may be used for transfusions and other medical applications in humans. Also disclosed are the methods of purifying human hemoglobin from pig red cell lysate, and plasmids contained pig and human nucleic acid sequences for the production of transgenic pigs expressing human globin DNA sequences.

10 Claims, 75 Drawing Sheets

OTHER PUBLICATIONS

Proudfoot and Baralle, 1979, "Molecular cloning of human ε–globin gene", *Proc. Natl. Acad. Sci. USA* 76: 5435–5439.
Kappel et al (1992) Current Opinion in Biotech. 3, 548–553.
Behringer et al (1989) Science 245, 971–973.
Hammer et al (1985) Nature 315, 680–683.
Riggs (1981) Meth. Enz. 76, 5–29.
Woo–Pen et al (1985) J. Chromatog. 318, 325–332.
Immamura et al (1969) J. Clin. Invest. 48, 2341–2348.
Schnee et al (1990) Human Genetics 84, 365–367.
Marinucci et al (1981) BBA 668, 209–215.

```
         10         20         30         40         50         60
CCCCAGCCCT TTTTCCAGGT CAGCGCAGGG AAAAAACATG TTCTCTGTCC CTGGTTATAC 70         80         90        100        110        120
TGTTTAGAAA CATCACCTCC CTCGGCGAAA CTAAAACTTG GGGGTTGCAA TTTATTCCTT 130        140        150        160        170        180
GCTTCTTTGT ATTTCGTACC ACATTGAGAG AGCTCTAGGT TTTCATCCGC AGATTCCCAA 190        200        210        220        230        240
ACCTTCGCAG AGGAGCTGTT TCACAGGACC GTGATTCAAG TTTACTCTAC TTTTCCATCA 250        260        270        280        290        300
TTTATTTGGT CATATGTTTA AATGAAGAAA GAAAGGAATG AAGATACCTG AATGAAATGA 310        320        330        340        350        360
GTATTTGTTT TCTTACCAGC AGGACTGAAT ACAAATGAAG AGAAGAAAAA TACGCACATT 370        380        390        400        410        420
TAGGACTTGG GCAGAGGTTT TATCCACGCT CTCCTTGTGG TTATTTCCCA TATTCAGAAG 430        440        450        460        470        480
GCGCGGGTGT GGATTCGTCT GTATGGTCCT AAATTGAACC ACAGTGGTCA AATCCCTCCA
```

FIG. 8

```
         490        500        510        520        530        540
CTTTCTGCTC CTTGGATTCT TCGTTTGTGT ACTAAGAAAA TGGGGAGGCA GTCTCTAAGA 550        560        570        580        590        600
GATTGCTACA GTGGGACTCA ACTCTAAAAG TTGTACAGAC TTGCTAAGGA GGATGAAATT 610        620        630        640        650        660
AGTAGCACTT TGCACTGTGA GGATGGACCT AGAGCTCCCC AGAGAAGGGC TGAAGGTCTG 670        680        690        700        710        720
AAGTTGGTGC CAGGAACGTC TCGAAGACAG GTATACTGTC AACATTCAAG CCTCACCCTG 730        740        750        760        770        780
TGGAACCACG CCCTGGCCTG GGCCAATCTG CTCCCAGAAG CAGGGAGGGC AGGAGGCTGG 790        800        810            820        830        840
GGGGGCATAA AAGGAAGAGC AGAGCCAGCA GCCACCTACA TTTGCTTCTG ACACAACCGT 850        860        870        880
GTTCACTAGC AACTGCACAA ACAGACAACA TGGTGCATCT GTCTGCTGA
```

FIG. 8 (cont.)

```
  1    CCCCAGCCCCTTTTCCAGTCAGGCGCAGGGAAAAACATGTTCTCTGTCCCTGGTTATAC
1287    CCCCAGACACTCTTGCAGATTAGTCCAGGCCAGAAA CA GTTAGATGTCCCCAGTTAACC
        ****  *     **  *    * *  *   *         *   ***   *  **  **

61    TG T TTAGAAACATCACCTC CCTCGGCGAAACTAAAACTTGGGGGTTGCAATTTATTC
1345    TCCTATTTGACACCACTGATTACCCCATTGATAGTCACACTTTGGG TTGTAAGTGACTT
       **  *      **  ** ***  ***  *  *  * *           *** **  ***

118    CTTGCTTCTTTGTATTTCGTACCACATTGAGAGAGCTCTAGTTTTCATCCGCAGATTCC
1404    TTTATTTATTTGTATTTGACTGCATTAAGAGGTCTCTAGTTTTTTATCCTTGTTTCC
       * **   ********     **  *** *** ****** **** **  *  ****

178    CAAACCTTCGCAGAGGAGCTGTTTCACAG G ACCGTGATTCAAGTTTACTCTACTTTTC
1464    CAAAACCTAATA AGTAACTAATGCACAGAGCACACATTGATTGTATTTATTCTATTTTA
       ****  * **        *  ** * *                    *       *

236    CATCATTTATTTGGTCATATGTTTAAATGAAGAAA         270
1523    GACATAATTTATTAGCATGCATGAGCAAATTAAGAAA      12883
       ** *    * ******  *   *  *** **   ***

Matches = 176    Length = 277    Matches/Length = 63.5 percent

302    TATTTGTTTTCTTACCAGCAGGACTGAATACAAATGAAGAGAAGAAAAA TACGCAC A
1629    TTTTCTTTCTTTTCTTACCAGAAGGTTTAATCCAAATAAGGAGAAGATATGCTTAGAACTGA
       * *    *  *          *    *      *    *** *** **

359    TTTAGGACTTGGGCAGAGGTTTTATCCGCTCTCCTTGTGTTATTCCATATTCAGA
1689    GGTAG AGTTTT CATCCATTCTGTCCTGTAAGTATTT TGCATATTCTGGAGACGCAGG
        **  *     *   ***  ***   *  *   *        ****  ** **

419    AGGCGCGGG TGTGGAT TCGT          CTGTATGGTCCTAAATTGAAC CACAGTGGTCAA
1746    AAGAGATCCATCCATCTACATATCCCAAAGCTGTAGGACAAGCTCTTCCACTTTTA
       *  *  *  *     **    **          ******* *     *********  **
```

```
472   ATCCCTCCACTTTCTGCTCCTCCTTGGATTCTTCTTCGTTTGTGTACTAAGAAAATGGGGAGGCAG
1806  GTGCATCAA TTTCTTATTGTGTAATAAGAAAATTGGGAAACGATCTTCAATATGCTT
      * * *     ** *** * * ******** ** ** * *** ***** *

532   TCTCTAA GAGATTGCTAC AGTGGG ACTCA ACTCTAAAGTTGTACAGACTTGCTAA
1865  ACCAAGCTGTGATTCCAAATATTACGTAAATACACTTGCAAAGGAGGATGTTTTAGTA
      * ******* *      * **  * ** * *** *   ***   ** * ***** *

588   GGAGGATGAAATTAGTAGCACTTTGCACTGTGAGG ATGG ACCTAGAGCTCCCCAGAGA
1924  GCAATTGTACTGA  TGGTATGGGGCCAAGAGATATCTTAGAGGGAGGGCTGAGGGTT
      * ***    * *  * * ****  ** *  **** ** ***  ** **** ***

646   AGGGCTGAAGGTCTGAAGTTGGTGCCAGGAACGTCTCGAAGACAGGTATA CTGTCAACA
1983  TGAAGTCCAACTCCTAAGCCAGTGCCAGTGCCAGAAGAG C CAAGGACAGGTACGGCTGTCATCA
      * *** ** **    ** ***    ***      * *** * ***   *

705   TTCAAGCCTCACCCTGTGGAACCACGCCCCTGGCCTGGGCCAATCTGCTCCCAGAGCAGG
2041  CTTAGACCTCACCCTGTGGAGCCAGCCACCCCTAGGGTTGGCCAATCTACTCCCAGGAGCAGG
      * ** *                *  *    *  *  *  *

765   GAGGGCAGGAGGCTGGGG GGGCATAAAAGGAAGAGCAGAGCCAGCAGCCACCTACATTT
2101  GAGGGCAGGAGCCAGGGCTGGGCATAAAAGTCAGGGCAGAGCCATCTATTGCTTACATTT
      ** *                            **        * ******

824   GCTTCTGACACAACCGTGTTCACTAGCAACTGCACAAACAGACAACATGGTGCATCTGTC
2161  GCTTCTGACACAACTGTGTTCACTAGCAAC CTCAAACAGACACACCATGGTGCACCTGAC
      * ****                          *                     *  *

884   TGCTGA        889
2219  TCCTGA        2224
      *
```

FIG. 9B

| Transgenic pigs obtained from construct 339 | | |
|---|---|---|
| Animal (Sex) | % Authentic Human Hb Expression | Copy # |
| 70-3(F) | 23 | 3 |
| 80-4(F) | 18 | 3-4 |
| 81-3(F) | 5 | n.d. |

Hb: Hemoglobin
n.d. not determined

FIG. 17

```
         10         20         30         40         50         60         70         80         90        100
AAAATAAAAG GCAGACAGTC TAAAATAGAA AACCAGTGGT ATNGTNGTTT ATTAATTGT GCTCATAACT TGAATACTCA TGTCTTTGTG CACAATTATT 110        120        130        140        150        160        170        180        190        200
CTTCCCTTGT ATTGATTAGG TCAAAGTAGA GGAAACCAAC TGTGTCAAAG CAGGAGCTGG ATGCAATCTT GGCAATAAGA ATCTTGCCAG TAGGGTCACG 210        220        230        240        250        260        270        280        290        300
TATGGCTTTT TCCTCCATCT TCAAGGGAAG GAGAGTTTTG GCCAGGACAT AAATGTTACA TGAGGTTCAA AACCTCTCTG GACTGTAAGC CAGGGAGCA 310        320        330        340        350        360        370        380        390        400
ACCTTCCTTT CCACATACTT TCCTNGCTCG GCTAACTCCC CAATGATAAA CATGCTTCTC TTTATACAAT AGACATTCCA CATGTTATAG TTAAGAGCTT 410        420        430        440        450        460        470
CCAGCCTGGG AGTCATTCTG TATCTTTCAG GTGACTTTGA GACACTTTTC CTATCAGTTA ATTACTTTT GATCCTC
```

FIG.27A

```
  47    GTTTATTA ATTTGTGCTCATAACTTGAATACTCATGTCTTTGTGCACAATTATTCTTTC
12499   GTTTTTTACACTGGAATTTATAACTAGAGCACTCATGTTTATGTAAGCAATTAATTGTTT
         *  * *** *    *  **      * *   ***       * **   *

106    CTTGTATTGATTAGGTCAAAGTAGAGGAAACCAACTGTGTCAAAGCAGG AGCTGGATGC
12559   CATC A  G TCAGGTAAAAGTAAAG AAA   AACTGTGCCAAGGCAGGTAGCCTAATGC
         * ** ** *     *     *    **     *  *      *    ***

165    AATCTTGGCAATAA G AATC TTGC CAGTAGG GTCACGTATGGCTTTTTCCTCCATC
12612   AATAT GCCACTAAAGTAAACATTATTCCATAGGTGTCAGATATGGCTTATTCATCCATC
            * * *   ** **    *** **    **   **         *  *

220    TTCAAGGGAAGGAGAGTTTTGGCCAGGACATAAATGTTACATGAGGTTCAAAACGTCTCT
12671   TTCATGGGAAGGATGGCCTTGGCCTGGACATCAGTGTTATGTGAGGTTCAAAACACCTCT
            *    ** **          *      * *   **  **           **

280    GGACTGTAAGCCAGGGGAGCAACCTTCCTTTCCA CA TACTTTCCTNGCTCGGCTAACT
12731   AGGCTATAAGGCAACAGAGCTCCTTTTTTTTTTTCTGTGCTTTCCTGGCT GTCCAAAT
         * *   *  *  *** ** * ****  ** *      * ***

338    CCCCAATGATAAACATGCTTCTCTTTATACAATAGACATTCCACATG TTATAGTTAAGA
12790   CTCTAATGATAAGCATACTTCTATTCA ATGAGA ATATTCTGTAAGATTATAGTTAAGA
         * *         *   *     * *  * *    ***  *

397    GCTTCCAGCCTGGGAGTCATTCTGTATCTTTCAGGTGACTTTGAGACACTTTTCCTATCA     456
12848   A TT   G  TGGGAGCCATTCCGTCTCTTATAGTTAAATTTGAGCTTCTTTTATGATCA   12901
         ** *** **    *   *    **  ***    ***    ***
```

FIG.27B

```
         10         20         30         40         50         60         70         80         90        100
GATCTCACGT ATATACGCAC CTAAAAAGTT GAATACATAG AGCTGCGAGT AGACGGTGGC TGCAGGGATG GGGAAAGTGG GAGAANCCAC TCAGATCTGG 110        120        130        140        150        160        170        180        190        200
GTCAAGGCA CAGGTCTTCA WNNATCTTTC AGTGACGTNA AGAGCTGGAG GTCTAATGGC TTACGGACTG TAGTAATGAC GCCACCACCGA ACGCTNGGAC 210        220        230        240        250        260        270        280        290        300
ATGTGCTAAG ATTTCGGGTG TTCTCATCAC ACCCCCAAAG TGGCAACTGT GAGGAAAGAC AGTTAAGTAA CCTGACTGAG GAGCCCTTTC CCTGTGTCTG 310        320        330        340        350        360        370        380        390        400
TGTCATACAC CTCGCATTAC ACCTCGCATT ACACGAGTTG CATCAAAAAA GAAAGTATTC AAAATAGCTA TATTTCTAAT CATCCTTTGG AGTTGAGATG 410        420        430        440        450        460        470        480        490        500
TGAGCCGAAG AGTTACATGT ACATGCTTGA CATTTGAACT CGAAATAATA TTTAGGGAGC ATGTATGATT TCTCTATCCC TTTACACAAT AAACTAAAAT 510        520        530        540        550        560        570        580        590        600
AATTCTCATG ATTTACCCTA TGACCTCCCC TCCAAGCCTA CCTGGCTCTG TCTCACGGTG TAGCCTGTTC TGCCCGCCCG GCCTTAAGGC 610        620        630        640        650        660        670        680        690        700
AGGTGGAGGA CAGGTATATC CTTGCCTTAT GGAAAATCCA CTGGGTCTTT CAAGGCCCAG TTTATTGTTC CTTTGGTTCC ATGAGACTTT TGGTAGCTCA 710        720        730        740        750        760        770        780        790        800
CTCCCTCCCT AAAAGGAACC CAGACTGAGG GTGGTATTTC CCTCCCATAT ATTTCTCTTT TAAGTGTGGA AAAGTATTC TAATAGTACA TATAATTATC 810        820        830        840        850        860        870        880        890        900
GACTGGTTTG TGTTGTTGT TCTTTTTTGG CCGTACCTGC AGCATATGAA CGTTCCTGGG CCAGGGACAG AATCCAAGCC AGAGCTGCGC CCTCCCCCAG 910        920        930        940        950        960        970        980        990
AGTACTACGGCA GTGCTGGATT CTTAACCCGCT GTGCTGGCC CGGATGTGAA CCCGCAAGC TACAGAGACT GAGCCCGATC GTTAACCCCT GCACTGCG

FIG.28
```

```
349   AAGAAAGTATTCAAAATAGCTATATTTCTAATCATCCTTTGGAGTTGAGATGTGAGCCGA
7276  AAGAAATACCTCCGAATAACTGTACCTCCAATTATTCTTTAAGGTAGC ATGCAACTGTA
      ****  **    *  *  **  *    *  *     ***  *  **    **  ****

409   AGAGTTACATGTACATGCTTGACATTTGAACTCGA A ATAATATTTAGGGAGCATGTAT
7335  ATAGTTGCATGTATATATTTATCATAATACTGTAACAGAAAACACTTACTGAATATATAC
        *    *  * **  **   *** *****  * *  *   **  **    *      *

467   GATTTCTCTATCCCTTTACACAATAAACTAAAATAATTCTCATGATT    513
7395  TGTGTCCCTAGTTCTTTACACAATAAACTAATCTCATCCTCATAATT   7441
       ** *  *   ***                    **  *        *

544   GGCTCTGTCTCACGGTGTCA TCCGTTGTAGCCTGTTC TGCCCGCCCGGCCTTAAGGCA
7784  GACTAAGTCACTCTGTCTCACTGTGTCTTAGCCAGTTCCTTACAGCTTGCCCTGATGGGA
       * **   *  * *   * ** **    *    * **    * **  **  *   *  *

602   GGTGGAGGACAGGTATATCCTTGCCTTATGGAAAATCCACTG CGTCTTTCAAGGCCCAG
7844  GATAGAGAATGGGTAT    CCTC CAACAAA AAAATAAATTTTCATTTCTCAAGGTCCAA
       *  *  *    ***       ** ** *** ***    ** *  ** *  *       * *

661   TTTATTGTTCCTTTGGTTCCATGAGACTTTTGGTAGCTCACTCCCTCCCTAAAAGGAACC
7900  CTTATGTTTCTTAATTTTTAAAAAAATCTTGACCATTCTC CACTCTCTAAAATAATCC
       *   **  *   ***   ** ** *  *         *****  * *  *         ** *

721    CAGACTGAGGGTGGTA TTT CCC   TCCCATATATTTCTCTTTTAAGTGTGGAAAA   773
7959  ACAGTGAGAGAAACATTCTTTTCCCCCATCCCATAAATACCTCTATTAAATATGGAAAA   8017
       *  ***  *****  **   *   ***     *  **   *      *  * *

529   CCTCCAAGGCTACGTGGCTCTGTCTCACGGTGTC   562
7777  CCTCTAAGACTAAGTCACTCTGTCTCACTGTGTC    7810
          *   *     **                *
```

FIG.29

```
         10         20         30         40         50         60         70         80         90        100
CCCCAAGTCC TGGTCCAGGG CCTGTCCATG GCGATTAAAT CACCCCAAGA AAGTCCCCGT CCTTCTCTGC CCTTCTCTGC GCTTCAGCCC CCTCTTCTCT AAAGGGCCTG 110        120        130        140        150        160        170        180        190        200
CAAAGGGCCC TCTGCCCCCG GAGAATTTCT CCTGCTGAAA CACACAGGCT CCCTCAGCTC AACCGGGACT GTCGCTACAT CTCGCCTGCA TTCGCCTGCA 210        220        230        240        250        260        270        280
CGACATCTGG GGTCTCTCAT CAGGGAGGGC CTTCTCTTCT AAACCAAGCC CACCCGGCCC TGGGAGCGTG GGACCAGAGA GG
```

FIG.30A

```
  40    TCACCCCAAGAAAGTCCCGTCCTTCTCTGCGCTTCAG    77
1450    TCATACTGAGAAAGTCCCCACCCTTCTCTGAGCCTCAG  1487
        **  **              **              **         *  *
```

FIG.30B

β-EXON 1

| | |
|---|---|
| HUMAN | ATG GTG CAC CTG ACT CCT GAG GAG AAG |
| PIG | ATG GTG CAt CTG tCT gCT GAG GAG AAG |

TCT GCC GTT ACT GCC CTG TGG GGC AAG GTG
gag GCC GTc ctc GgC CTG TGG GGC AAa GTG

AAC GTG GAT GAA GTT GGT GGT GAG GCC CTG
AAt GTG GAc GAA GTT GGT GGT GAG GCC CTG

GGC AG—G...
GGC AG—G...

β-EXON 2

| | |
|---|---|
| HUMAN | CTG CTG GTG GTC TAC CCT TGG ACC CAG |
| PIG | CTG CTG GTt GTC TAC CCc TGG ACt CAG |

AGG TTC TTT GAG TCC TTT GGG GAT CTG TCC
AGG TTC TTc GAG TCC TTT GGG GAc CTG TCC

ACT CCT GAT GCT GTT ATG GGC AAC CCT AAG
AaT gCc GAT GCc GTc ATG GGC AAt CCc AAG

GTG AAG GCT CAT GGC AAG AAA GTG CTC GGT
GTG AAG GCc CAc GGC AAG AAg GTG CTC cag

GCC TTT AGT GAT GGC CTG GCT CAC CTG GAC
tCC TTc AGT GAc GGC CTG aaa CAt CTc GAC

AAC CTC AAG GGC ACC TTT GCC ACA CTG AGT
AAC CTC AAG GGC ACC TTT GCt Aag CTG AGc

GAG CTG CAC TGT GAC AAG CTG CAC GTG GAT
GAG Tcg CAC TGT GAC cgG CTG CAC GTG GAT

CCT GAG AAC TTC AG—G...
CCT GAG AAC TTC AG—G...

FIG.35A

β -EXON3

| | |
|---|---|
| HUMAN | CTC CTG GGC AAC GTG CTG GTC TGT GTG |
| PIG | CTC CTG GGC AAC GTG aTa GTg gtT GTt |

CTG GCC CAT CAC TTT GGC AAA GAA TTC ACC
CTG GCt Cgc CgC cTT GGC cAt GAc TTC AaC

CCA CCA GTG CAG GCT GCC TAT CAG AAA GTG
CCg aat GTG CAG GCT GCt TtT CAG AAg GTG

GTG GCT GGT GTG GCT AAT GCC CTG GCC CAC
GTG GCT GGT GTt GCT AAT GCC CTG GCC CAC

AAG TAT CAC TAA
AAG TAc CAC TAA

FIG.35B

β -EXON 1

| | |
|---|---|
| HUMAN | ATG GTG CAC CTG ACT CCT GAG GAG AAG |
| OPTIMIZED | ATG GTG CAt CTG ACT CCT GAG GAG AAG |

TCT GCC GTT ACT GCC CTG TGG GGC AAG GTG
TCT GCC GTc ACT GCC CTG TGG GGC AAa GTG

AAC GTG GAT GAA GTT GGT GGT GAG GCC CTG
AAt GTG GAc GAA GTT GGT GGT GAG GCC CTG

GGC AG—G...
GGC AG—G...

β -EXON 2

| | |
|---|---|
| HUMAN | CTG CTG GTG GTC TAC CCT TGG ACC CAG |
| OPTIMIZED | CTG CTG GTt GTC TAC CCc TGG ACt CAG |

AGG TTC TTT GAG TCC TTT GGG GAT CTG TCC
AGG TTC TTc GAG TCC TTT GGG GAc CTG TCC

ACT CCT GAT GCT GTT ATG GGC AAC CCT AAG
ACT CCT GAT GCc GTc ATG GGC AAt CCc AAG

GTG AAG GCT CAT GGC AAG AAA GTG CTC GGT
GTG AAG GCc CAc GGC AAG AAg GTG CTC GGT

GCC TTT AGT GAT GGC CTG GCT CAC CTG GAC
GCC TTc AGT GAc GGC CTG GCT CAt CTc GAC

AAC CTC AAG GGC ACC TTT GCC ACA CTG AGT
AAC CTC AAG GGC ACC TTT GCt ACA CTG AGc

GAG CTG CAC TGT GAC AAG CTG CAC GTG GAT
GAG CTG CAC TGT GAC AAG CTG CAC GTG GAT

CCT GAG AAC TTC AG—G...
CCT GAG AAC TTC AG—G...

FIG.36A

β-EXON 3

| | |
|---|---|
| HUMAN | CTC CTG GGC AAC GTG CTG GTC TGT GTG |
| OPTIMIZED | CTC CTG GGC AAC GTG CTG GTg TGT GTt |

CTG GCC CAT CAC TTT GGC AAA GAA TTC ACC
CTG GCt CAT CAC TTT GGC AAA GAA TTC ACC

CCA CCA GTG CAG GCT GCC TAT CAG AAA GTG
CCg CCg GTG CAG GCT GCt TAT CAG AAg GTG

GTG GCT GGT GTG GCT AAT GCC CTG GCC CAC
GTG GCT GGT GTt GCT AAT GCC CTG GCC CAC

AAG TAT CAC TAA
AAG TAc CAC TAA

FIG.36B

β-EXON 1

```
OPTIMIZED    ATG GTG CAT CTG ACT CCT GAG GAG AAG
PIG          ATG GTG CAT CTG tCT gCT GAG GAG AAG

TCT GCC GTC ACT GCC CTG TGG GGC AAA GTG
             gag GCC GTC ctc GgC CTG TGG GGC AAA GTG AAT GTG GAC GAA GTT GGT GGT GAG GCC CTG
             AAT GTG GAC GAA GTT GGT GGT GAG GCC CTG

GGC AG—G...
             GGC AG—G...
```

β-EXON 2

```
OPTIMIZED    CTG CTG GTT GTC TAC CCC TGG ACT CAG
PIG          CTG CTG GTT GTC TAC CCC TGG ACT CAG

AGG TTC TTC GAG TCC TTT GGG GAC CTG TCC
             AGG TTC TTC GAG TCC TTT GGG GAC CTG TCC

ACT CCT GAT GCC GTC ATG GGC AAT CCC AAG
             AaT gCc GAT GCC GTC ATG GGC AAT CCC AAG

GTG AAG GCC CAC GGC AAG AAG GTG CTC GGT
             GTG AAG GCC CAC GGC AAG AAG GTG CTC cag GCC TTC AGT GAC GGC CTG GCT CAT CTC GAC
             tCC TTC AGT GAC GGC CTG aaa CAT CTC GAC AAC CTC AAG GGC ACC TTT GCT ACA CTG AGC
             AAC CTC AAG GGC ACC TTT GCT Aag CTG AGC GAG CTG CAC TGT GAC AAG CTG CAC GTG GAT
             GAG Tcg CAC TGT GAC caG CTG CAC GTG GAT

CCT GAG AAC TTC AG—G...
             CCT GAG AAC TTC AG—G...
```

FIG.37A

β-EXON 3

| | |
|---|---|
| OPTIMIZED | CTC CTG GGC AAC GTG CTG GTG TGT GTT |
| PIG | CTC CTG GGC AAC GTG aTa GTG gtT GTT |

```
         CTG GCT CAT CAC TTT GGC AAA GAA TTC ACC
         CTG GCT Cgc CgC cTT GGC cAt GAc TTC AaC

CCG CCG GTG CAG GCT GCT TAT CAG AAG GTG
         CCG aat GTG CAG GCT GCT TtT CAG AAG GTG GTG GCT GGT GTT GCT AAT GCC CTG GCC CAC
         GTG GCT GGT GTT GCT AAT GCC CTG GCC CAC

AAG TAC CAC TAA
         AAG TAC CAC TAA
```

FIG.37B

```
         10        20        30        40        50        60
          .         .         .         .         .         .
-CCATGGTGCATCTGACTCCTGAGGAGAAGTCTGCCGTCACTGCCCTGTGGGGCAAAGTG
 X  M  V  H  L  T  P  E  E  K  S  A  V  T  A  L  W  G  K  V>

70        80        90       100       110       120
          .         .         .         .         .         .
AATGTGGACGAAGTTGGTGGTGAGGCCCTGGGCAGG---CTGCTGGTTGTCTACCCCTGG
 N  V  D  E  V  G  G  E  A  L  G  R  -  L  L  V  V  Y  P  W>

130       140       150       160       170       180
          .         .         .         .         .         .
ACTCAGAGGTTCTTCGAGTCCTTTGGGGACCTGTCCACTCCTGATGCCGTCATGGGCAAT
 T  Q  R  F  F  E  S  F  G  D  L  S  T  P  D  A  V  M  G  N>

190       200       210       220       230       240
          .         .         .         .         .         .
CCCAAGGTGAAGGCCCACGGCAAGAAGGTGCTCGGTGCCTTCAGTGACGGCCTGGCTCAT
 P  K  V  K  A  H  G  K  K  V  L  G  A  F  S  D  G  L  A  H>

250       260       270       280       290       300
          .         .         .         .         .         .
CTCGACAACCTCAAGGGCACCTTTGCTACACTGAGCGAGCTGCACTGTGACAAGCTGCAC
 L  D  N  L  K  G  T  F  A  T  L  S  E  L  H  C  D  K  L  H>

310       320       330       340       350       360
          .         .         .         .         .         .
GTGGATCCTGAGAACTTCAGG---CTCCTGGGCAACGTGCTGGTGTGTGTTCTGGCTCAT
 V  D  P  E  N  F  R  -  L  L  G  N  V  L  V  C  V  L  A  H>

370       380       390       400       410       420
          .         .         .         .         .         .
CACTTTGGCAAAGAATTCACCCCGCCGGTGCAGGCTGCTTATCAGAAGGTGGTGGCTGGT
 H  F  G  K  E  F  T  P  P  V  Q  A  A  Y  Q  K  V  V  A  G>

430       440       450
          .         .         .
GTTGCTAATGCCCTGGCCCACAAGTACCACTAA
 V  A  N  A  L  A  H  K  Y  H  *>
```

FIG.38

```
                              10        20        30        40        50        60
                              .         .         .         .         .         .
HUMAN beta    MVHLTPEEKSAVTALWGKVNVDEVGGEALGR-LLVVYPWTQRFFESFGDLSTPDAVMGNP OPTIMIZED             10        20        30        40        50        60
[ 731 ]       MVHLTPEEKSAVTALWGKVNVDEVGGEALGR-LLVVYPWTQRFFESFGDLSTPDAVMGNP>
              ^^^^^^^^^^^^^^^^^^^^^^^^^^^^^^_^^^^^^^^^^^^^^^^^^^^^^^^^^^^^

70        80        90       100       110       120
                              *         *         *         *         *         *
HUMAN beta    KVKAHGKKVLGAFSDGLAHLDNLKGTFATLSELHCDKLHVDPENFR-LLGNVLVCVLAHH OPTIMIZED             70        80        90       100       110       120
[ 731 ]       KVKAHGKKVLGAFSDGLAHLDNLKGTFATLSELHCDKLHVDPENFR-LLGNVLVCVLAHH>
              ^^^^^^^^^^^^^^^^^^^^^^^^^^^^^^^^^^^^^^^^^^^^^_^^^^^^^^^^^^^

130       140       150
                              *         *         *
HUMAN beta    FGKEFTPPVQAAYQKVVAGVANALAHKYH*

OPTIMIZED             130       140       150
[ 731 ]       FGKEFTPPVQAAYQKVVAGVANALAHKYH>
              ^^^^^^^^^^^^^^^^^^^^^^^^^^^^^
```

FIG.39

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
       (A) LENGTH: 889 base pairs
       (B) TYPE: nucleic acid
       (C) STRANDEDNESS: double
       (D) TOPOLOGY: unknown (ii) MOLECULE TYPE: DNA (genomic)

(xi) SEQUENCE DESCRIPTION: SEQ ID NO:1:

```
CCCCAGCCCT TTTTCCAGGT CAGCGCAGGG AAAAAACATG TTCTCTGTCC CTGGTTATAC      60

TGTTTAGAAA CATCACCTCC CTCGGCGAAA CTAAAACTTG GGGGTTGCAA TTTATTCCTT     120

GCTTCTTTGT ATTTCGTACC ACATTGAGAG AGCTCTAGGT TTTCATCCGC AGATTCCCAA     180

ACCTTCGCAG AGGAGCTGTT TCACAGGACC GTGATTCAAG TTTACTCTAC TTTTCCATCA     240

TTTATTTGGT CATATGTTTA AATGAAGAAA GAAAGGAATG AAGATACCTG AATGAAATGA     300

GTATTTGTTT TCTTACCAGC AGGACTGAAT ACAAATGAAG AGAAGAAAAA TACGCACATT     360

TAGGACTTGG GCAGAGGTTT TATCCACGCT CTCCTTGTGG TTATTTCCCA TATTCAGAAG     420

GCGCGGGTGT GGATTCGTCT GTATGGTCCT AAATTGAACC ACAGTGGTCA AATCCCTCCA     480

CTTTCTGCTC CTTGGATTCT TCGTTTGTGT ACTAAGAAAA TGGGGAGGCA GTCTCTAAGA     540

GATTGCTACA GTGGGACTCA ACTCTAAAAG TTGTACAGAC TTGCTAAGGA GGATGAAATT     600

AGTAGCACTT TGCACTGTGA GGATGGACCT AGAGCTCCCC AGAGAAGGGC TGAAGGTCTG     660

AAGTTGGTGC CAGGAACGTC TCGAAGACAG GTATACTGTC AACATTCAAG CCTCACCCTG     720

TGGAACCACG CCCTGGCCTG GGCCAATCTG CTCCCAGAAG CAGGGAGGGC AGGAGGCTGG     780

GGGGGCATAA AAGGAAGAGC AGAGCCAGCA GCCACCTACA TTTGCTTCTG ACACAACCGT     840

GTTCACTAGC AACTGCACAA ACAGACAACA TGGTGCATCT GTCTGCTGA                 889
```

(2) INFORMATION FOR SEQ ID NO:2:

(i) SEQUENCE CHARACTERISTICS:
       (A) LENGTH: 273 base pairs
       (B) TYPE: nucleic acid
       (C) STRANDEDNESS: double
       (D) TOPOLOGY: unknown (ii) MOLECULE TYPE: DNA (genomic)

(xi) SEQUENCE DESCRIPTION: SEQ ID NO:2:

```
CCCCAGACAC TCTTGCAGAT TAGTCCAGGC AGAAACAGTT AGATGTCCCC AGTTAACCTC      60

CTATTTGACA CCACTGATTA CCCCATTGAT AGTCACACTT TGGGTTGTAA GTGACTTTTT     120

ATTTATTTGT ATTTTTGACT GCATTAAGAG GTCTCTAGTT TTTTATCTCT TGTTTCCCAA     180

AACCTAATAA GTAACTAATG CACAGAGCAC ATTGATTTGT ATTTATTCTA TTTTTAGACA     240

TAATTTATTA GCATGCATGA GCAAATTAAG AAA                                   273
```

(2) INFORMATION FOR SEQ ID NO:3:

(i) SEQUENCE CHARACTERISTICS:
       (A) LENGTH: 596 base pairs
       (B) TYPE: nucleic acid
       (C) STRANDEDNESS: double (D) TOPOLOGY: unknown (ii) MOLECULE TYPE: DNA (genomic)

(xi) SEQUENCE DESCRIPTION: SEQ ID NO:3:

TTTTTCTTTT CTTACCAGAA GGTTTTAATC CAAATAAGGA GAAGATATGC TTAGAACTGA     60

GGTAGAGTTT TCATCCATTC TGTCCTGTAA GTATTTTGCA TATTCTGGAG ACGCAGGAAG    120

AGATCCATCT ACATATCCCA AAGCTGAATT ATGGTAGACA AAGCTCTTCC ACTTTTAGTG    180

CATCAATTTC TTATTTGTGT AATAAGAAAA TTGGGAAAAC GATCTTCAAT ATGCTTACCA    240

AGCTGTGATT CCAAATATTA CGTAAATACA CTTGCAAAGG AGGATGTTTT TAGTAGCAAT    300

TTGTACTGAT GGTATGGGGC CAAGAGATAT ATCTTAGAGG GAGGGCTGAG GGTTTGAAGT    360

CCAACTCCTA AGCCAGTGCC AGAAGAGCCA AGGACAGGTA CGGCTGTCAT CACTTAGACC    420

TCACCCTGTG GAGCCACACC CTAGGGTTGG CCAATCTACT CCCAGGAGCA GGGAGGGCAG    480

GAGCCAGGGC TGGGCATAAA AGTCAGGGCA GAGCCATCTA TTGCTTACAT TTGCTTCTGA    540

CACAACTGTG TTCACTAGCA ACCTCAAACA GACACCATGG TGCACCTGAC TCCTGA        596

(2) INFORMATION FOR SEQ ID NO:4:

(i) SEQUENCE CHARACTERISTICS:
       (A) LENGTH: 477 base pairs
       (B) TYPE: nucleic acid
       (C) STRANDEDNESS: double
       (D) TOPOLOGY: unknown (ii) MOLECULE TYPE: DNA (genomic)

(xi) SEQUENCE DESCRIPTION: SEQ ID NO:4:

AAAATAAAAG GCAGACAGTC TAAAATAGAA AACCAGTGGT ATNGTNGTTT ATTAATTTGT     60

GCTCATAACT TGAATACTCA TGTCTTTGTG CACAATTATT CTTTCCTTGT ATTGATTAGG    120

TCAAAGTAGA GGAAACCAAC TGTGTCAAAG CAGGAGCTGG ATGCAATCTT GGCAATAAGA    180

ATCTTGCCAG TAGGGTCACG TATGGCTTTT TCCTCCATCT TCAAGGGAAG GAGAGTTTTG    240

GCCAGGACAT AAATGTTACA TGAGGTTCAA AACGTCTCTG GACTGTAAGC CAGGGGAGCA    300

ACCTTCCTTT CCACATACTT TCCTNGCTCG GCTAACTCCC CAATGATAAA CATGCTTCTC    360

TTTATACAAT AGACATTCCA CATGTTATAG TTAAGAGCTT CCAGCCTGGG AGTCATTCTG    420

TATCTTTCAG GTGACTTTGA GACACTTTTC CTATCAGTTA ATTTACTTTT GATCCTC       477

(2) INFORMATION FOR SEQ ID NO:5:

(i) SEQUENCE CHARACTERISTICS:
       (A) LENGTH: 403 base pairs
       (B) TYPE: nucleic acid
       (C) STRANDEDNESS: double
       (D) TOPOLOGY: unknown (ii) MOLECULE TYPE: DNA (genomic)

(xi) SEQUENCE DESCRIPTION: SEQ ID NO:5:

GTTTTTTACA CTGGAATTTA TAACTAGAGC ACTCATGTTT ATGTAAGCAA TTAATTGTTT     60

CATCAGTCAG GTAAAAGTAA AGAAAAACTG TGCCAAGGCA GGTAGCCTAA TGCAATATGC    120

CACTAAAGTA AACATTATTC CATAGGTGTC AGATATGGCT TATTCATCCA TCTTCATGGG    180

AAGGATGGCC TTGGCCTGGA CATCAGTGTT ATGTGAGGTT CAAAACACCT CTAGGCTATA    240

AGGCAACAGA GCTCCTTTTT TTTTTTTCTG TGCTTTCCTG GCTGTCCAAA TCTCTAATGA    300

TAAGCATACT TCTATTCAAT GAGAATATTC TGTAAGATTA TAGTTAAGAA TTGTGGGAGC    360

```
CATTCCGTCT CTTATAGTTA AATTTGAGCT TCTTTTATGA TCA                    403

(2) INFORMATION FOR SEQ ID NO:6:

(i) SEQUENCE CHARACTERISTICS:
        (A) LENGTH: 998 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:6:

GATCTCACGT ATATACGCAC CTAAAAAGTT GAATACATAG AGCTGCGAGT AGACGGTGGC    60

TGCAGGGATG GGGAAAGTGG GAGAANCCAC TCAGATCTGG GTCAAGGGCA CACGTCTTCA   120

NNNATCTTTC AGTGACGTNA AGACGTGGAG GTCTAATGGC TTACGGACTG TAGTAATGAC   180

GCAGCACCGA ACGCTNGGAC ATGTGCTAAG ATTTCGGGTG TTCTCATCAC ACCCCCAAAG   240

TGGCAACTGT GAGGAAAGAC AGTTAAGTAA CCTGACTGAG GAGCCGTTTC CCTGTGTCTG   300

TGTCATACAC CTCGCATTAC ACCTCGCATT ACACAGAGTTG CATCAAAAAA GAAAGTATTC   360

AAAATAGCTA TATTTCTAAT CATCCTTTGG AGTTGAGATG TGAGCCGAAG AGTTACATGT   420

ACATGCTTGA CATTTGAACT CGAAATAATA TTTAGGGAGC ATGTATGATT TCTCTATCCC   480

TTTACACAAT AAACTAAAAT AATTCTCATG ATTTACCCTA TGAGCTCCCC TCCAAGGCTA   540

CGTGGCTCTG TCTCACGGTG TCATCCGTTG TAGCCTGTTC TGCCCGCCCG GCCTTAAGGC   600

AGGTGGAGGA CAGGTATATC CTTGCCTTAT GGAAAATCCA CTGCGTCTTT CAAGGCCCAG   660

TTTATTGTTC CTTTGGTTCC ATGAGACTTT TGGTAGCTCA CTCCCTCCCT AAAAGGAACC   720

CAGACTGAGG GTGGTATTTC CCTCCCATAT ATTTCTCTTT TAAGTGTGGA AAAGGTATTC   780

TAATAGTACA TATAATTATC GACTGGTTTG TTGTTGTTGT TCTTTTTTGG CCGTACCTGC   840

AGCATATGAA CGTTCCTGGG CCAGGGACAG AATCCAAGCC AGAGCTGCGC CCTCCCCCAG   900

AGCTACGGCA GTGCTGGATT CTTAACCGCT GTGCTGGGCC CGGATGTGAA CCCGCAACGC   960

TACAGAGACT GAGCCGGATC GTTAACCGCT GCACTGCG                          998

(2) INFORMATION FOR SEQ ID NO:7:

(i) SEQUENCE CHARACTERISTICS:
        (A) LENGTH: 166 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:7:

AAGAAATACC TCCGAATAAC TGTACCTCCA ATTATTCTTT AAGGTAGCAT GCAACTGTAA    60

TAGTTGCATG TATATATTTA TCATAATACT GTAACAGAAA ACACTTACTG AATATATACT   120

GTGTCCCTAG TTCTTTACAC AATAAACTAA TCTCATCCTC ATAATT                 166

(2) INFORMATION FOR SEQ ID NO:8:

(i) SEQUENCE CHARACTERISTICS:
        (A) LENGTH: 234 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:8:
```

```
GACTAAGTCA CTCTGTCTCA CTGTGTCTTA GCCAGTTCCT TACAGCTTGC CCTGATGGGA    60

GATAGAGAAT GGGTATCCTC CAACAAAAAA ATAAATTTTC ATTTCTCAAG GTCCAACTTA   120

TGTTTTCTTA ATTTTTAAAA AAATCTTGAC CATTCTCCAC TCTCTAAAAT AATCCACAGT   180

GAGAGAAACA TTCTTTTCCC CCATCCCATA AATACCTCTA TTAAATATGG AAAA         234
```

(2) INFORMATION FOR SEQ ID NO:9:

(i) SEQUENCE CHARACTERISTICS:
        (A) LENGTH: 34 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:9:

```
CCTCTAAGAC TAAGTCACTC TGTCTCACTG TGTC                                34
```

(2) INFORMATION FOR SEQ ID NO:10:

(i) SEQUENCE CHARACTERISTICS:
        (A) LENGTH: 282 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:10:

```
CCCCAAGTCC TGGTCGAGGG CCTGTCCATG GCGATTAAAT CACCCCAAGA AAGTCCCCGT    60

CCTTCTCTGC GCTTCAGCCC CCTCTTCTGT AAAGGGCCTG CAAAGGGCCC TCTGCCGCCG   120

GAGAATTTCT CCTGCTGAAA CACACAGGCT CCCTCAGCTC AACCGGGACT GTCGCTACAT   180

CTATCACTTC TTCGCCTGCA CGACATCTGG GGTCTCTCAT CAGGGAGGGC CTTCTCTTCT   240

AAACCAAGCC CACCGGGCCC TGGGAGCGTG GGAGCAGAGA GG                      282
```

(2) INFORMATION FOR SEQ ID NO:11:

(i) SEQUENCE CHARACTERISTICS:
        (A) LENGTH: 38 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:11:

```
TCATACTGAG AAAGTCCCCA CCCTTCTCTG AGCCTCAG                            38
```

(2) INFORMATION FOR SEQ ID NO:12:

(i) SEQUENCE CHARACTERISTICS:
        (A) LENGTH: 93 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:12:

```
ATGGTGCACC TGACTCCTGA GGAGAAGTCT GCCGTTACTG CCCTGTGGGG CAAGGTGAAC    60

GTGGATGAAG TTGGTGGTGA GGCCCTGGGC AGG                                 93
```

(2) INFORMATION FOR SEQ ID NO:13:

(i) SEQUENCE CHARACTERISTICS:
        (A) LENGTH: 222 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:13:

```
CTGCTGGTGG TCTACCCTTG GACCCAGAGG TTCTTTGAGT CCTTTGGGGA TCTGTCCACT        60

CCTGATGCTG TTATGGGCAA CCCTAAGGTG AAGGCTCATG GCAAGAAAGT GCTCGGTGCC       120

TTTAGTGATG GCCTGGCTCA CCTGGACAAC CTCAAGGGCA CCTTTGCCAC ACTGAGTGAG       180

CTGCACTGTG ACAAGCTGCA CGTGGATCCT GAGAACTTCA GG                         222
```

(2) INFORMATION FOR SEQ ID NO:14:

(i) SEQUENCE CHARACTERISTICS:
        (A) LENGTH: 129 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:14:

```
CTCCTGGGCA ACGTGCTGGT CTGTGTGCTG GCCCATCACT TTGGCAAAGA ATTCACCCCA        60

CCAGTGCAGG CTGCCTATCA GAAAGTGGTG GCTGGTGTGG CTAATGCCCT GGCCCACAAG       120

TATCACTAA                                                              129
```

(2) INFORMATION FOR SEQ ID NO:15:

(i) SEQUENCE CHARACTERISTICS:
        (A) LENGTH: 93 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:15:

```
ATGGTGCATC TGTCTGCTGA GGAGAAGGAG GCCGTCCTCG GCCTGTGGGG CAAAGTGAAT        60

GTGGACGAAG TTGGTGGTGA GGCCCTGGGC AGG                                    93
```

(2) INFORMATION FOR SEQ ID NO:16:

(i) SEQUENCE CHARACTERISTICS:
        (A) LENGTH: 222 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:16:

```
CTGCTGGTTG TCTACCCCTG GACTCAGAGG TTCTTCGAGT CCTTTGGGGA CCTGTCCAAT        60

GCCGATGCCG TCATGGGCAA TCCCAAGGTG AAGGCCCACG GCAAGAAGGT GCTCCAGTCC       120

TTCAGTGACG GCCTGAAACA TCTCGACAAC CTCAAGGGCA CCTTTGCTAA GCTGAGCGAG       180

TCGCACTGTG ACCAGCTGCA CGTGGATCCT GAGAACTTCA GG                         222
```

(2) INFORMATION FOR SEQ ID NO:17:

(i) SEQUENCE CHARACTERISTICS:
    (A) LENGTH: 129 base pairs
    (B) TYPE: nucleic acid
    (C) STRANDEDNESS: double
    (D) TOPOLOGY: unknown (ii) MOLECULE TYPE: DNA (genomic)

(xi) SEQUENCE DESCRIPTION: SEQ ID NO:17:

```
CTCCTGGGCA ACGTGATAGT GGTTGTTCTG GCTCGCCGCC TTGGCCATGA CTTCAACCCG      60

AATGTGCAGG CTGCTTTTCA GAAGGTGGTG GCTGGTGTTG CTAATGCCCT GGCCCACAAG     120

TACCACTAA                                                              129
```

(2) INFORMATION FOR SEQ ID NO:18:

(i) SEQUENCE CHARACTERISTICS:
    (A) LENGTH: 95 base pairs
    (B) TYPE: nucleic acid
    (C) STRANDEDNESS: double
    (D) TOPOLOGY: unknown (ii) MOLECULE TYPE: cDNA (ix) FEATURE:
    (A) NAME/KEY: CDS
    (B) LOCATION: 3..95

(xi) SEQUENCE DESCRIPTION: SEQ ID NO:18:

```
CC ATG GTG CAT CTG ACT CCT GAG GAG AAG TCT GCC GTC ACT GCC CTG        47
   Met Val His Leu Thr Pro Glu Glu Lys Ser Ala Val Thr Ala Leu
   1               5                  10                  15

TGG GGC AAA GTG AAT GTG GAC GAA GTT GGT GGT GAG GCC CTG GGC AGG       95
Trp Gly Lys Val Asn Val Asp Glu Val Gly Gly Glu Ala Leu Gly Arg
              20                  25                  30
```

(2) INFORMATION FOR SEQ ID NO:19:

(i) SEQUENCE CHARACTERISTICS:
    (A) LENGTH: 31 amino acids
    (B) TYPE: amino acid
    (D) TOPOLOGY: linear (ii) MOLECULE TYPE: protein (xi) SEQUENCE DESCRIPTION: SEQ ID NO:19:

```
Met Val His Leu Thr Pro Glu Glu Lys Ser Ala Val Thr Ala Leu Trp
1               5                  10                  15

Gly Lys Val Asn Val Asp Glu Val Gly Gly Glu Ala Leu Gly Arg
              20                  25                  30
```

(2) INFORMATION FOR SEQ ID NO:20:

(i) SEQUENCE CHARACTERISTICS:
    (A) LENGTH: 222 base pairs
    (B) TYPE: nucleic acid
    (C) STRANDEDNESS: double
    (D) TOPOLOGY: unknown (ii) MOLECULE TYPE: cDNA (ix) FEATURE:
    (A) NAME/KEY: CDS
    (B) LOCATION: 1..222

(xi) SEQUENCE DESCRIPTION: SEQ ID NO:20:

```
CTG CTG GTT GTC TAC CCC TGG ACT CAG AGG TTC TTC GAG TCC TTT GGG       48
Leu Leu Val Val Tyr Pro Trp Thr Gln Arg Phe Phe Glu Ser Phe Gly
1               5                  10                  15
```

```
GAC CTG TCC ACT CCT GAT GCC GTC ATG GGC AAT CCC AAG GTG AAG GCC        96
Asp Leu Ser Thr Pro Asp Ala Val Met Gly Asn Pro Lys Val Lys Ala
            20                  25                  30

CAC GGC AAG AAG GTG CTC GGT GCC TTC AGT GAC GGC CTG GCT CAT CTC       144
His Gly Lys Lys Val Leu Gly Ala Phe Ser Asp Gly Leu Ala His Leu
        35                  40                  45

GAC AAC CTC AAG GGC ACC TTT GCT ACA CTG AGC GAG CTG CAC TGT GAC       192
Asp Asn Leu Lys Gly Thr Phe Ala Thr Leu Ser Glu Leu His Cys Asp
    50                  55                  60

AAG CTG CAC GTG GAT CCT GAG AAC TTC AGG                               222
Lys Leu His Val Asp Pro Glu Asn Phe Arg
65                  70
```

(2) INFORMATION FOR SEQ ID NO:21:

(i) SEQUENCE CHARACTERISTICS:
        (A) LENGTH: 74 amino acids
        (B) TYPE: amino acid
        (D) TOPOLOGY: linear (ii) MOLECULE TYPE: protein (xi) SEQUENCE DESCRIPTION: SEQ ID NO:21:

```
Leu Leu Val Val Tyr Pro Trp Thr Gln Arg Phe Phe Glu Ser Phe Gly
1               5                   10                  15

Asp Leu Ser Thr Pro Asp Ala Val Met Gly Asn Pro Lys Val Lys Ala
            20                  25                  30

His Gly Lys Lys Val Leu Gly Ala Phe Ser Asp Gly Leu Ala His Leu
        35                  40                  45

Asp Asn Leu Lys Gly Thr Phe Ala Thr Leu Ser Glu Leu His Cys Asp
    50                  55                  60

Lys Leu His Val Asp Pro Glu Asn Phe Arg
65                  70
```

(2) INFORMATION FOR SEQ ID NO:22:

(i) SEQUENCE CHARACTERISTICS:
        (A) LENGTH: 129 base pairs
        (B) TYPE: nucleic acid
        (C) STRANDEDNESS: double
        (D) TOPOLOGY: unknown (ii) MOLECULE TYPE: cDNA (ix) FEATURE:
        (A) NAME/KEY: CDS
        (B) LOCATION: 1..129

(xi) SEQUENCE DESCRIPTION: SEQ ID NO:22:

```
CTC CTG GGC AAC GTG CTG GTG TGT GTT CTG GCT CAT CAC TTT GGC AAA        48
Leu Leu Gly Asn Val Leu Val Cys Val Leu Ala His His Phe Gly Lys
1               5                   10                  15

GAA TTC ACC CCG CCG GTG CAG GCT GCT TAT CAG AAG GTG GTG GCT GGT        96
Glu Phe Thr Pro Pro Val Gln Ala Ala Tyr Gln Lys Val Val Ala Gly
            20                  25                  30

GTT GCT AAT GCC CTG GCC CAC AAG TAC CAC TAA                           129
Val Ala Asn Ala Leu Ala His Lys Tyr His
        35                  40
```

(2) INFORMATION FOR SEQ ID NO:23:

(i) SEQUENCE CHARACTERISTICS:
        (A) LENGTH: 42 amino acids
        (B) TYPE: amino acid
        (D) TOPOLOGY: linear (ii) MOLECULE TYPE: protein (xi) SEQUENCE DESCRIPTION: SEQ ID NO:23:

Leu Leu Gly Asn Val Leu Val Cys Val Leu Ala His His Phe Gly Lys
1               5                   10                  15

Glu Phe Thr Pro Pro Val Gln Ala Ala Tyr Gln Lys Val Val Ala Gly
                20                  25                  30

Val Ala Asn Ala Leu Ala His Lys Tyr His
            35                  40

(2) INFORMATION FOR SEQ ID NO:24:

(i) SEQUENCE CHARACTERISTICS:
        (A) LENGTH: 31 amino acids
        (B) TYPE: amino acid
        (D) TOPOLOGY: linear (ii) MOLECULE TYPE: protein (xi) SEQUENCE DESCRIPTION: SEQ ID NO:24:

Met Val His Leu Thr Pro Glu Glu Lys Ser Ala Val Thr Ala Leu Trp
1               5                   10                  15

Gly Lys Val Asn Val Asp Glu Val Gly Gly Glu Ala Leu Gly Arg
                20                  25                  30

(2) INFORMATION FOR SEQ ID NO:25:

(i) SEQUENCE CHARACTERISTICS:
        (A) LENGTH: 74 amino acids
        (B) TYPE: amino acid
        (D) TOPOLOGY: linear (ii) MOLECULE TYPE: protein (xi) SEQUENCE DESCRIPTION: SEQ ID NO:25:

Leu Leu Val Val Tyr Pro Trp Thr Gln Arg Phe Phe Glu Ser Phe Gly
1               5                   10                  15

Asp Leu Ser Thr Pro Asp Ala Val Met Gly Asn Pro Lys Val Lys Ala
                20                  25                  30

His Gly Lys Lys Val Leu Gly Ala Phe Ser Asp Gly Leu Ala His Leu
            35                  40                  45

Asp Asn Leu Lys Gly Thr Phe Ala Thr Leu Ser Glu Leu His Cys Asp
        50                  55                  60

Lys Leu His Val Asp Pro Glu Asn Phe Arg
65                  70

(2) INFORMATION FOR SEQ ID NO:26:

(i) SEQUENCE CHARACTERISTICS:
        (A) LENGTH: 42 amino acids
        (B) TYPE: amino acid
        (D) TOPOLOGY: linear (ii) MOLECULE TYPE: protein (xi) SEQUENCE DESCRIPTION: SEQ ID NO:26:

Leu Leu Gly Asn Val Leu Val Cys Val Leu Ala His His Phe Gly Lys
1               5                   10                  15

Glu Phe Thr Pro Pro Val Gln Ala Ala Tyr Gln Lys Val Val Ala Gly
                20                  25                  30

Val Ala Asn Ala Leu Ala His Lys Tyr His
            35                  40

PURIFYING HUMAN HEMOGLOBLIN FROM TRANSGENIC PIG RED CELLS AND PLASMIDS CONTAINING PIG GLOBIN NUCLEIC ACIDS

This application is a continuation-in-part of U.S. Ser. No. 08/030,897, filed Mar. 15, 1993, now abandoned, which is a continuation-in-part of U.S. Ser. No. 07/897,648, filed Jun. 12, 1992, now abandoned, which is a continuation-in-part of U.S. Ser. No. 07/717,774, filed Jun. 14, 1991, now abandoned.

1. INTRODUCTION

The present invention relates to the use of transgenic pigs for the production of human hemoglobin. The transgenic pigs of the invention may be used as an efficient and economical source of cell-free human hemoglobin that may be used for transfusions and other medical applications in humans.

2. BACKGROUND OF THE INVENTION

2.1. HEMOGLOBIN

Oxygen absorbed through the lungs is carried by hemoglobin in red blood cells for delivery to tissues throughout the body. At high oxygen tensions, such as those found in the proximity of the lungs, oxygen binds to hemoglobin, but is released in areas of low oxygen tension, where it is needed.

Each hemoglobin molecule consists of two alpha globin and two beta globin subunits. Each subunit, in turn, is noncovalently associated with an iron-containing heme group capable of carrying an oxygen molecule. Thus, each hemoglobin tetramer is capable of binding four molecules of oxygen. The subunits work together in switching between two conformational states to facilitate uptake and release of oxygen at the lungs and tissues, respectively. This effect is commonly referred to as heme-heme interaction or cooperativity.

The hemoglobins of many animals are able to interact with biologic effector molecules that can further enhance oxygen binding and release. This enhancement is manifested in changes which affect the allosteric equilibrium between the two conformational states of hemoglobin. For example, human and pig hemoglobin can bind 2, 3 diphosphoglycerate (2,3 DPG), which influences the equilibrium between the two conformational states of the tetramer and has the net effect of lowering the overall affinity for oxygen at the tissue level. As a result, 2,3-DPG increases the efficiency of oxygen delivery to the tissues.

2.2. GLOBIN GENE EXPRESSION

Hemoglobin protein is expressed in a tissue specific manner in red blood cells where it accounts for approximately ninety percent of total cellular protein. Thus, red blood cells, which have lost their nucleus and all but a minimal number of organelles, are effectively membrane-enclosed packets of hemoglobin dedicated to oxygen transfer.

Humans and various other species produce different types of hemoglobin during embryonic, fetal, and adult developmental periods. Therefore, the factors that influence globin gene expression must be able to achieve tissue specific control, quantitative control, and developmentally regulated control of globin expression.

Human globin genes are found in clusters on chromosome 16 for alpha ($\alpha$) globin and chromosome 11 for beta ($\beta$) globin. The human beta globin gene cluster consists of about 50 kb of DNA that includes one embryonic gene encoding epsilon ($\epsilon$) globin, two fetal genes encoding gamma ($\gamma$) G and gamma A globin, and two adult genes encoding delta ($\delta$) and beta ($\beta$) globin, in that order (Fritsch et al., 1980, Cell 19:959–972).

It has been found that DNA sequences both upstream and downstream of the $\beta$ globin translation initiation site are involved in the regulation of $\beta$ globin gene expression (Wright et al., 1984, Cell 38:263). In particular, a series of four Dnase I super hypersensitive sites (now referred to as the locus control region, or LCR) located about 50 kilobases upstream of the human beta globin gene are extremely important in eliciting properly regulated beta globin-locus expression (Tuan et al., 1985, Proc. Natl. Acad. Sci. U.S.A. 83:1359–1363; PCT Patent Application WO 8901517 by Grosveld; Behringer et al., 1989, Science 245:971–973; Enver et al., 1989, Proc. Natl. Acad. Sci. U.S.A. 86:7033–7037; Hanscombe et al., 1989, Genes Dev. 3:1572–1581; Van Assendelft et al., 1989, Cell 56:967–977; Grosveld et al., 1987, Cell 51:975–985).

2.3. THE NEED FOR A BLOOD SUBSTITUTE

Recently, the molecular aspects of globin gene expression have met with even greater interest as researchers have attempted to use genetic engineering to produce a synthetic blood that would avoid the pitfalls of donor generated blood. In 1988, between 12 million and 14 million units of blood were used in the United States alone (Andrews, Feb. 18, 1990, New York Times), an enormous volume precariously dependent on volunteer blood donations. About 5 percent of donated blood is infected by hepatitis virus (Id.) and, although screening procedures for HIV infection are generally effective, the prospect of contracting transfusion related A.I.D.S. remains a much feared possibility. Furthermore, transfused blood must be compatible with the blood type of the transfusion recipient; the donated blood supply may be unable to provide transfusions to individuals with rare blood types. In contrast, hemoglobin produced by genetic engineering would not require blood type matching, would be virus-free, and would be available in potentially unlimited amounts. Several research groups have explored the possibility of expressing hemoglobin in microorganisms. For example, see International Application No. PCT/US88/01534 by Hoffman and Nagai, which presents, in working examples, production of human globin protein in *E. coli*.

2.4. TRANSGENIC ANIMALS

A transgenic animal is a non-human animal containing at least one foreign gene, called a transgene, in its genetic material. Preferably, the transgene is contained in the animal's germ line such that it can be transmitted to the animal's offspring. A number of techniques may be used to introduce the transgene into an animal's genetic material, including, but not limited to, microinjection of the transgene into pronuclei of fertilized eggs and manipulation of embryonic stem cells (U.S. Pat. No. 4,873,191 by Wagner and Hoppe; Palmiter and Brinster, 1986, Ann. Rev. Genet. 20:465–499; French Patent Application 2593827 published Aug. 7, 1987). Transgenic animals may carry the transgene in all their cells or may be genetically mosaic.

Although the majority of studies have involved transgenic mice, other species of transgenic animal have also been produced, such as rabbits, sheep, pigs (Hammer et al., 1985, Nature 315:680–683) and chickens (Salter et al., 1987, Virology 157:236–240). Transgenic animals are currently being developed to serve as bioreactors for the production of useful pharmaceutical compounds (Van Brunt, 1988, Bio/Technology 6:1149–1154; Wilmut et al., 1988, New Scientist (July 7 issue) pp. 56–59).

Methods of expressing recombinant protein via transgenic livestock have an important theoretical advantage over protein production in recombinant bacteria and yeast; namely, the ability to produce large, complex proteins in which post-translational modifications, including glycosylation, phosphorylation, subunit assembly, etc. are critical for the activity of the molecule.

In practice, however, the creation of transgenic livestock has proved problematic. Not only is it technically difficult to produce transgenic embryos, but mature transgenic animals that produce significant quantities of recombinant protein may prove inviable. In pigs in particular, the experience has been that pigs carrying a growth hormone encoding transgene (the only transgene introduced into pigs prior to the present invention) suffered from a number of health problems, including severe arthritis, lack of coordination in their rear legs, susceptibility to stress, anoestrus in gilts and lack of libido in boars (Wilmut et al., supra). This is in contrast to transgenic mice carrying a growth hormone transgene, which appeared to be healthy (Palmiter et al., 1982, Nature 300:611–615). Thus, prior to the present invention, healthy transgenic pigs (which efficiently express their transgene(s)) had not been produced.

2.5. EXPRESSION OF GLOBIN GENES IN TRANSGENIC ANIMALS

Transgenic mice carrying human globin transgenes have been used in studying the molecular biology of globin gene expression. A hybrid mouse/human adult beta globin gene was described by Magram et al. in 1985(Nature 315:338–340). Kollias et al. then reported regulated expression of human gamma-A, beta, and hybrid beta/gamma globin genes in transgenic mice (1986, Cell 46:89–94). Transgenic mice expressing human fetal gamma globin were studied by Enver et al. (1989, Proc. Natl. Acad. Sci. U.S.A. 86:7033–7037) and Constantoulakis et al. (1991, Blood 77:1326–1333). Autonomous developmental control of human embryonic globin gene switching in transgenic mice was observed by Raich et al. (1990, Science 250:1147–1149).

Transgenic mouse models for a variety of disorders of hemoglobin or hemoglobin expression have been developed, including sickle cell disease (Rubin et al., 1988, Am. J. Human Genet. 42:585–591; Greaves et al., 1990, Nature 343:183–185; Ryan et al., 1990, Science 247:566–568; Rubin et al., 1991, J. Clin. Invest. 87:639–647); thalassemia (Anderson et al., 1985, Ann. New York Acad. Sci. (USA) 445:445–451; Sorenson et al., 1990, Blood 75:1333–1336); and hereditary persistence of fetal hemoglobin (Tanaka et al., 1990, Ann. New York Acad. Sci. (USA) 612:167–178).

Concurrent expression of human alpha and beta globin has led to the production of human hemoglobin in transgenic mice (Behringer et al., 1989, Science 245:971–973; Townes et al., 1989, Prog. Clin. Biol. Res. 316A:47–61; Hanscombe et al., 1989, Genes Dev. 3:1572–1581). It was observed by Hanscombe et al. (supra) that transgenic fetuses with high copy numbers of a transgene encoding alpha but not beta globin exhibited severe anemia and died prior to birth. Using a construct with both human alpha and beta globin genes under the control of the beta globin LCR, live mice with low copy numbers were obtained (Id.). Metabolic labeling experiments showed balanced mouse globin synthesis, but imbalanced human globin synthesis, with an alpha/beta biosynthetic ratio of about 0.6 (Id.).

3. SUMMARY OF THE INVENTION

The present invention relates to the use of transgenic pigs for the production of human hemoglobin and/or human globin. It is based, at least in part, on the discovery that transgenic pigs may be generated that express human hemoglobin in their erythrocytes and are healthy, suffering no deleterious effects as a result of heterologous hemoglobin production.

In particular embodiments, the present invention provides for transgenic pigs that express human globin genes. Such animals may be used as a particularly efficient and economical source of human hemoglobin, in light of (i) the relatively short periods of gestation and sexual maturation in pigs; (ii) the size and frequency of litters, (iii) the relatively large size of the pig which provides proportionately large yields of hemoglobin; and (iv) functional similarities between pig and human hemoglobins in the regulation of oxygen binding affinity which enables the transgenic pigs to remain healthy in the presence of high levels of human hemoglobin.

The present invention also provides for recombinant nucleic acid constructs that may be used to generate transgenic pigs. In specific, nonlimiting embodiments, such constructs (1) place the human alpha and beta globin genes under the same promoter; (ii) comprise the pig adult beta globin gene regulatory region, comprising the promoter or the 3' region of the pig beta globin gene; and/or (iii) comprise the human globin genes under the control of the porcine locus control region (LCR).

The present invention also provides for constructs comprising an optimized human β-globin gene in which said human β-globin gene is genetically engineered to be similar to the pig β-globin gene, but without altering the amino acid sequence of the encoded wild-type human β-globin. Such constructs may increase the level of human β-globin in transgenic pigs by affecting mRNA structure, stability or rate of translation.

In an additional embodiment, the present invention provides for a hybrid hemoglobin that comprises human α globin and pig β globin. The whole blood from transgenic pigs expressing this hybrid hemoglobin appears to exhibit a $P_{50}$ that is advantageously higher than that of native human or pig blood.

The present invention also provides for a method of producing human hemoglobin comprising (i) introducing a human alpha globin and a human beta globin gene, under the control of a suitable promoter or promoters, into the genetic material of a pig so as to create a transgenic pig that expresses human hemoglobin in at least some of its red blood cells; (ii) collecting red blood cells from the transgenic pig; (iii) releasing the contents of the collected red blood cells; and (iv) subjecting the released contents of the red blood cells to a purification procedure that substantially separates human hemoglobin from pig hemoglobin. In a preferred embodiment of the invention, human hemoglobin may be separated from pig hemoglobin by DEAE anion exchange column chromatography.

4. DESCRIPTION OF THE FIGURES

FIGS. 1A, 1B, 1C, 1D, 1E, 1F, 1G, 1H, 1I, 1J, 1K, 1L, 1M, 1N, 1O, 1P, 1Q, 1R, 1S, 1T, 1U, 1V, 1W, 1X, and 1Y. Recombinant nucleic acid constructs.

Figure 1B:
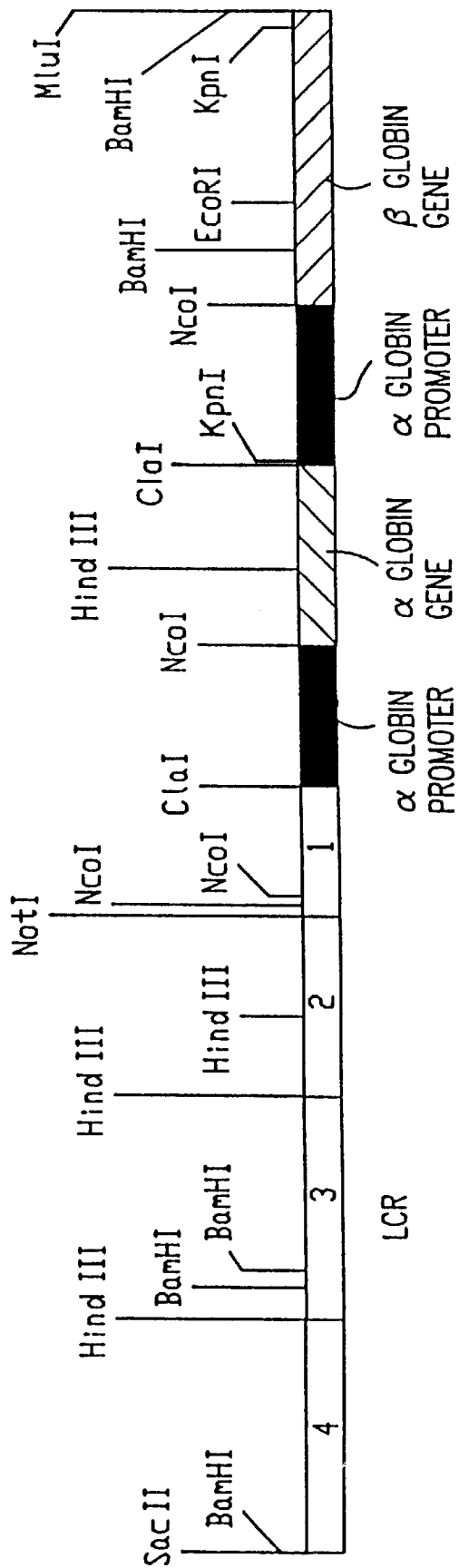
Figure 1C:
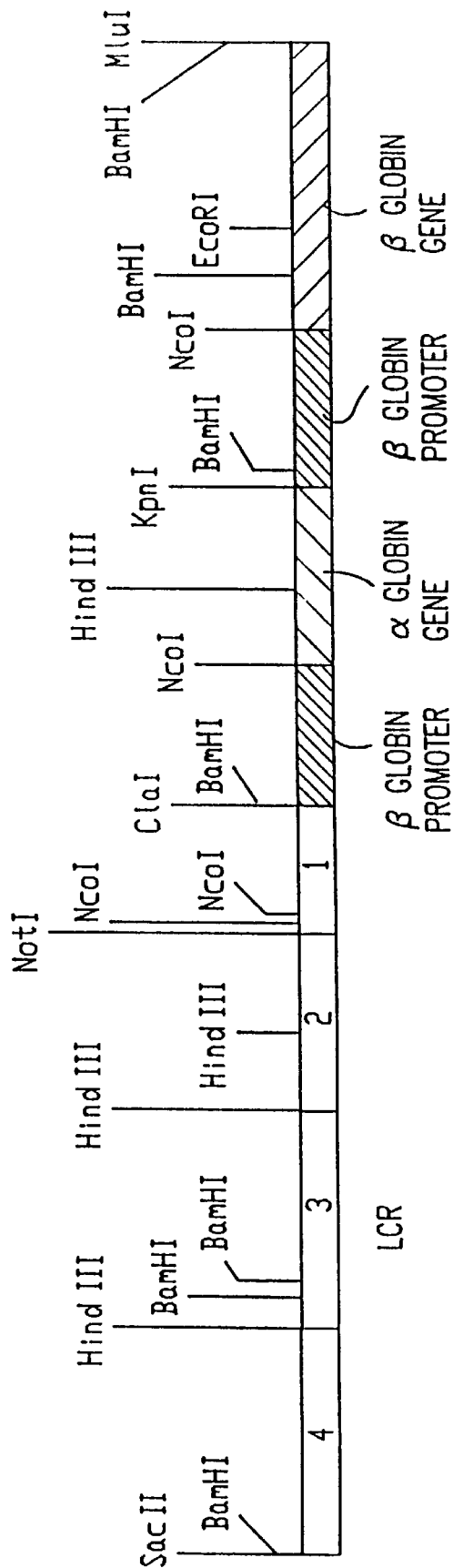
Figure 1D:
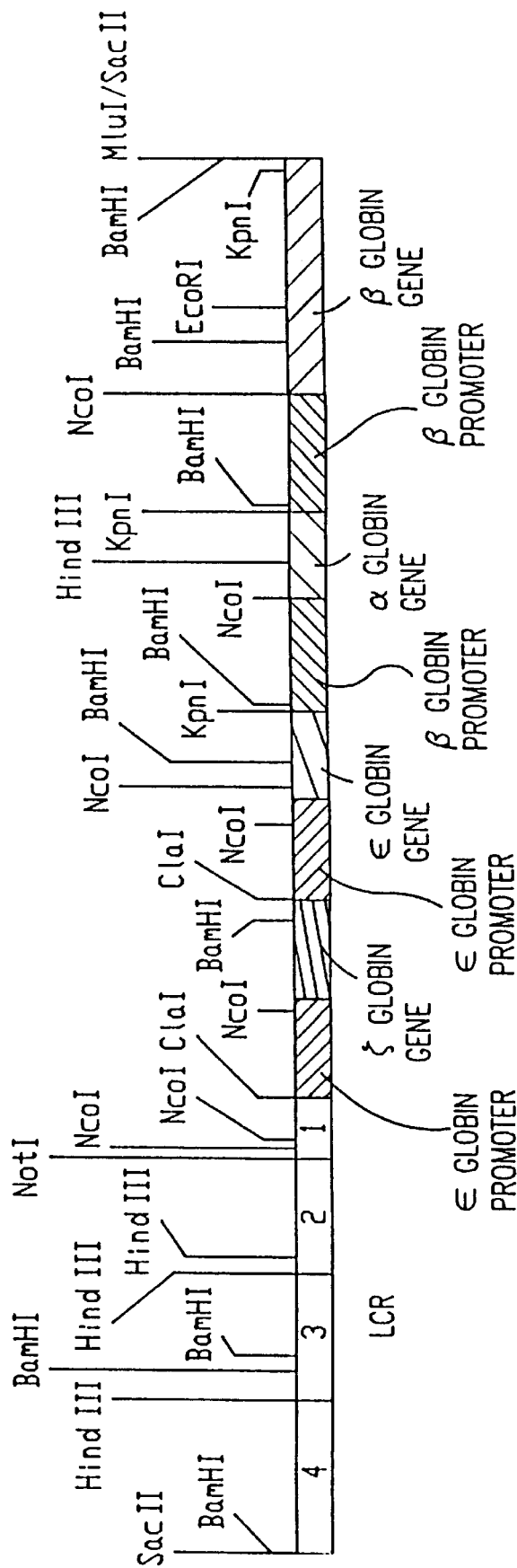
Figure 1E:
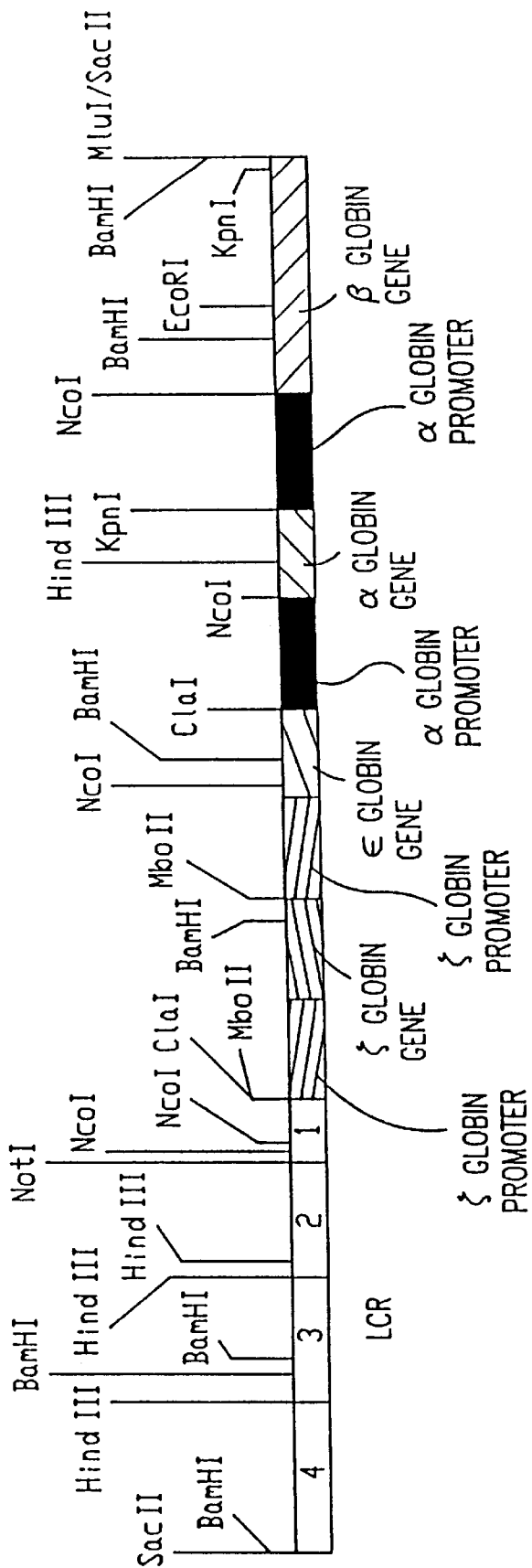
Figure 1F:
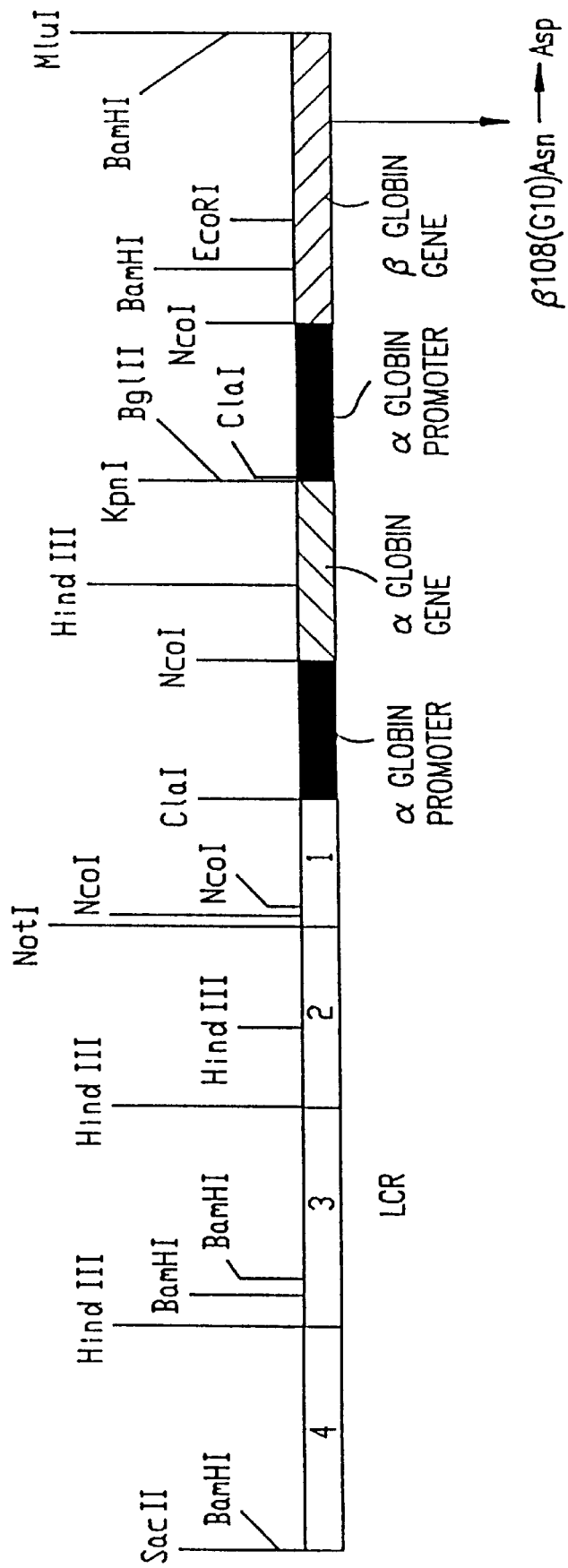
Figure 1G:
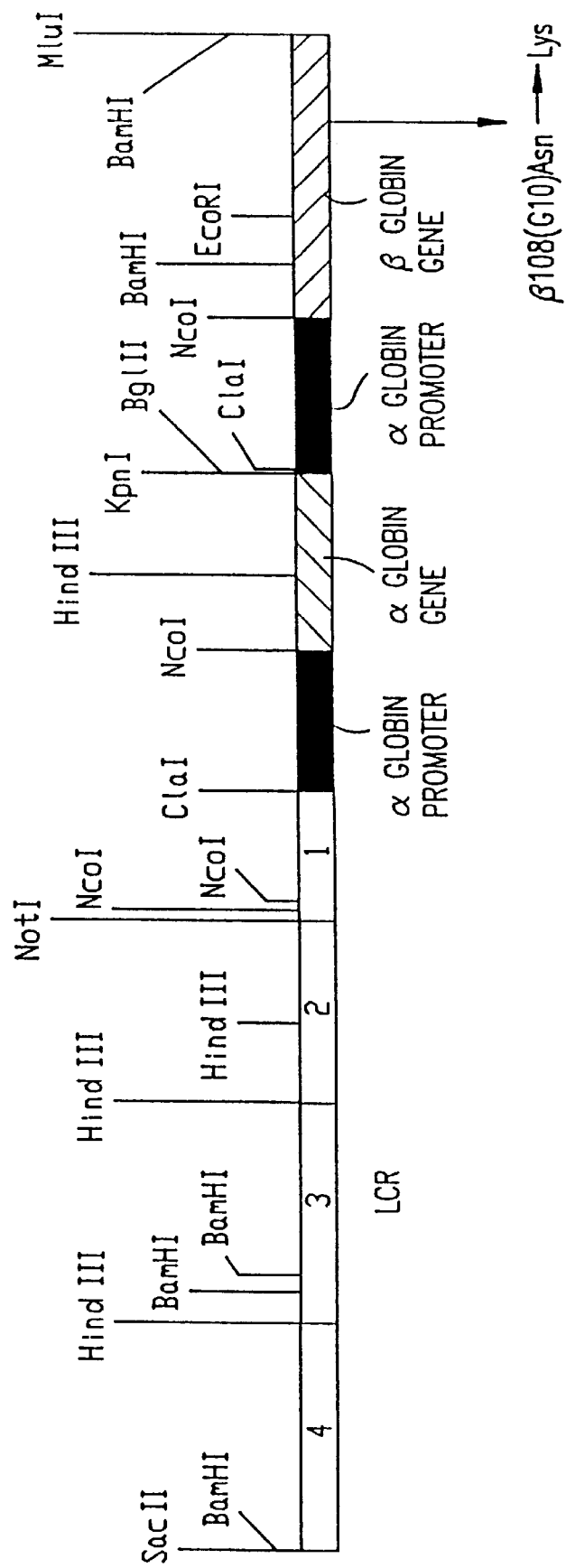
Figure 1H:
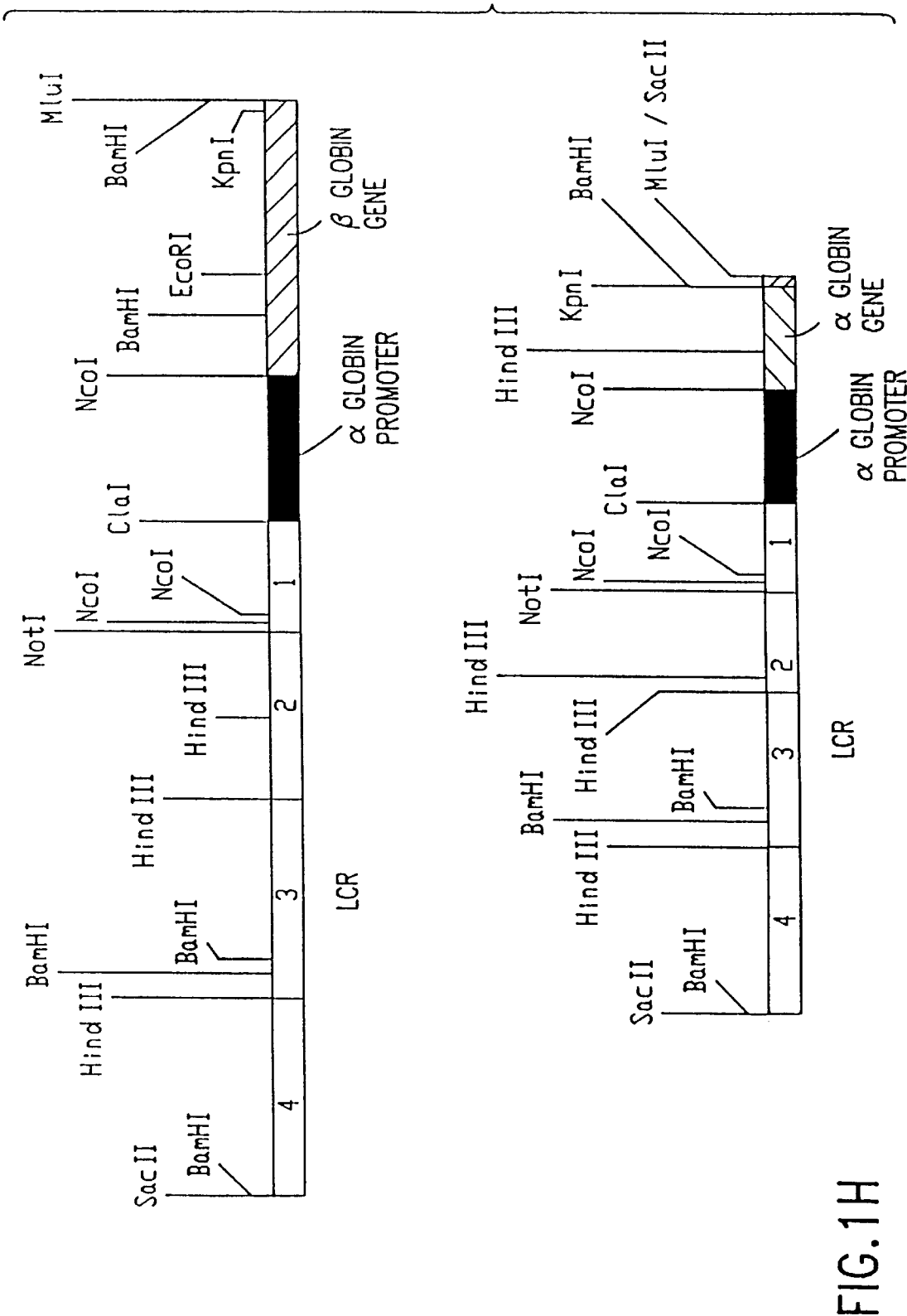
Figure 1J:
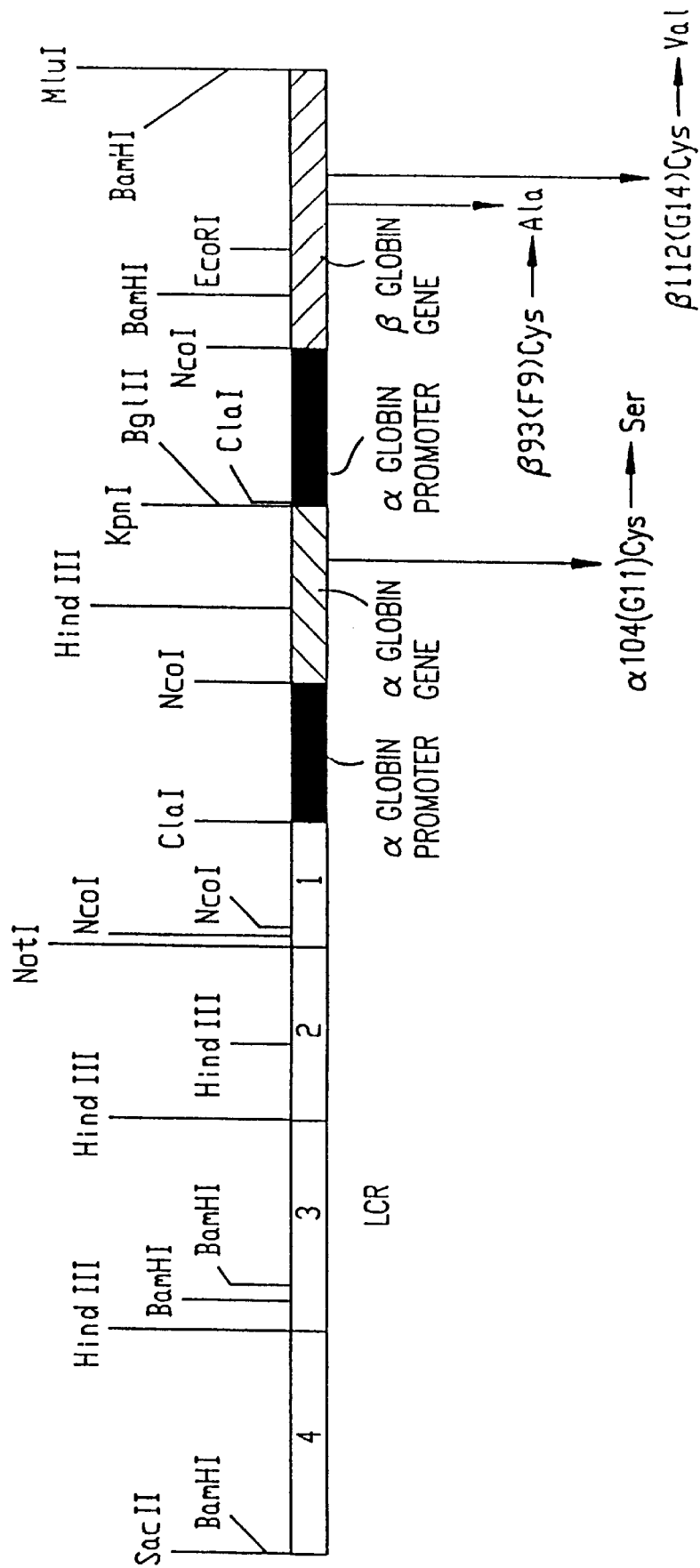
Figure 1K:
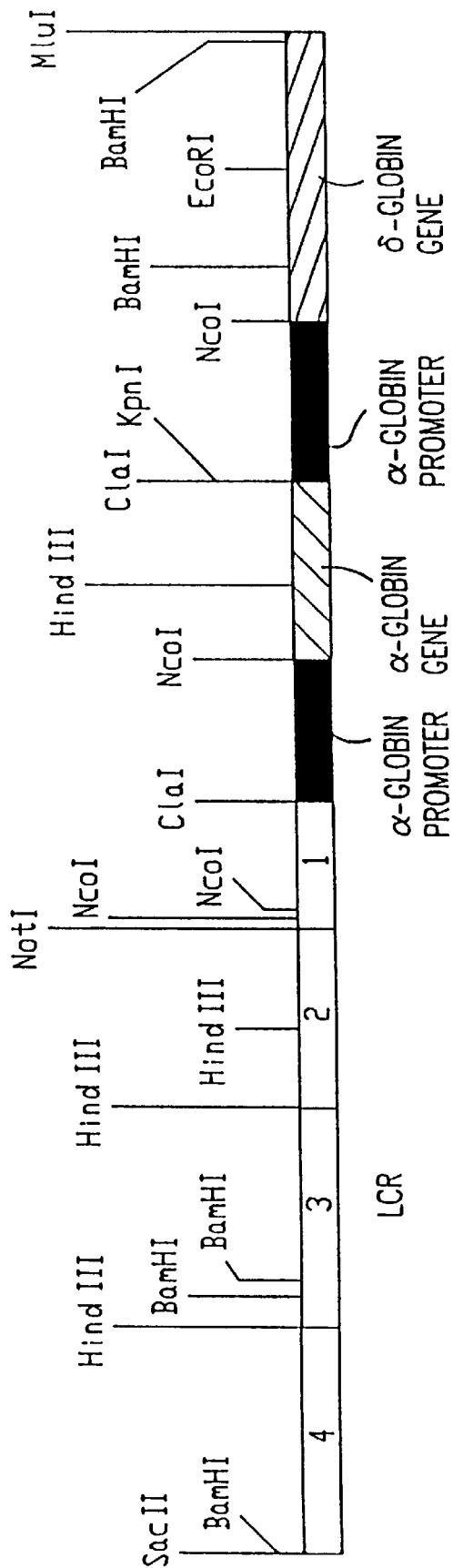
Figure 1L:
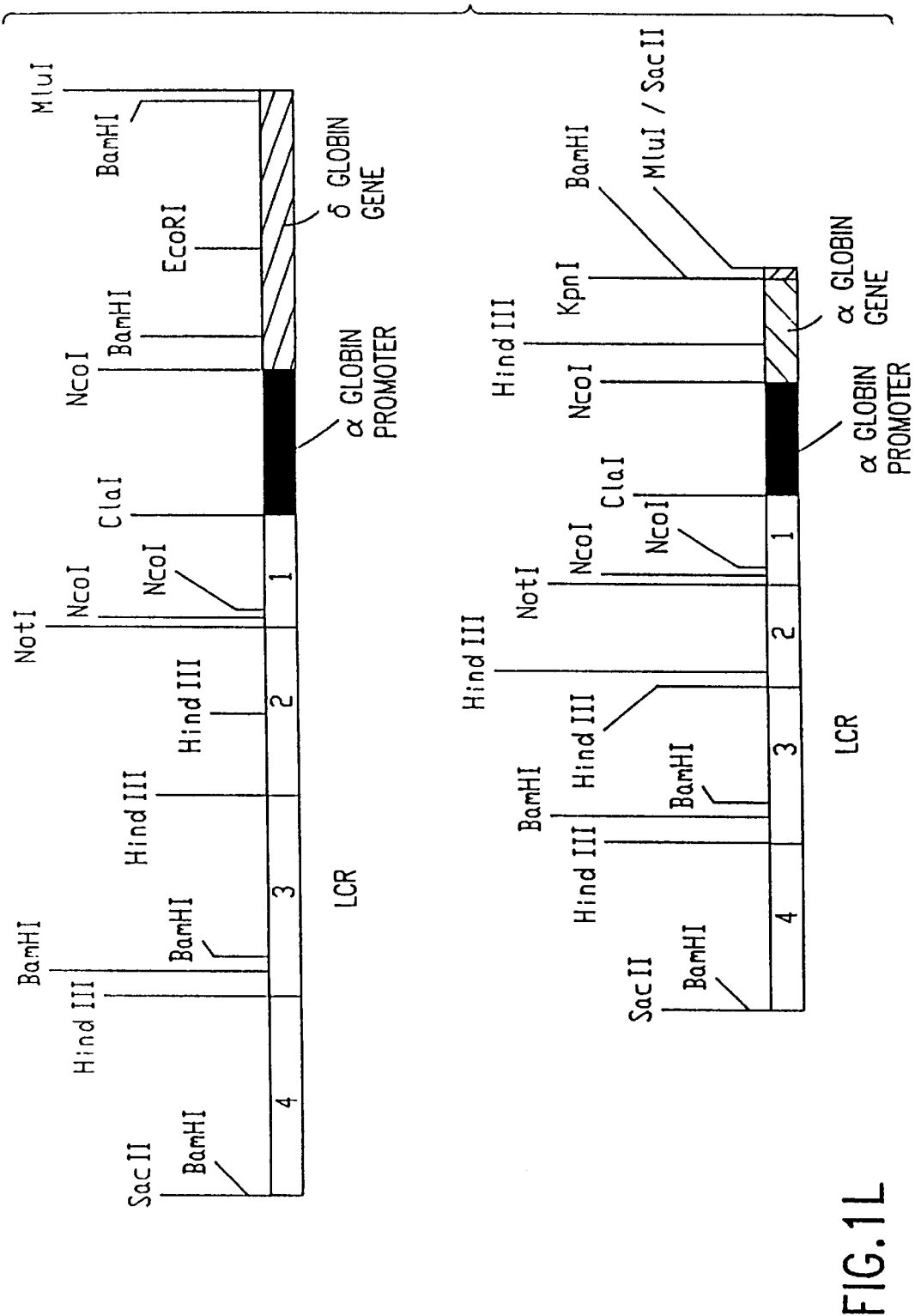
Figure 1M:
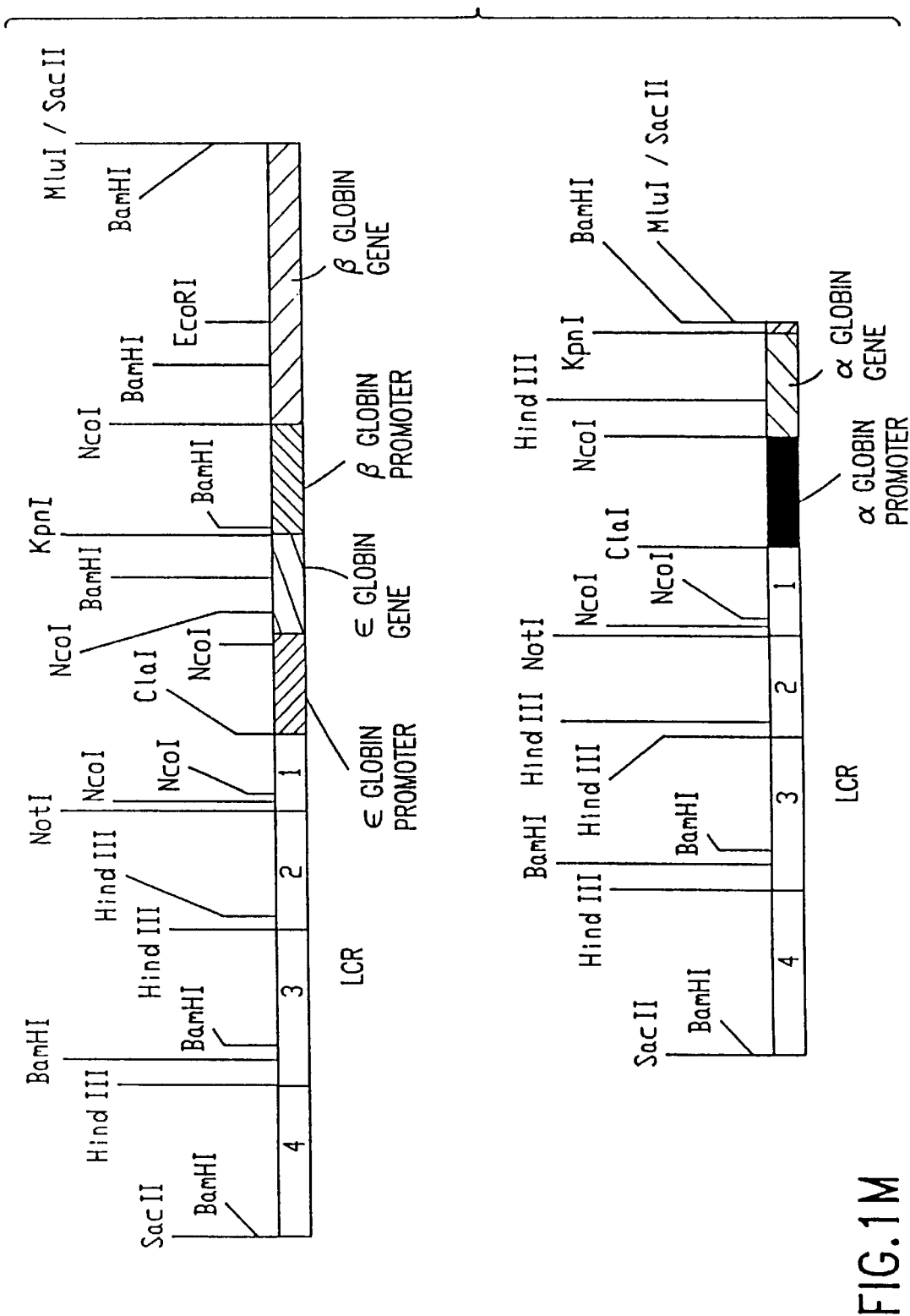
Figure 1N:
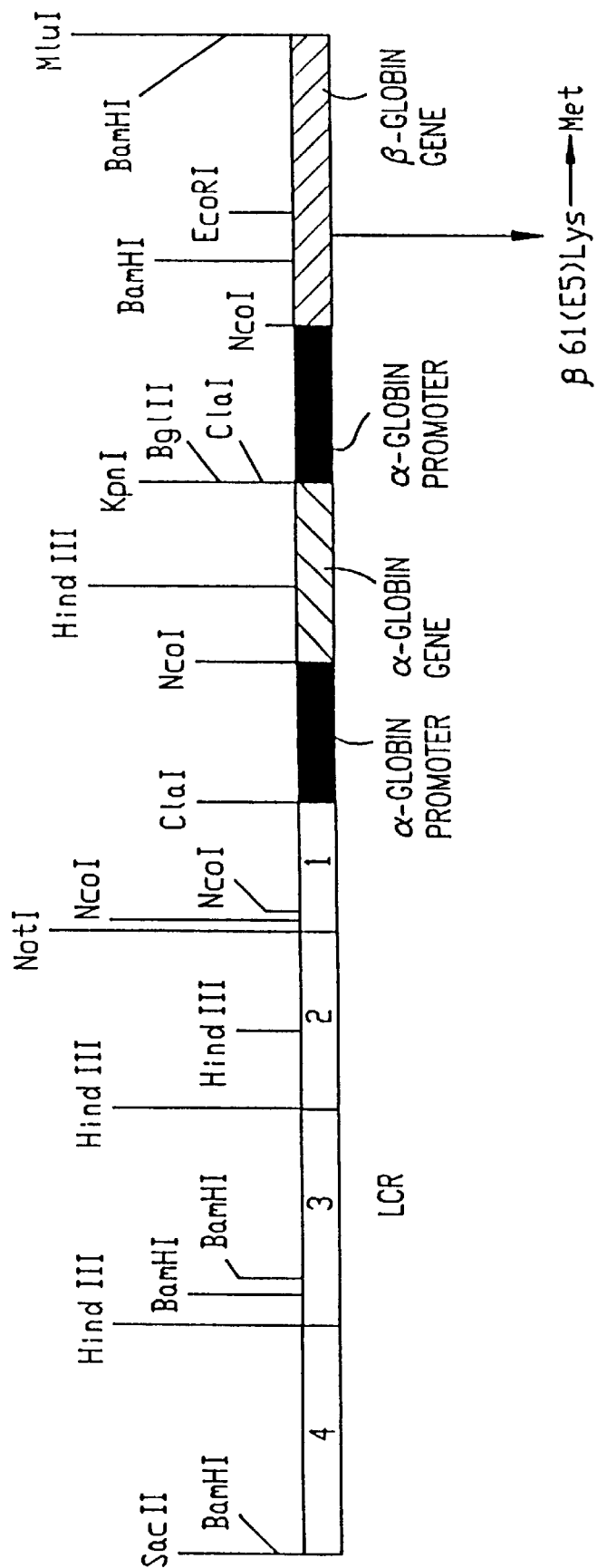
Figure 1P:
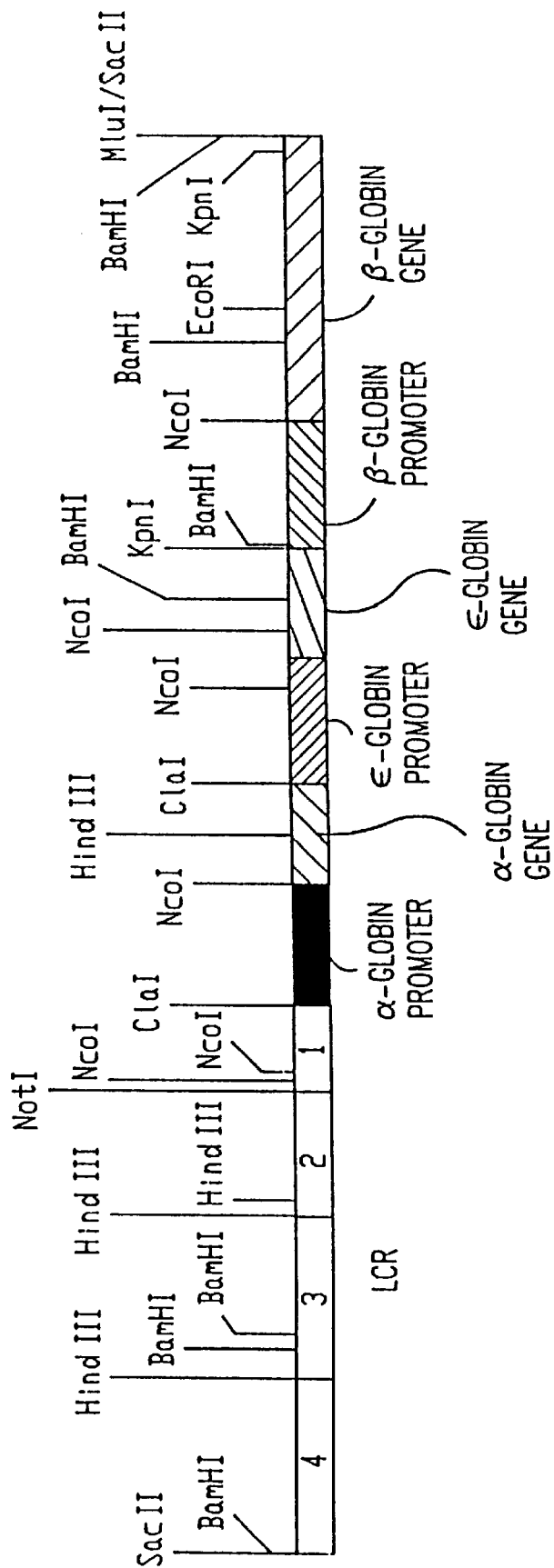
Figure 1Q:
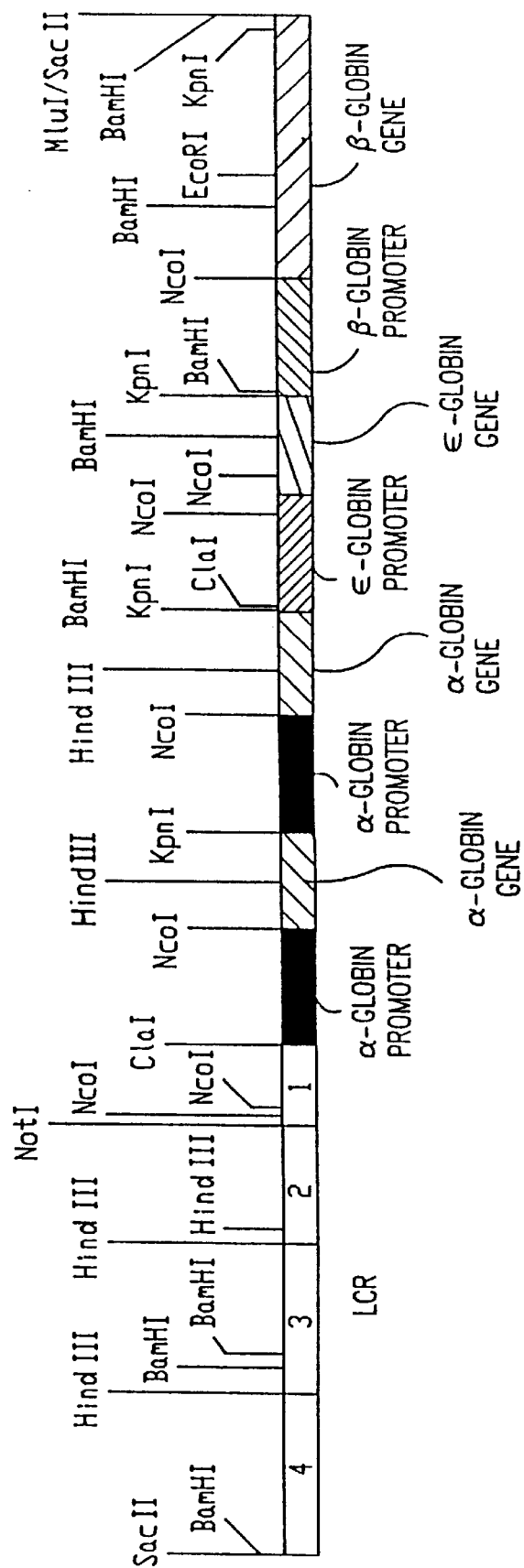
Figure 1R:
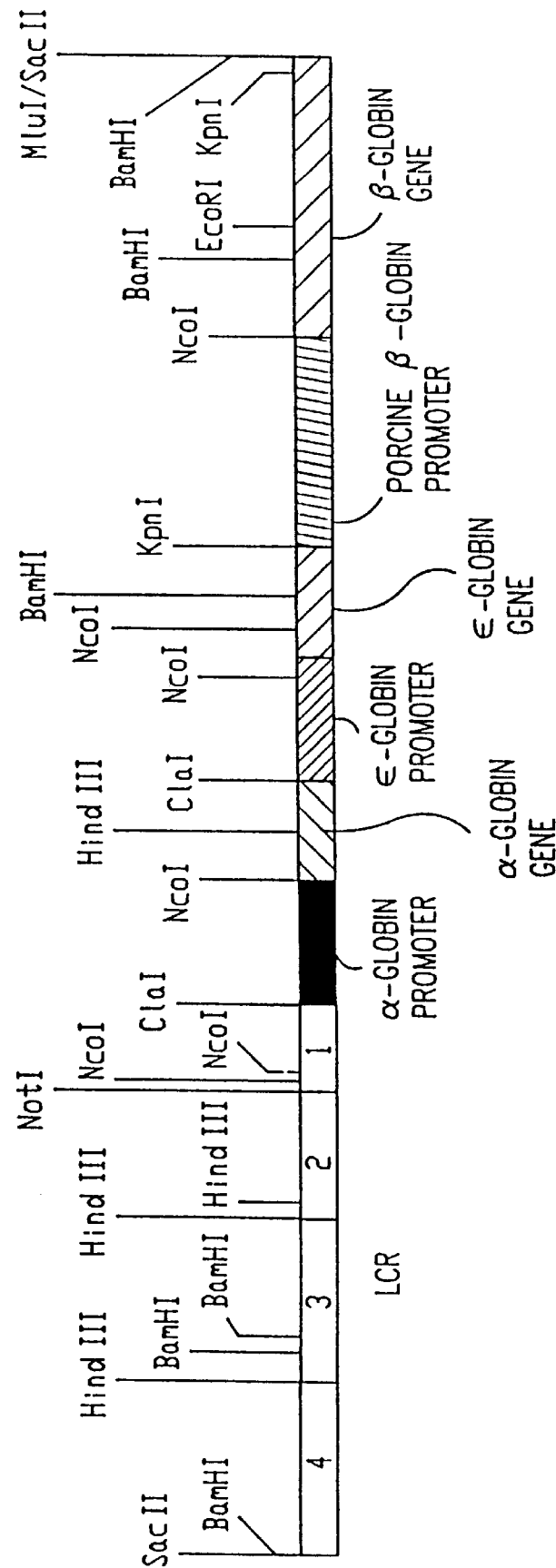
Figure 1S:
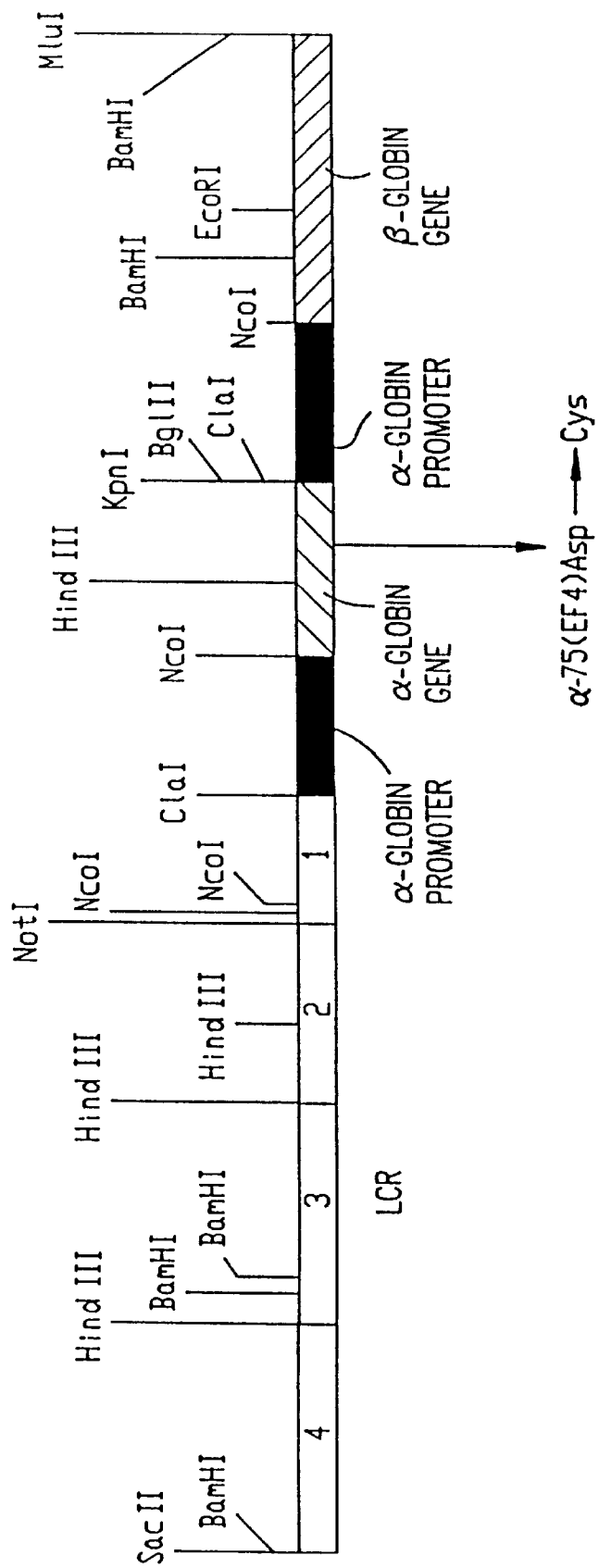
Figure 1T:
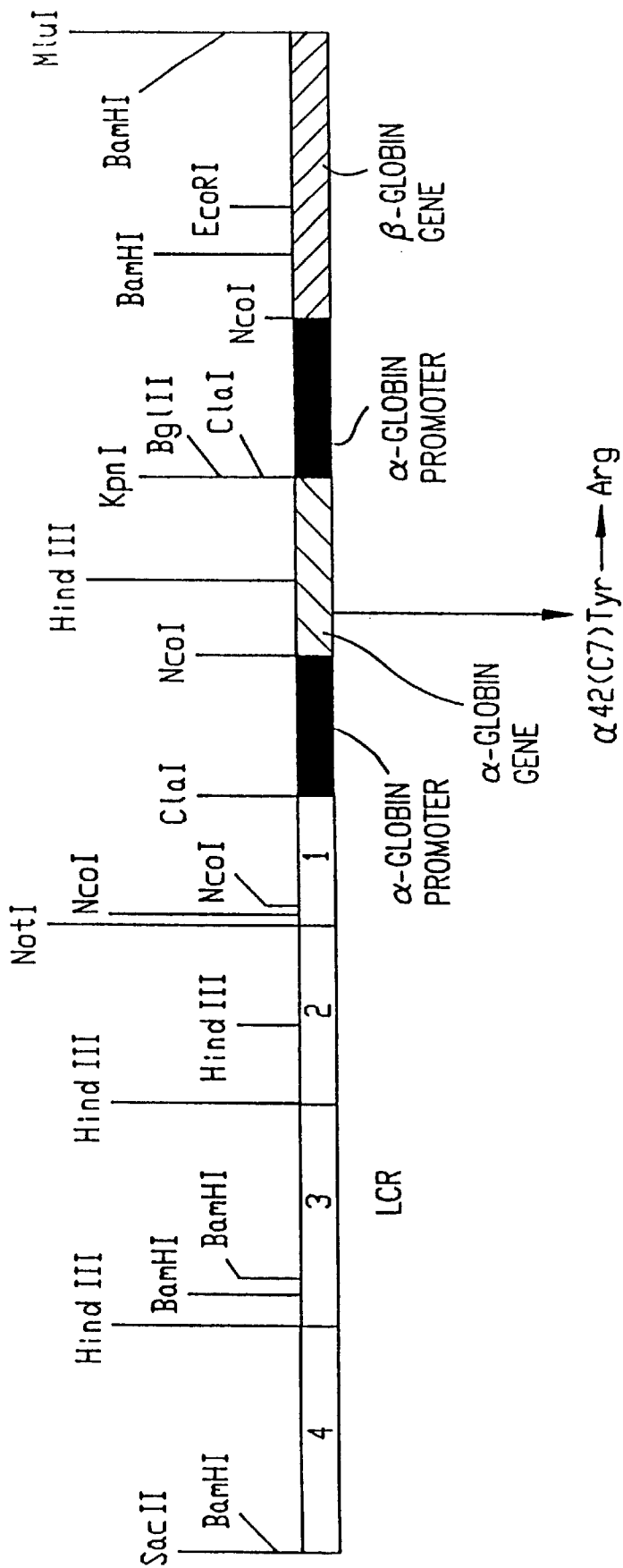
Figure 1U:
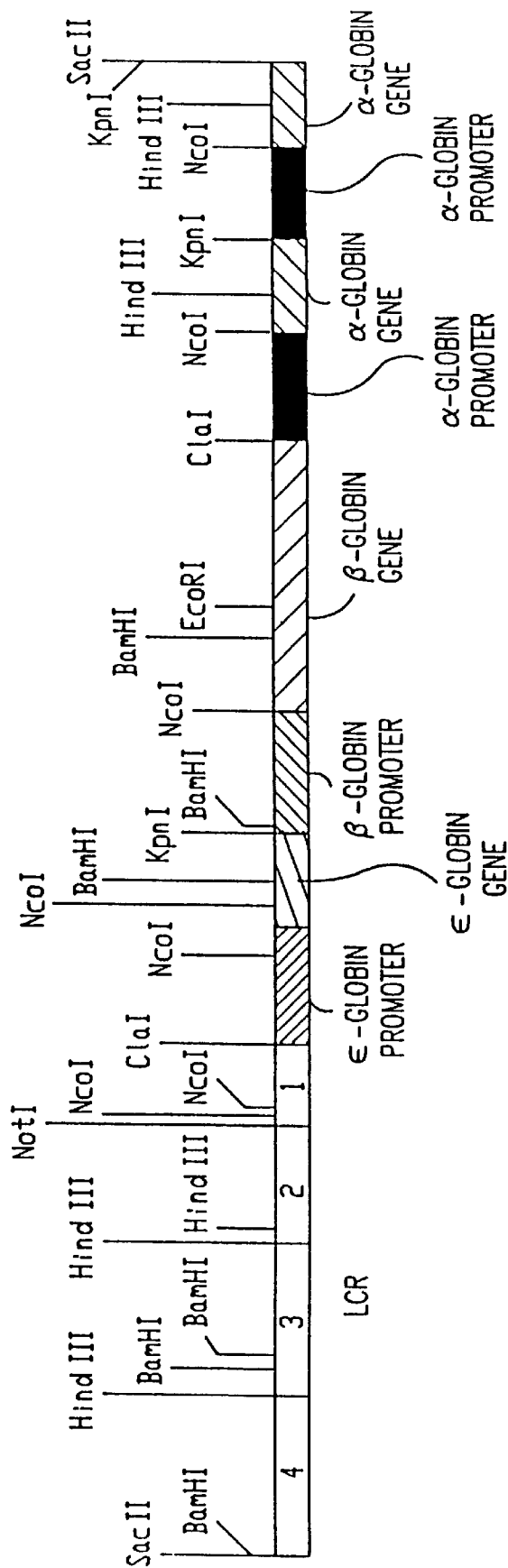
Figure 1V:
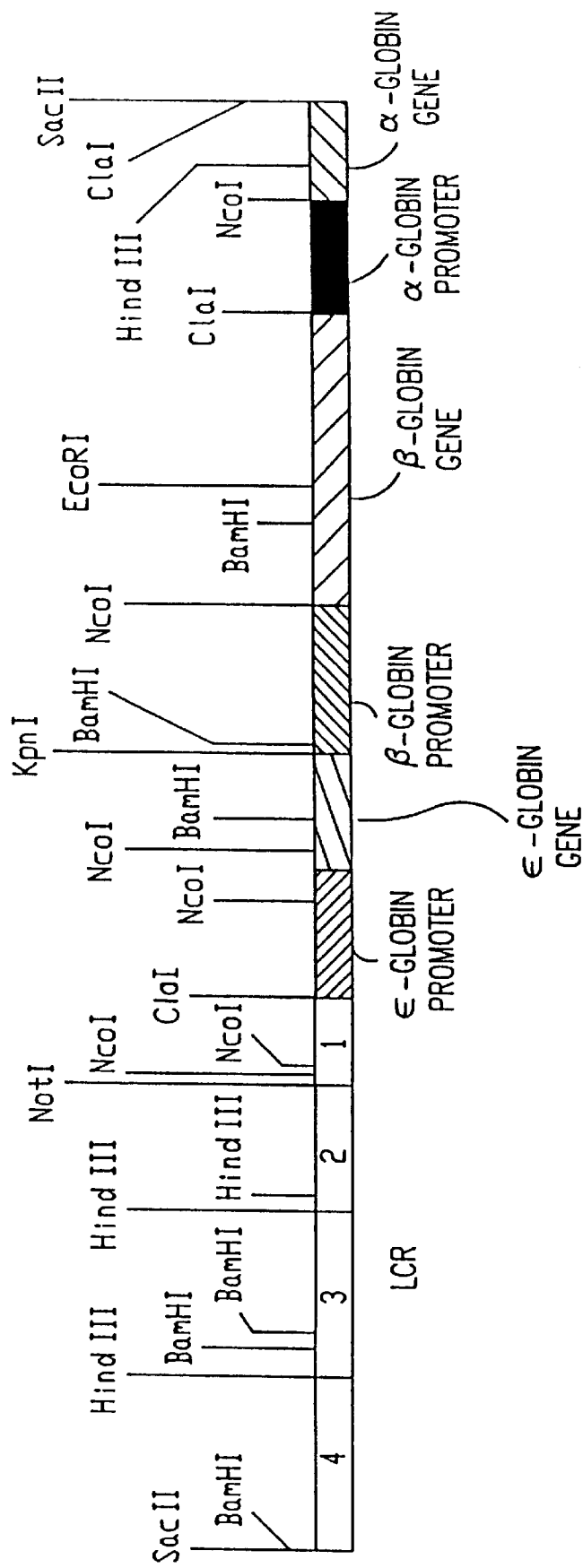
Figure 1W:
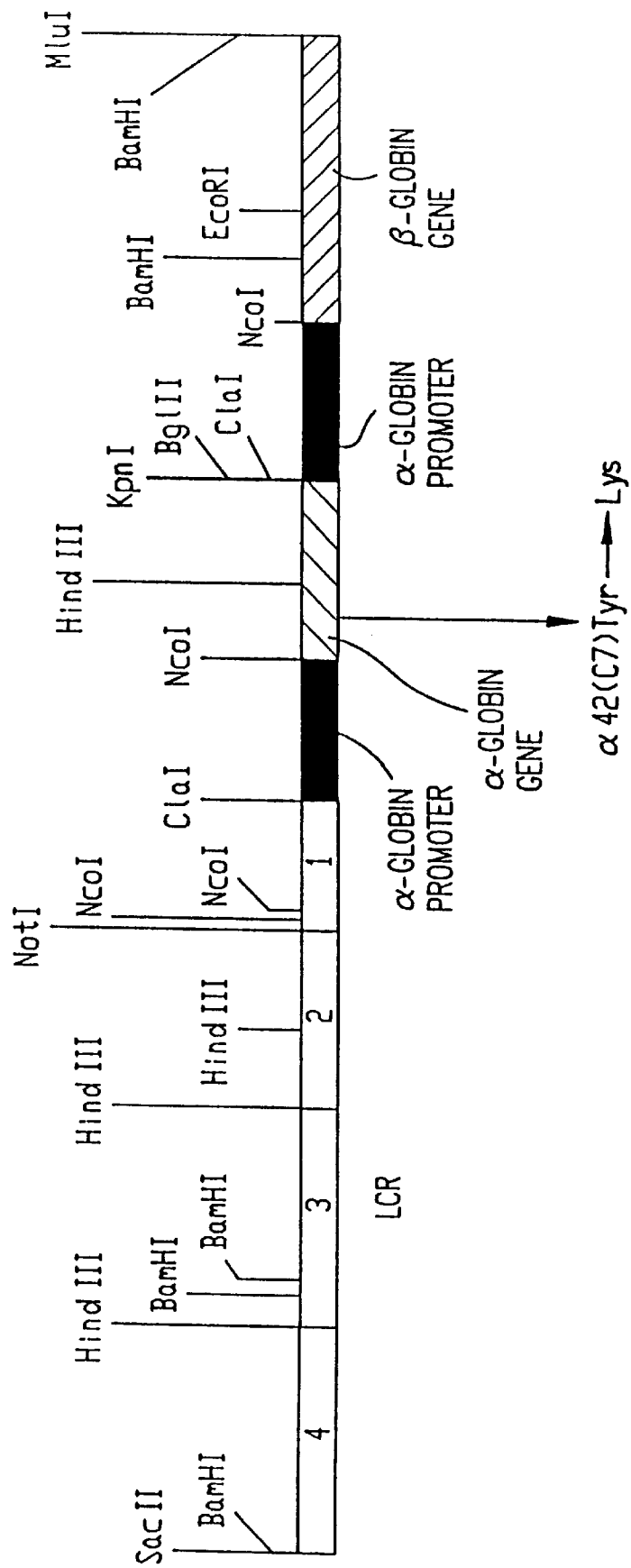
Figure 1X:
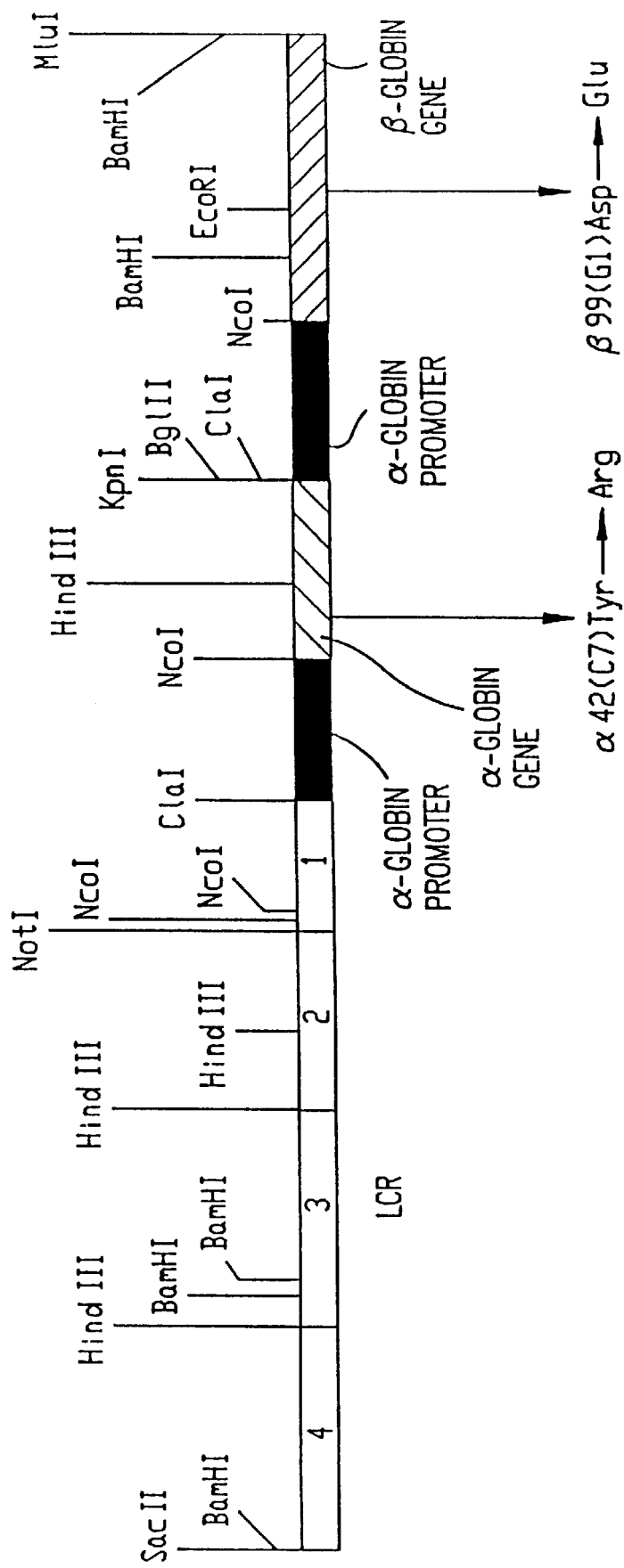
Figure 1Y:
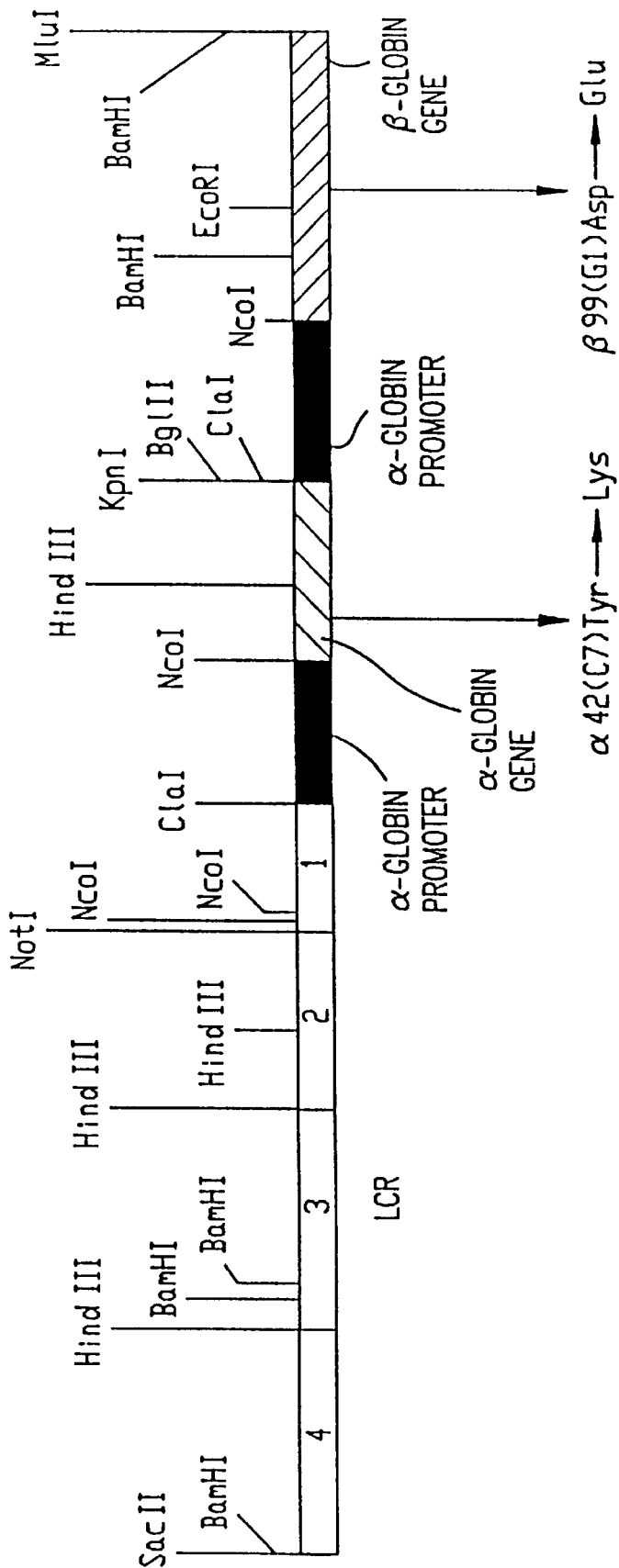

FIG. 1A. Construct ααβ (the "116 construct"); FIG. 1B. Construct αpβ (the "185" construct); FIG. 1C. Construct βpα (the "290" construct); FIG. 1D. Construct εpζβα; FIG. 1E. Construct ζpεαpβ; FIG. 1F. Construct αpβ carrying a β108 Asn→Asp mutation (the "hemoglobin Yoshizuka construct"); FIG. 1G. Construct αpβ carrying a β108 Asn→Lys mutation (the "hemoglobin Presbyterian construct"); FIG. 1H. Construct αpβ(Δα) coinjected with LCR α (the "285" construct); FIG. 1I. Construct αpβ carrying an α134 Thr→Cys mutation (the "227" construct); FIG. 1J. Construct αpβ carrying an α104 Cys→Ser mutation (the "227" construct), a β93 Cys→Ala mutation, and a β112 Cys→Val mutation (the "228" construct); FIG. 1K. Construct αpδ (the "263" construct); and FIG. 1L. Construct αpδ(Δα) coinjected with LCR α (the "274" construct); FIG. 1M. Construct LCR α coinjected with LCR εβ (the "240" construct); FIG. 1N. Construct αpβ carrying a β61 Lys→Met mutation (the "Hemoglobin Bologna" construct); FIG. 1O. Construct LCR εαβ (the "318" construct); FIG. 1P. Construct LCR αεβ (the "319" construct); FIG. 1Q. Construct LCR ααεβ (the "329" construct); FIG. 1R. Construct LCR αε($^{pig}$βp)β (the "339" construct); FIG. 1S. Construct αpβ carrying an α75 Asp→Cys mutation (the "340" construct); FIG. 1T. Construct αpβ carrying an α42 Tyr→Arg mutation (the "341" construct); FIG. 1U. Construct LCR εβαα (the "343" construct); FIG. 1V. Construct LCR εβα (the "347" construct); FIG. 1W. Construct αpβ carrying an α42 Tyr→Lys mutation; FIG. 1X. Construct αpβ carrying an α42 Tyr→Arg mutation; and a β99 Asp→Glu mutation; FIG. 1Y. Construct αpβ carrying an α42 Tyr→Lys mutation; and a β99 Asp→Glu mutation.

Figure 2:
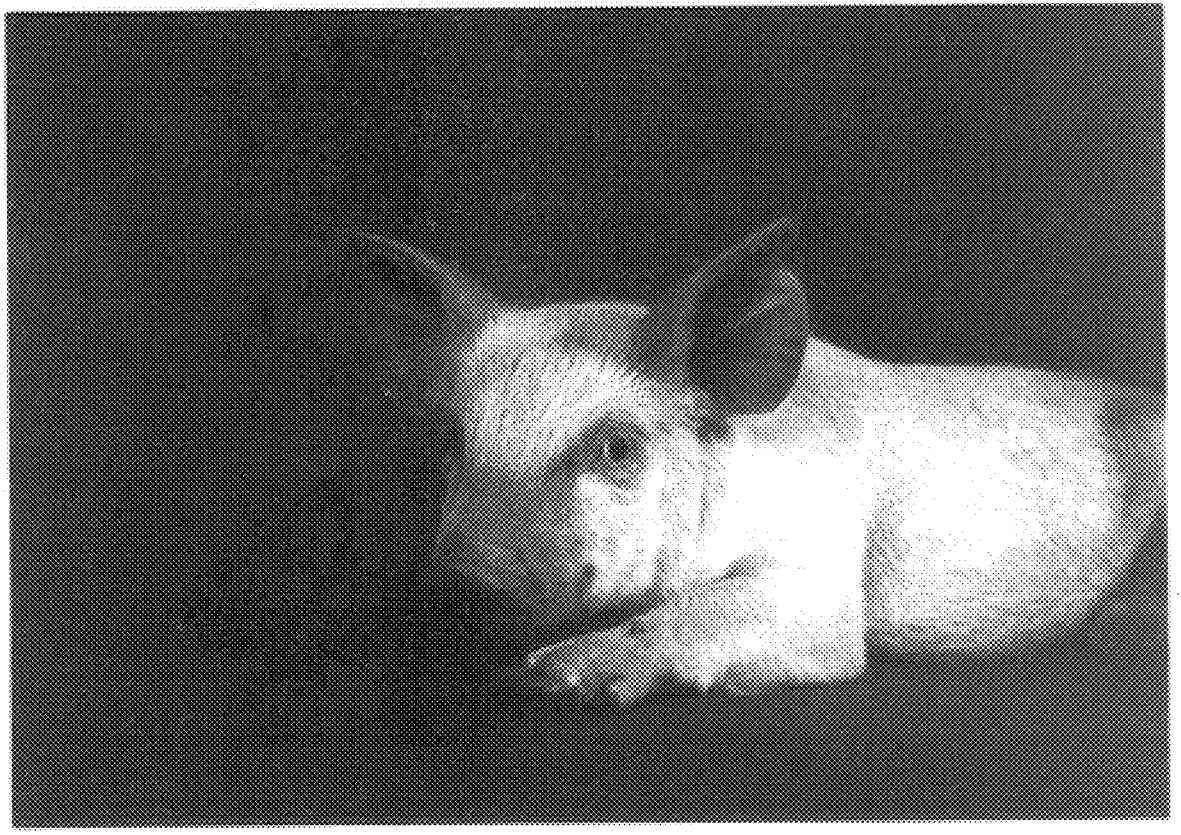

FIG. 2. Transgenic pig.

Figure 3A:
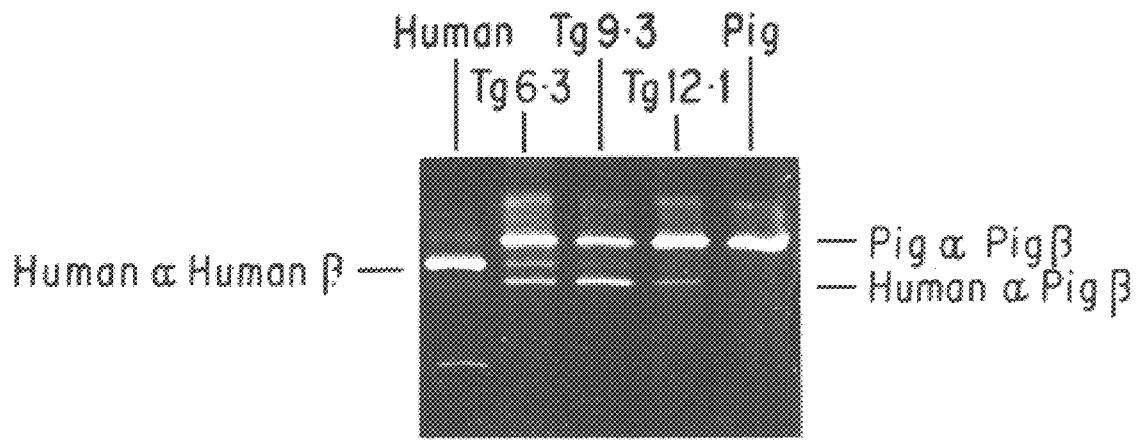
Figure 3B:
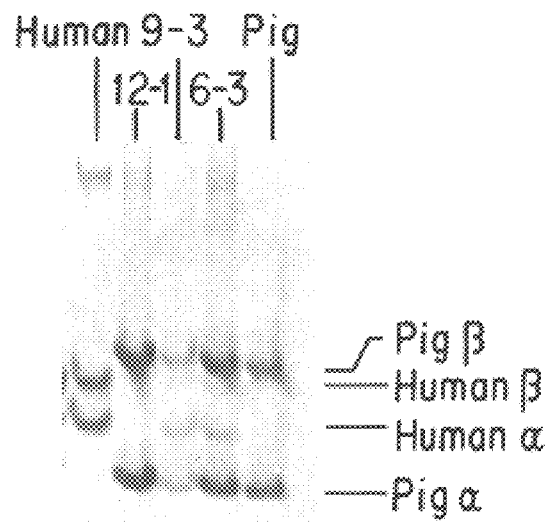

FIG. 3A and 3B. Demonstration of human hemoglobin expression in transgenic pigs. FIG. 3A Isoelectric focusing gel analysis. FIG. 3B Triton-acid urea gel of hemolysates of red blood cells representing human blood (lane 1); blood from transgenic pig 12-1 (lane 2), 9-3 (lane 3), and 6-3 (lane 4); and pig blood (lane 5) shows under-expression of human β globin relative to human α globin in the transgenic animals.

Figure 4A:
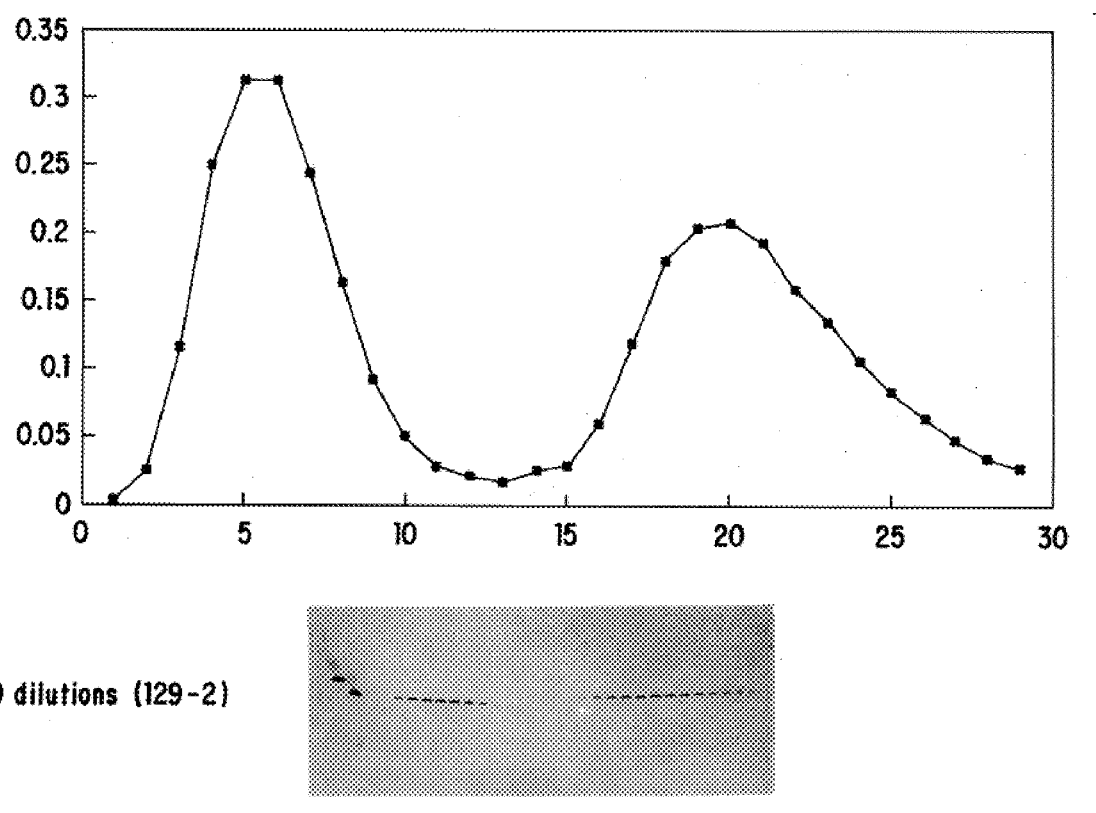
Figure 4B:
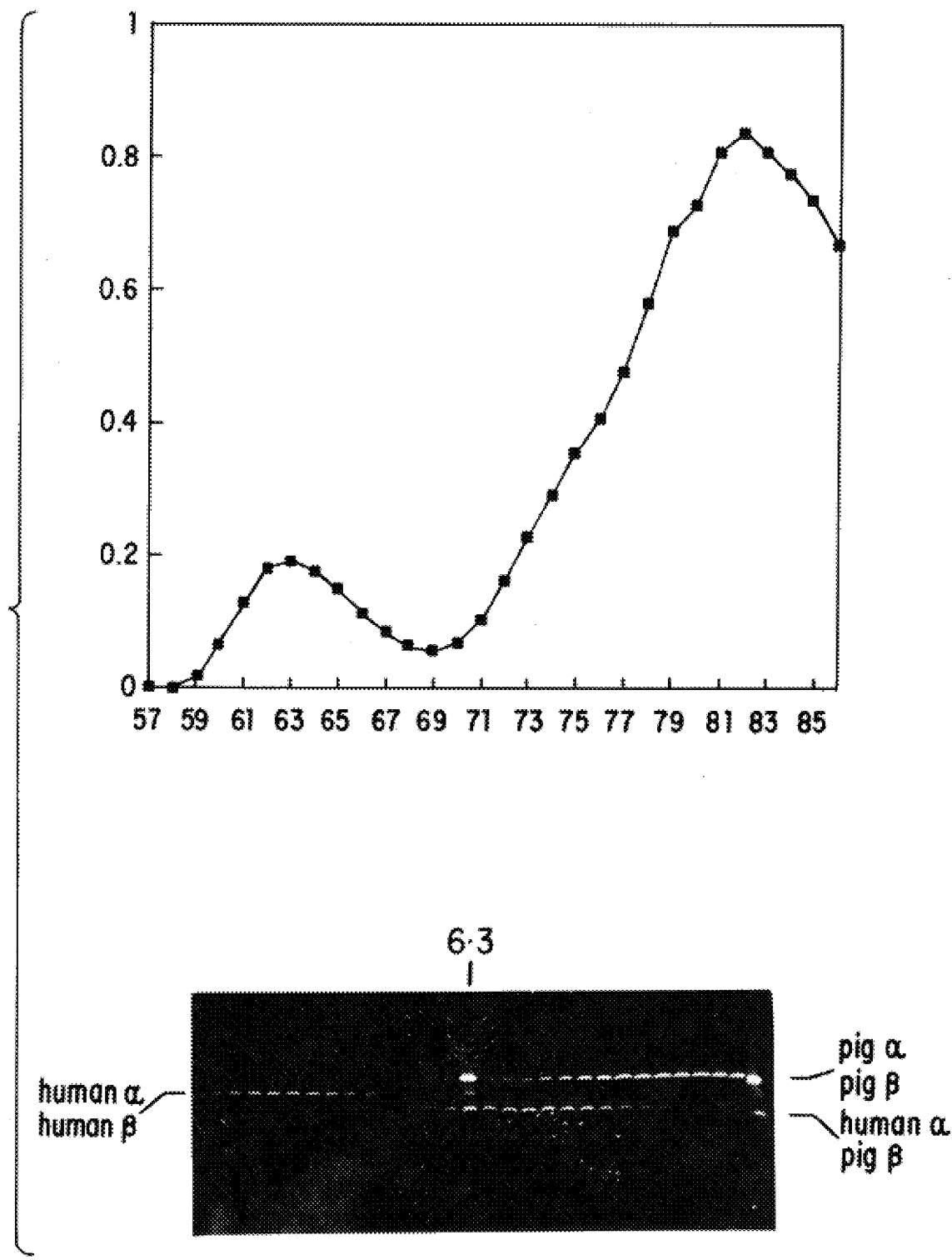
Figure 4C:
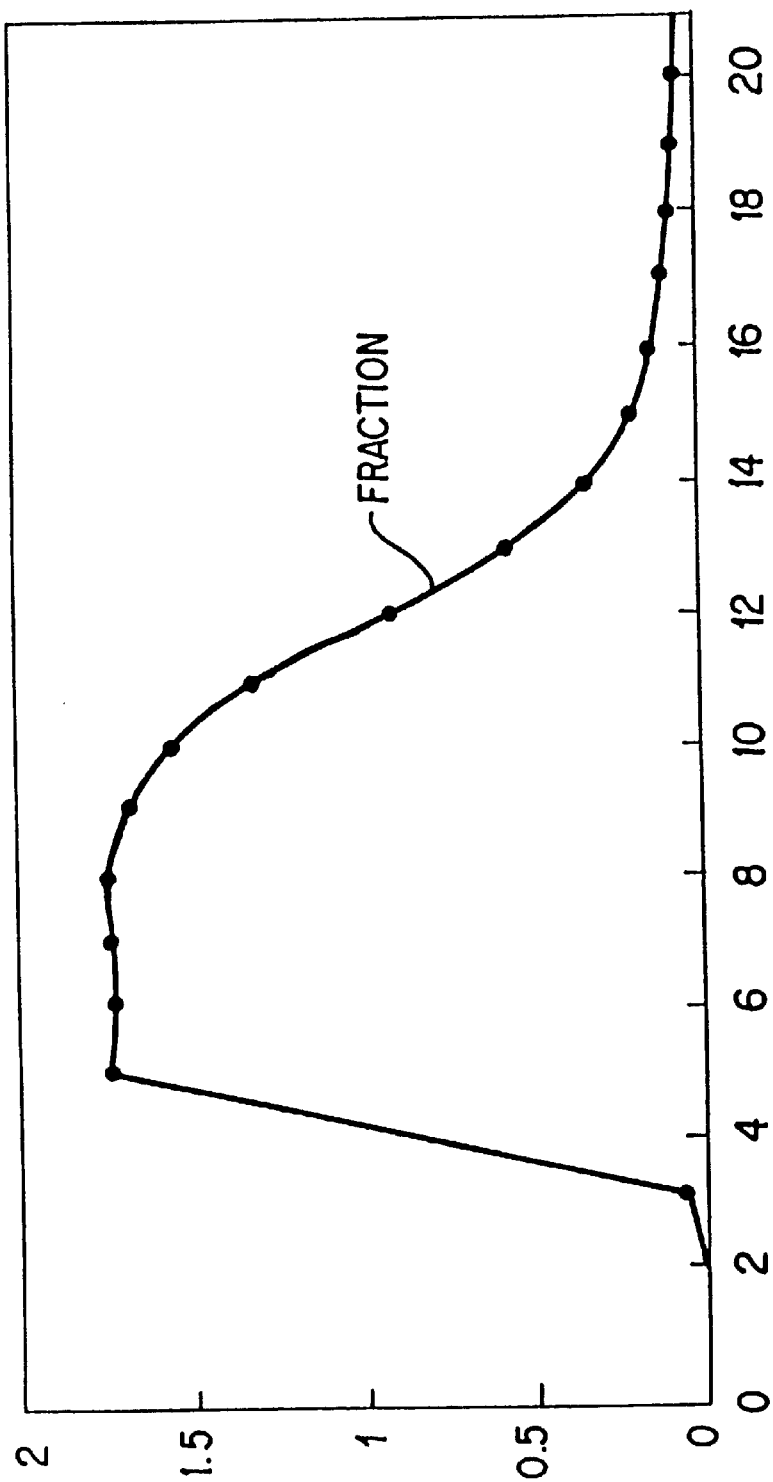
Figure 4D:
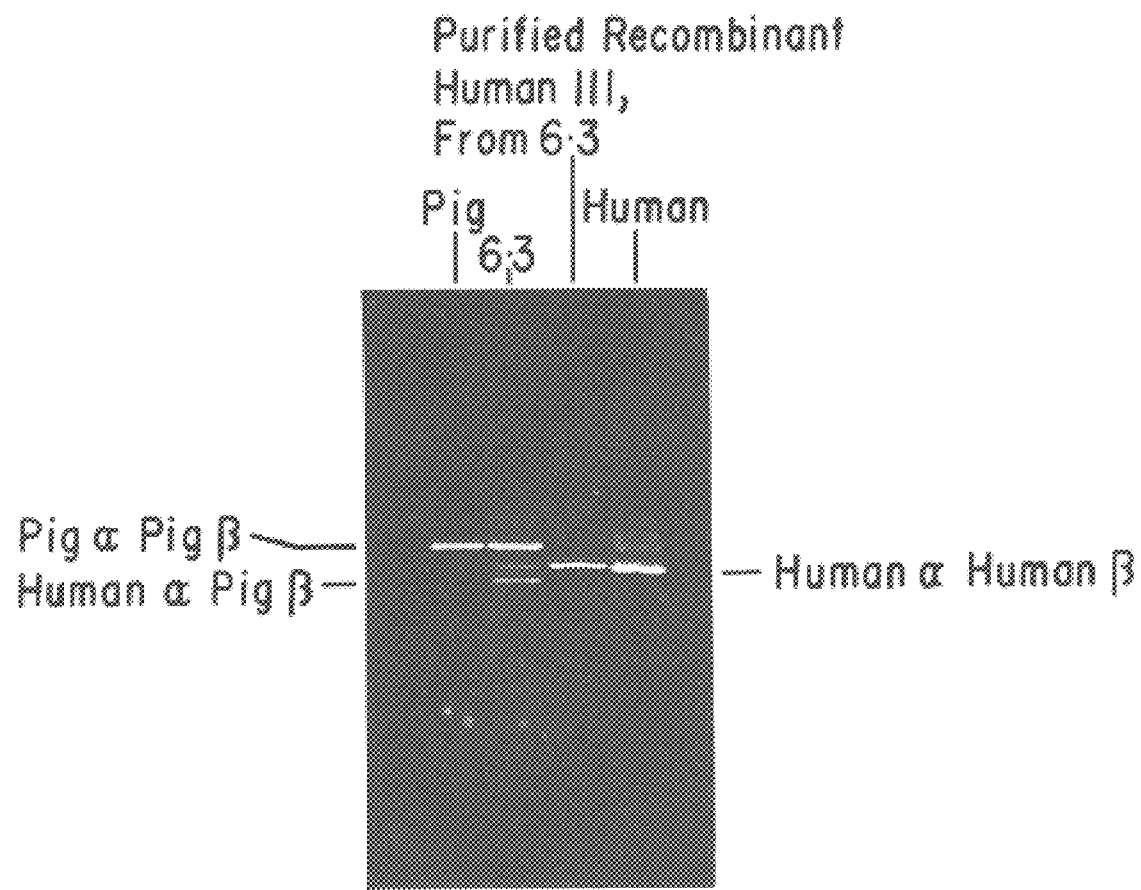

FIG. 4A, 4B, 4C and 4D. Separation of human hemoglobin and pig hemoglobin by DEAE chromatography. FIG. 4A. Hemolyzed mixture of human and pig red blood cells; FIG. 4B. Hemolysate of red blood cells collected from transgenic pig 6-3. FIG. 4C. Human and mouse hemoglobin do not separate by DEAE chromatography under these conditions. FIG. 4D. Isoelectric focusing of human hemoglobin purified from pig hemoglobin.

Figure 5:
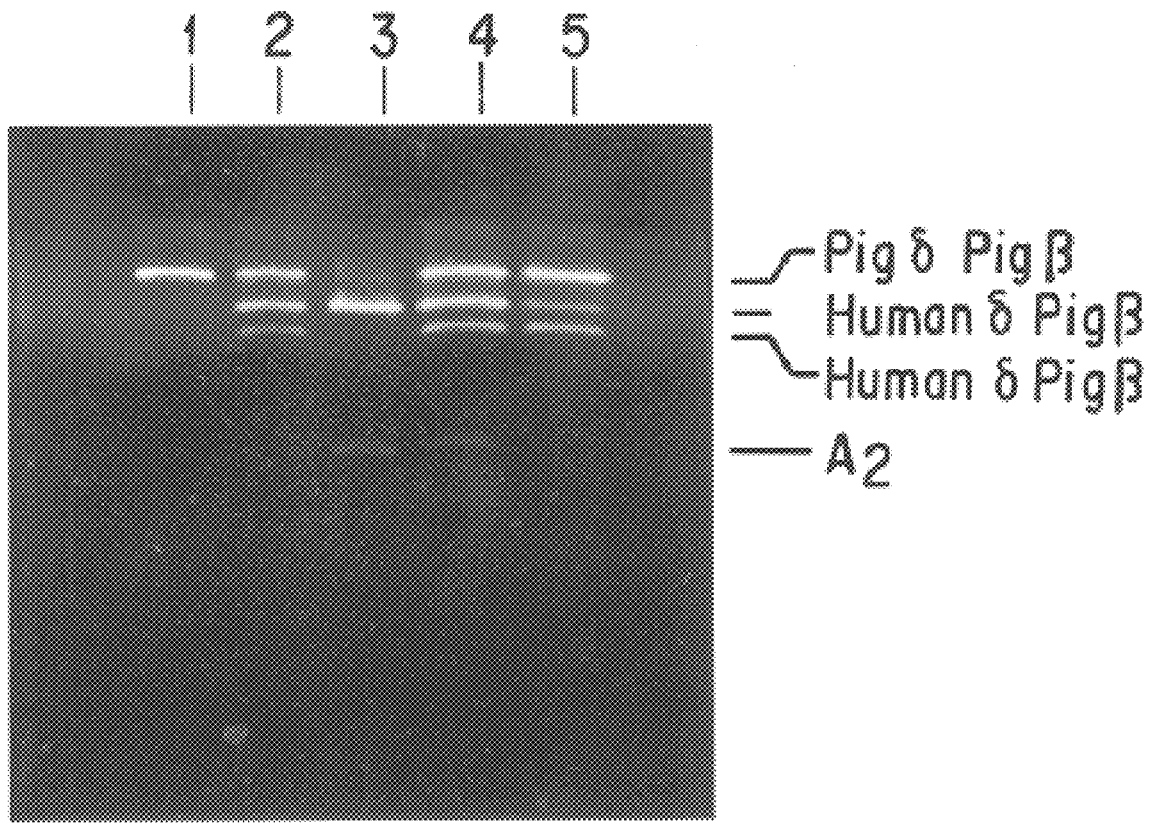

FIG. 5. Isoelectric focussing gel of reassociated pig hemoglobin (lane 1); reassociated pig/human hemoglobin mixture (lanes 2 and 4); reassociated human hemoglobin (lane 3); and transgenic pig hemoglobin (lane 5).

Figure 6:
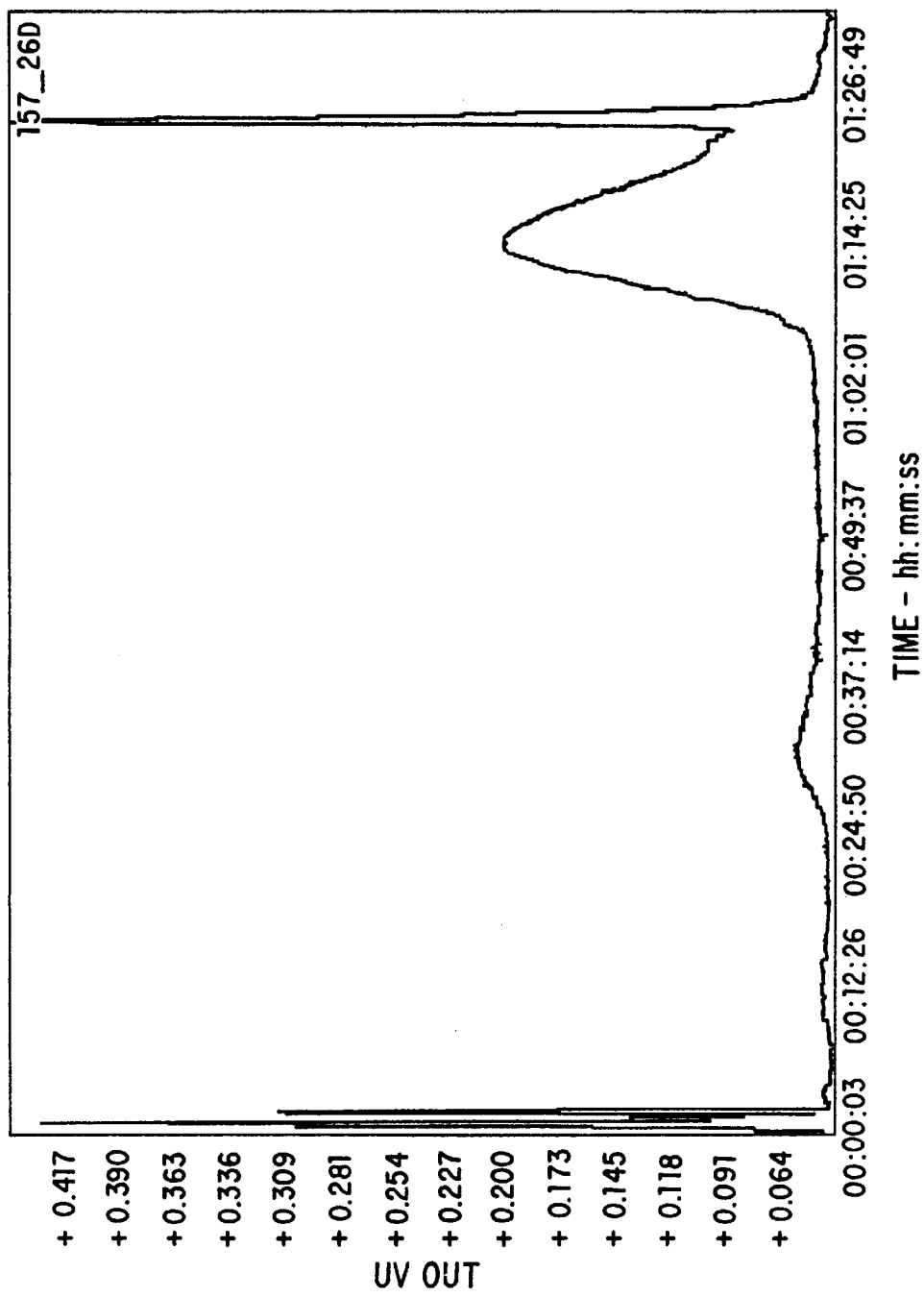

FIG. 6. Separation of human hemoglobin by QCPI chromatography.

Figure 7A:
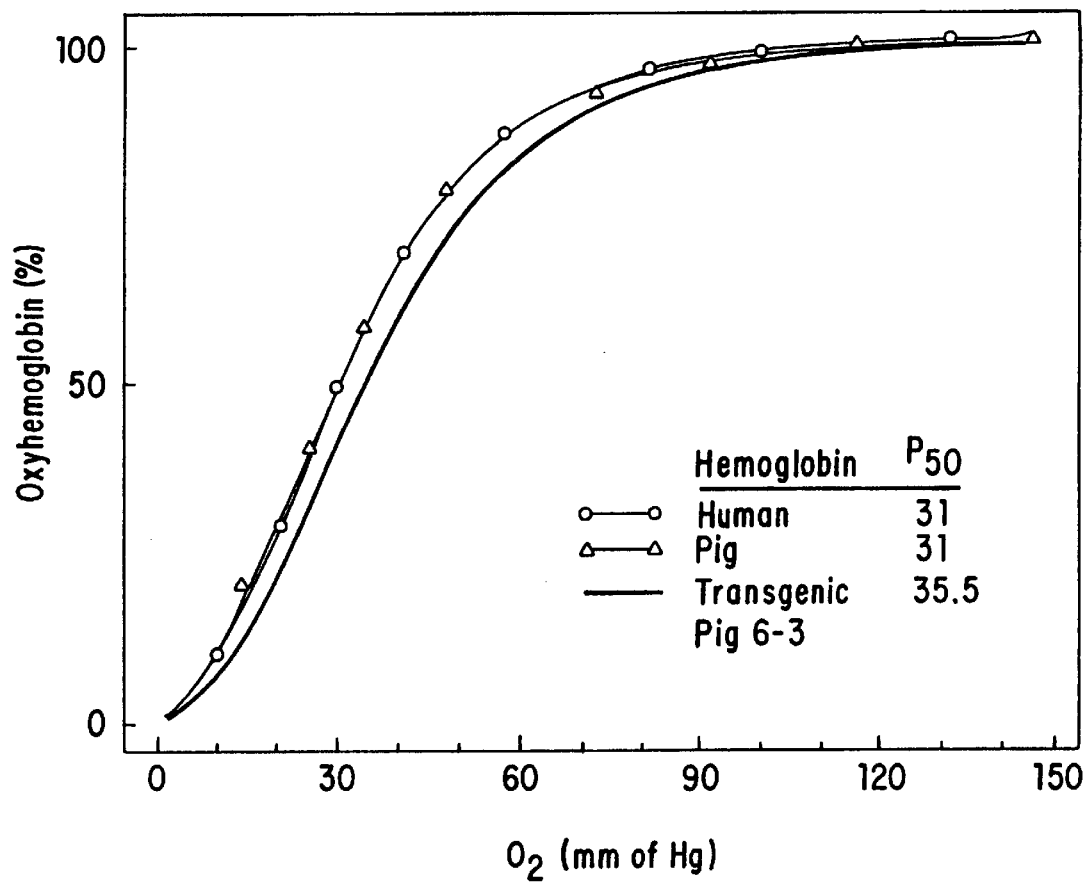
Figure 7B:
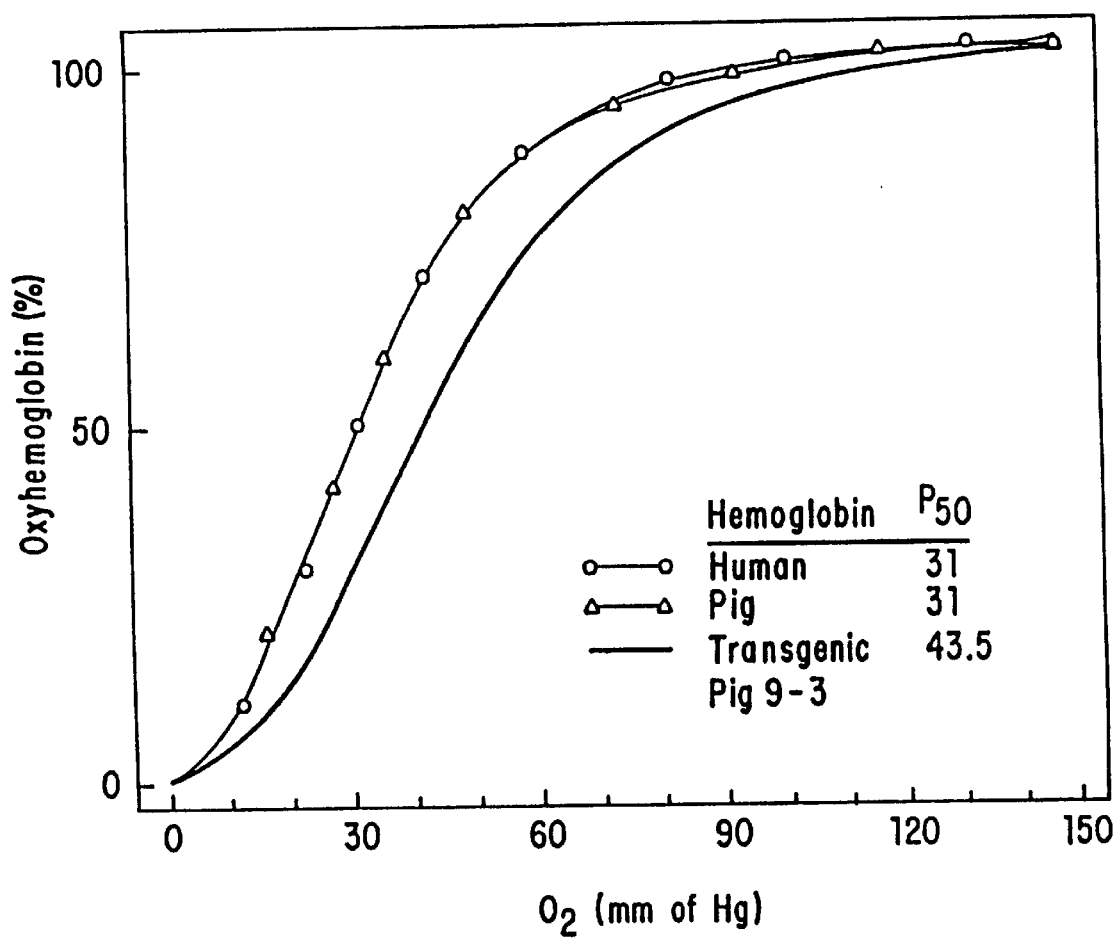
Figure 10:
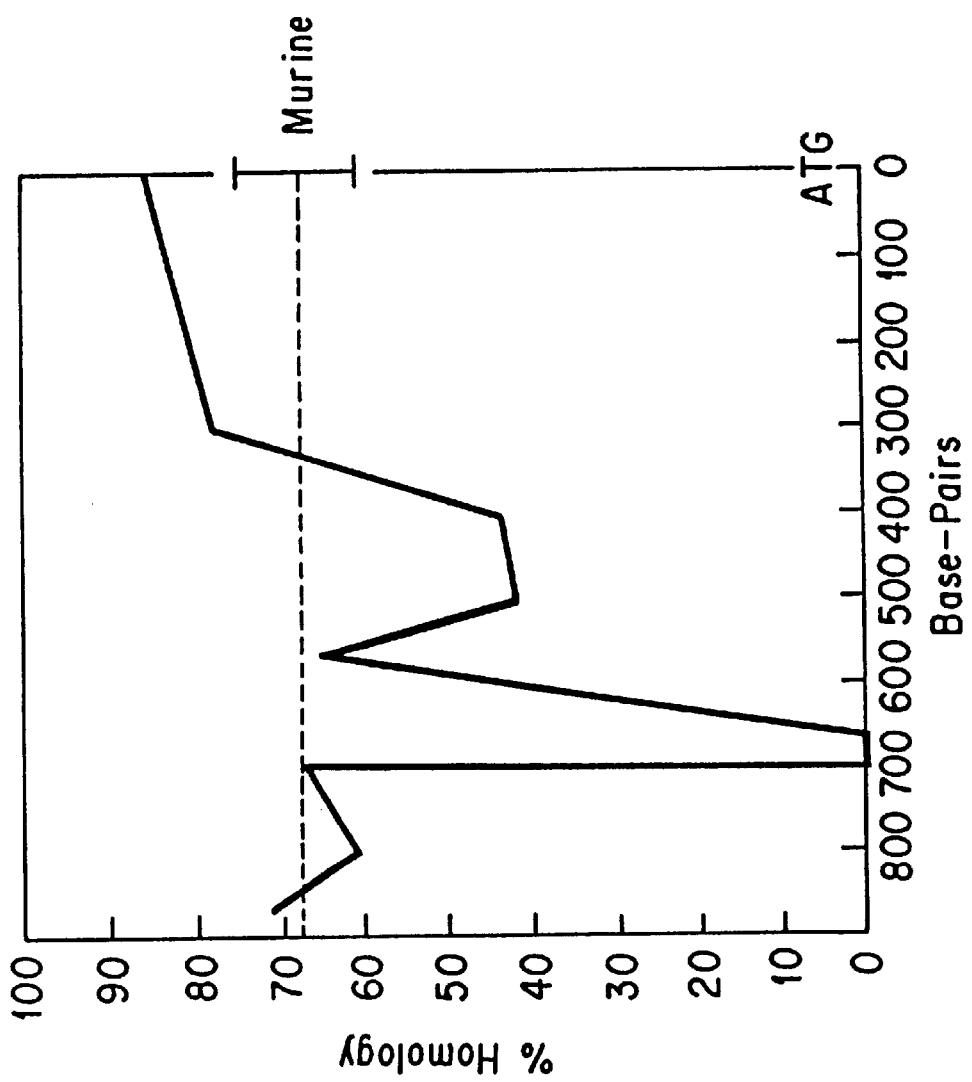
Figure 11:
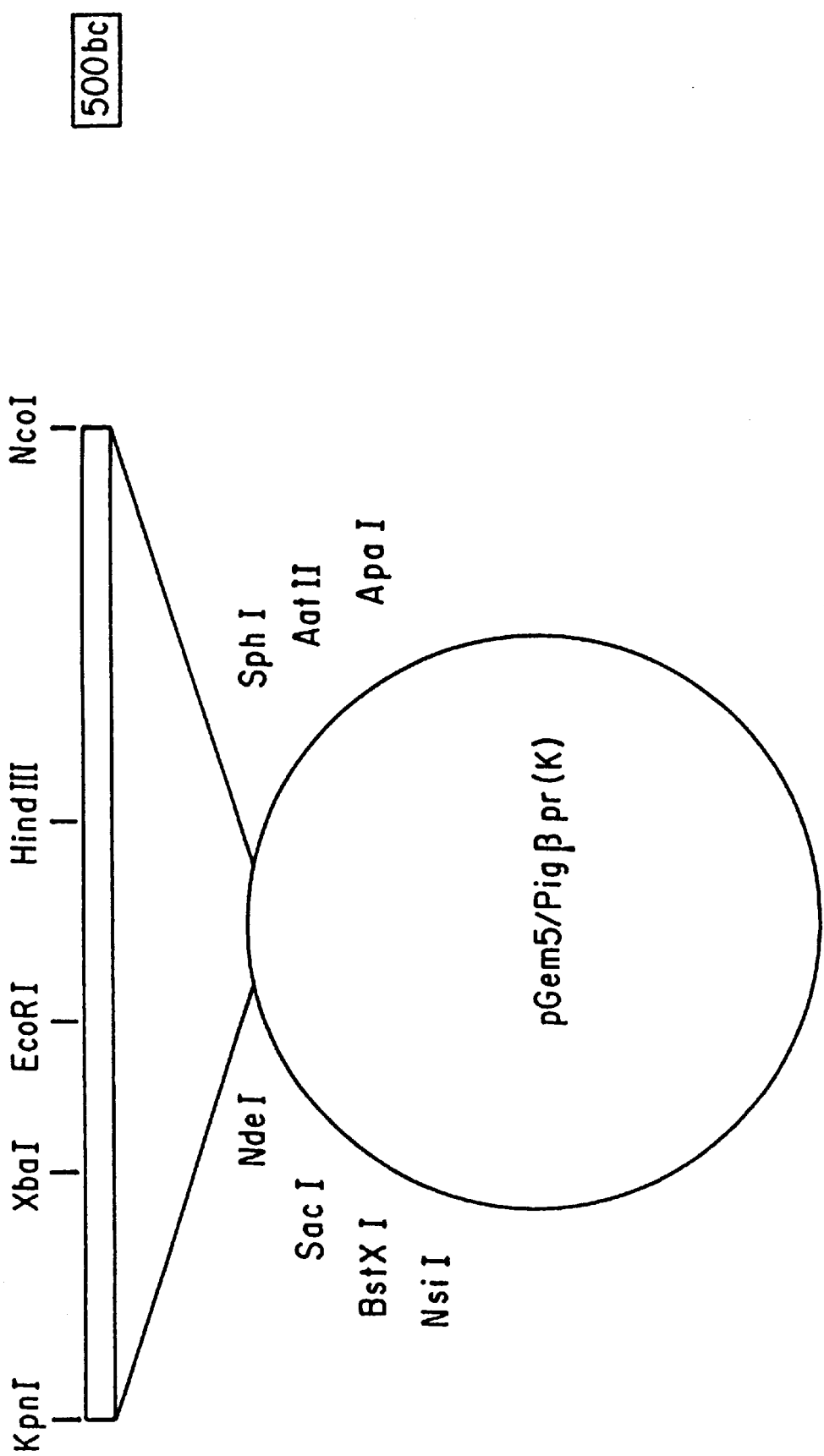

FIG. 7. Oxygen affinity of transgenic hemoglobin.

FIG. 8. DNA sequence (SEQ ID NO:1) of the pig adult beta globin gene regulatory region, including the promoter region. Sequence extending to 869 base pairs upstream of the ATG initiator codon (boxed) of the pig beta globin gene is shown. The position of the initiation of mRNA, the cap site, is indicated by an arrow. The sequences corresponding to GATA transcription factor binding sites are underlined.

FIG. 9. Comparison of pig (SEQ ID NO:1) (top) and human (SEQ ID NO:2 & 3) (bottom) beta globin regulatory sequences. Differences in the two sequences are marked by asterisks.

Figure 10:
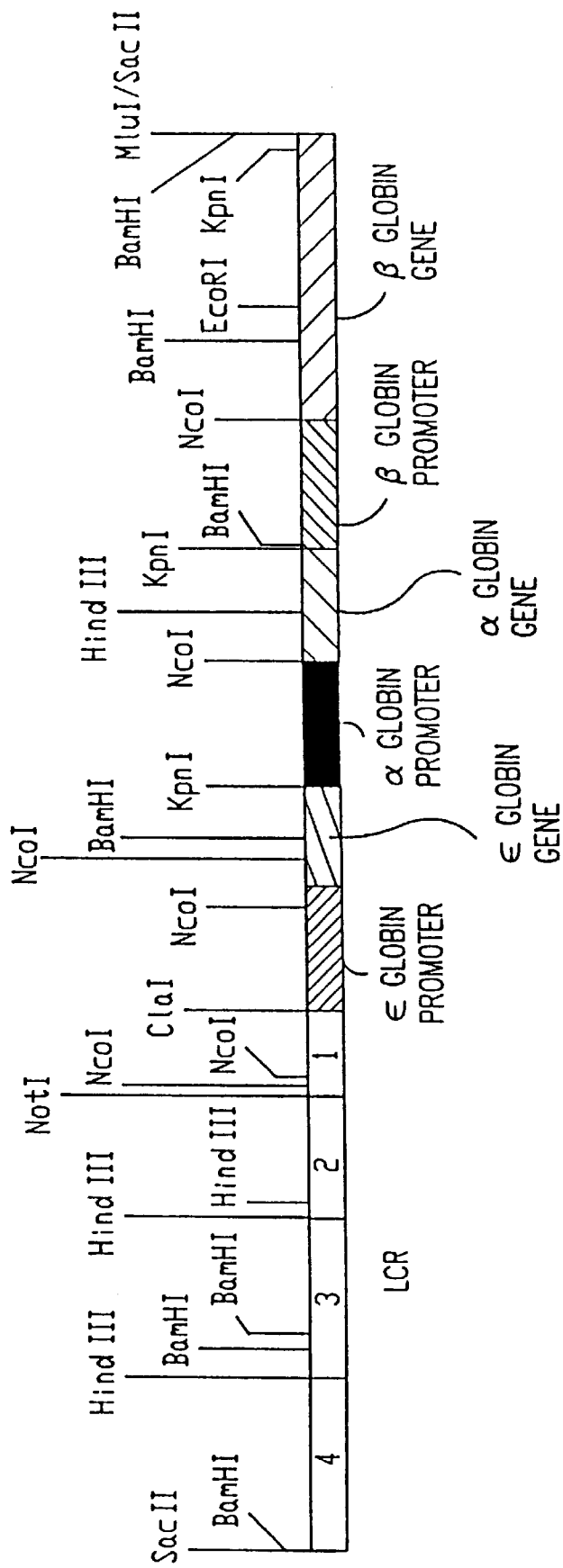

FIG. 10. Graph depicting the percent homology between pig and human adult beta globin gene regulatory sequences, with base pair distance from the initiator codon mapped on the abscissa. A comparison of mouse and human sequences is also shown (dotted line with error bar).

Figure 11:
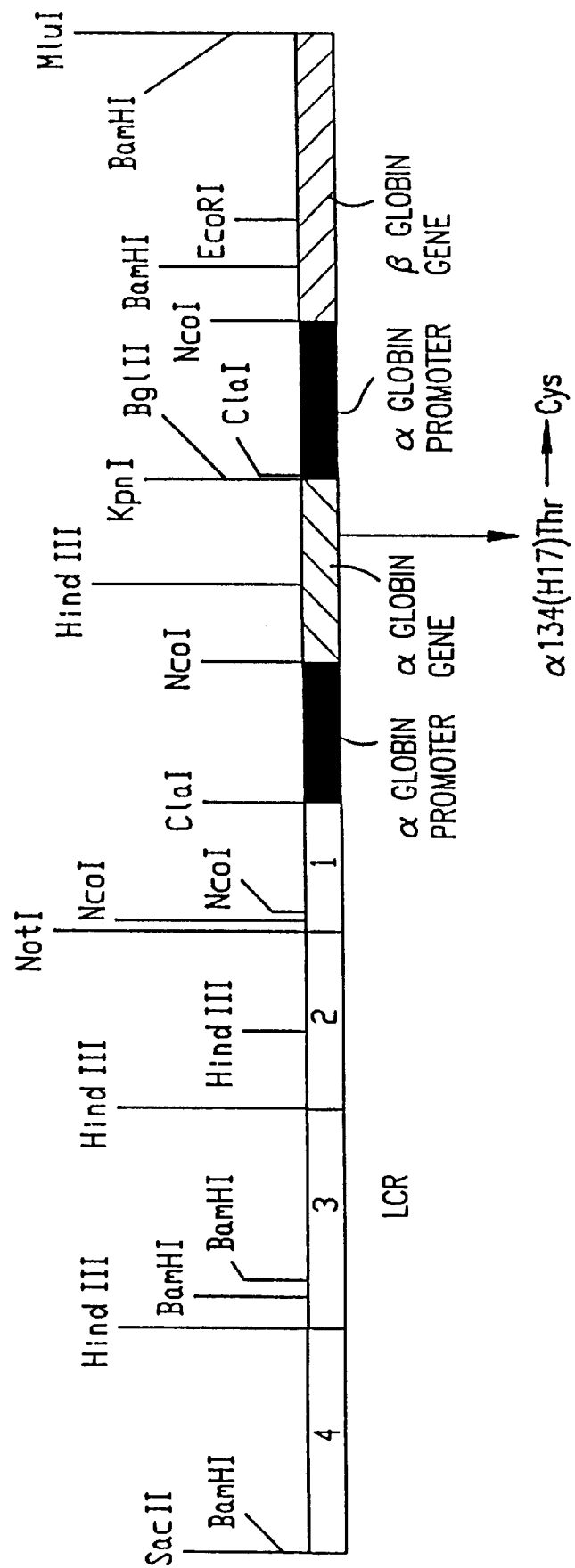

FIG. 11. Map of plasmid pgem5/PigβPr(k) which contains the DNA sequence depicted in FIG. 8.

Figure 12:
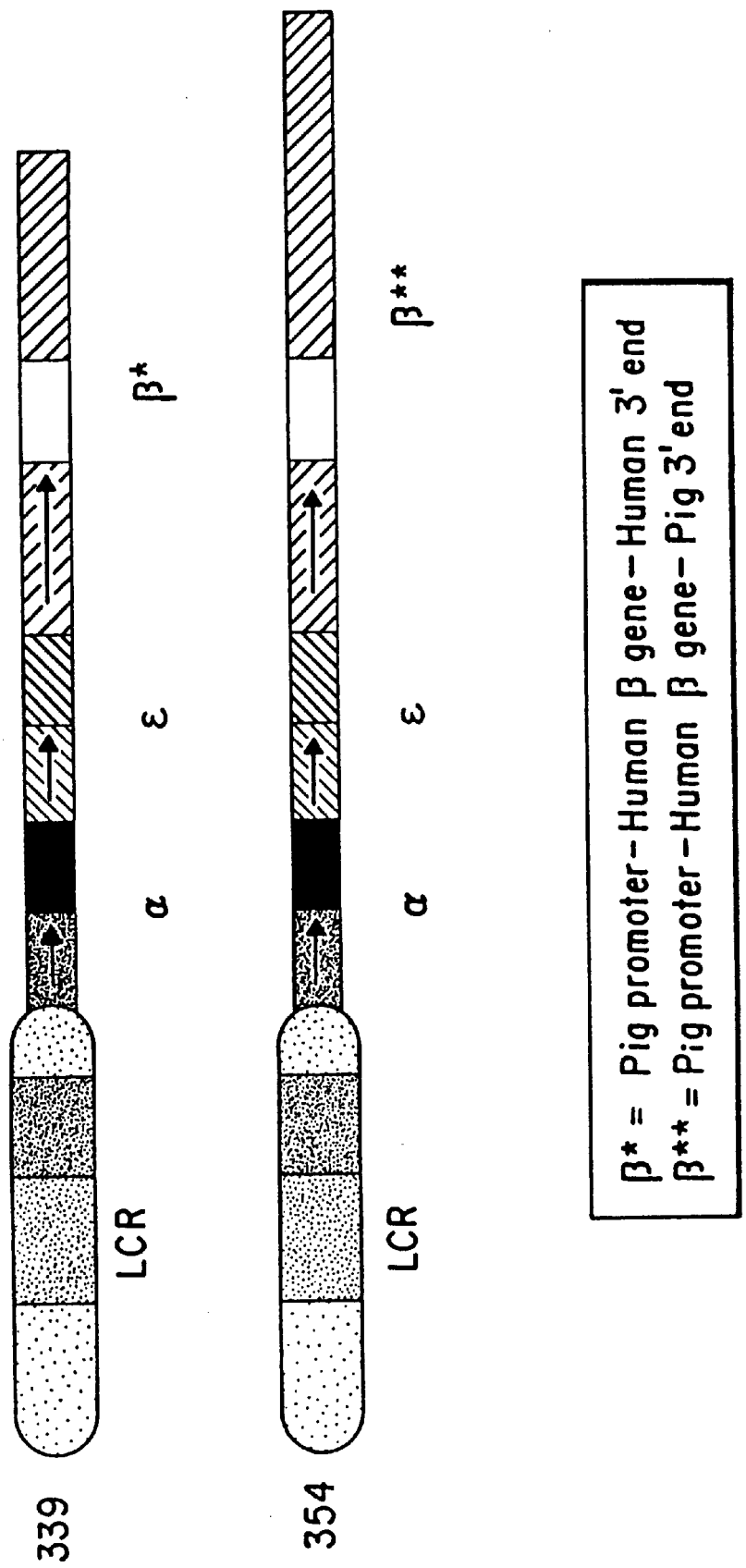

FIG. 12. Representation of the 339 and 354 cassettes for the production of human hemoglobin in transgenic pigs.

Figure 13:
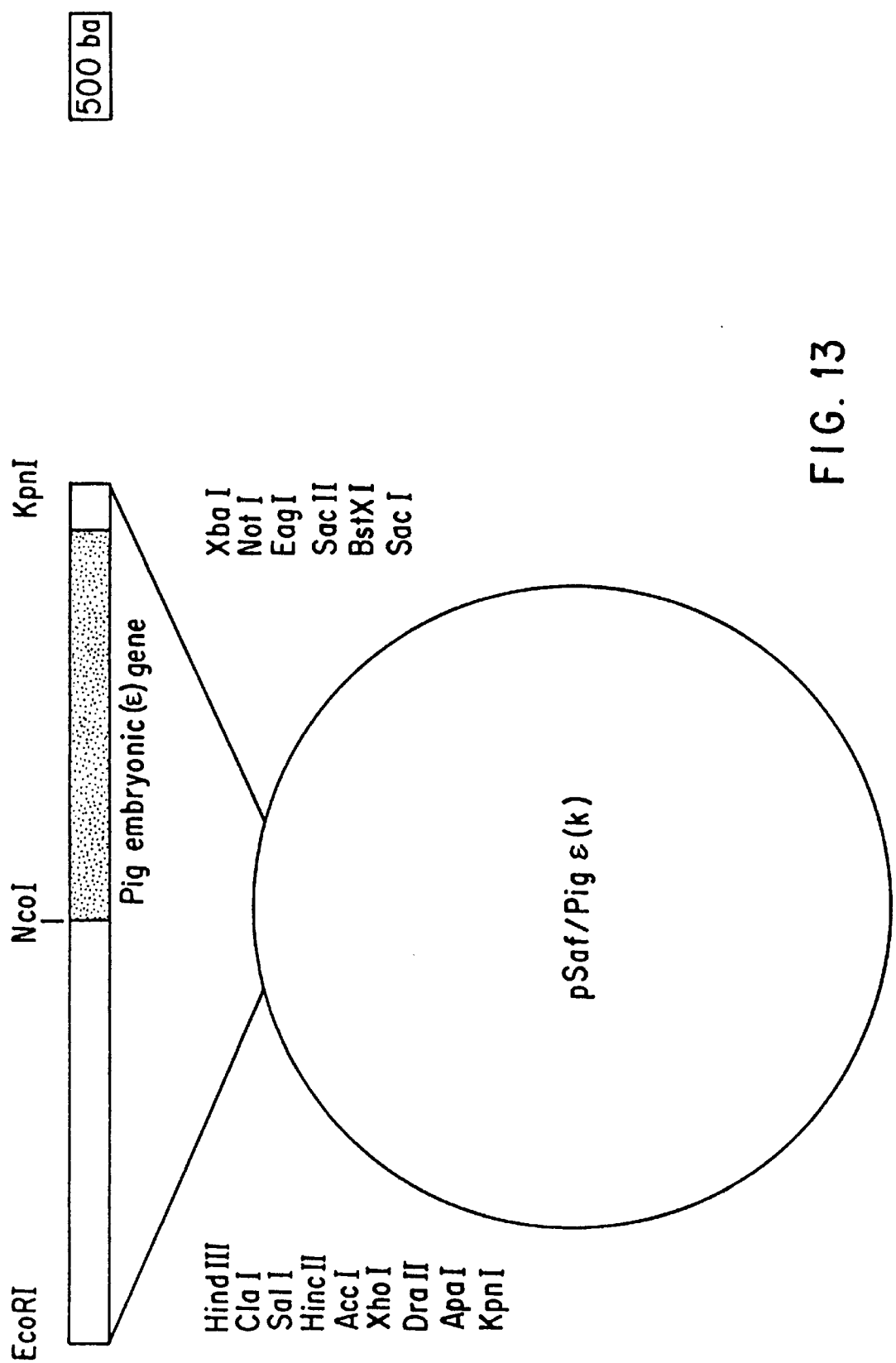

FIG. 13. Map of plasmid pSaf/Pigε(k), containing the pig ε gene.

Figure 14:
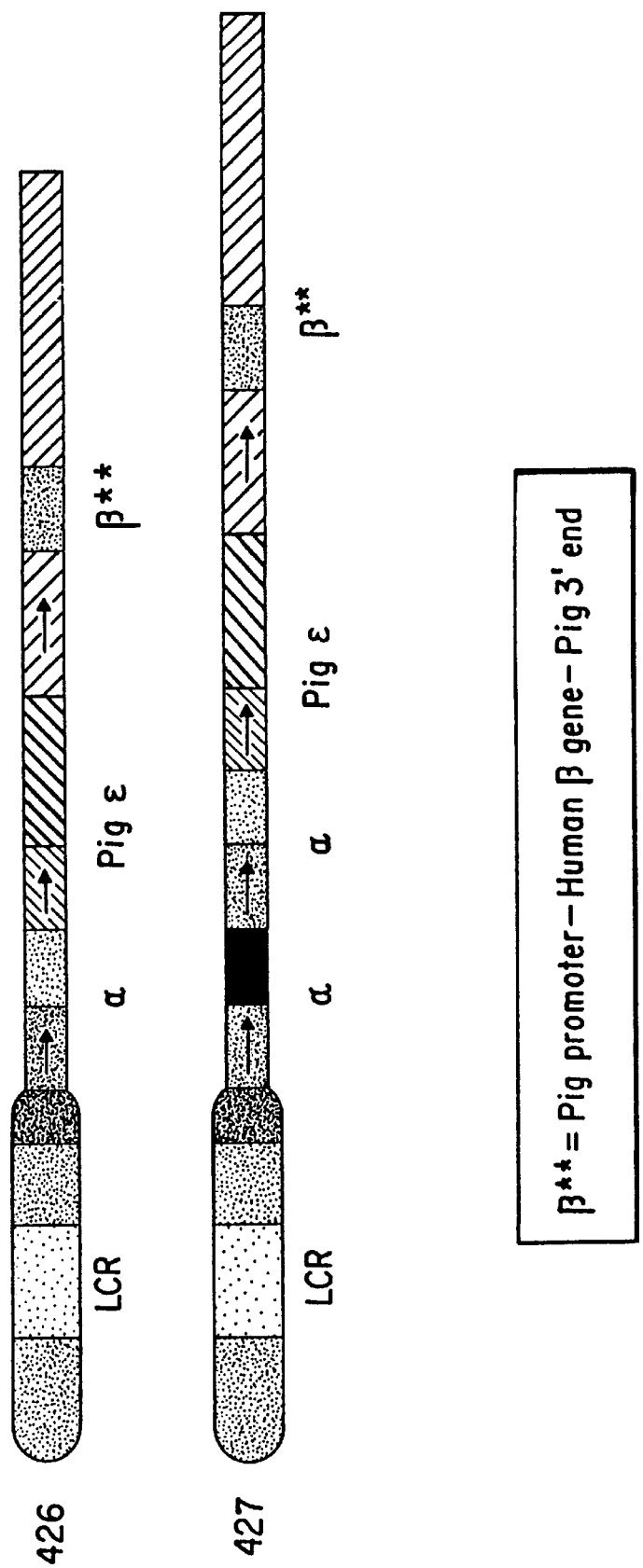

FIG. 14. Representation of the 426 and 427 expression cassettes for the production of ε$^{pig}$ β$^{human}$ and α$^{human}$ hemoglobins in transgenic pigs.

Figure 15:
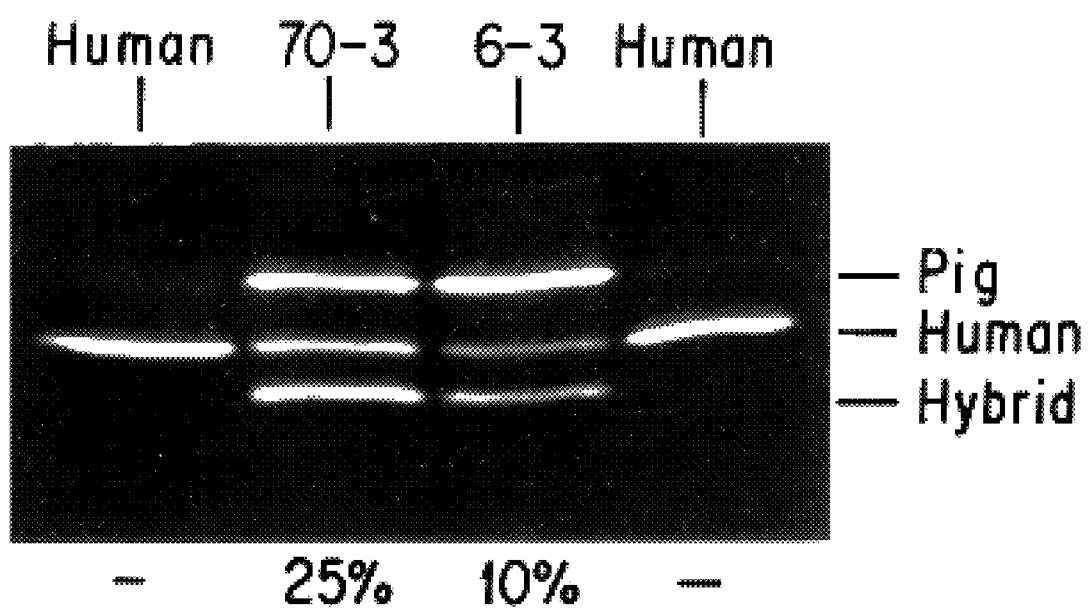

FIG. 15. Iso-electric focussing gel of hemoglobin produced by transgenic pig 70-3, which carries the 339 construct, and by transgenic pig 6-3, which carries the 116 construct. Human hemoglobin is run as a standard.

Figure 16:
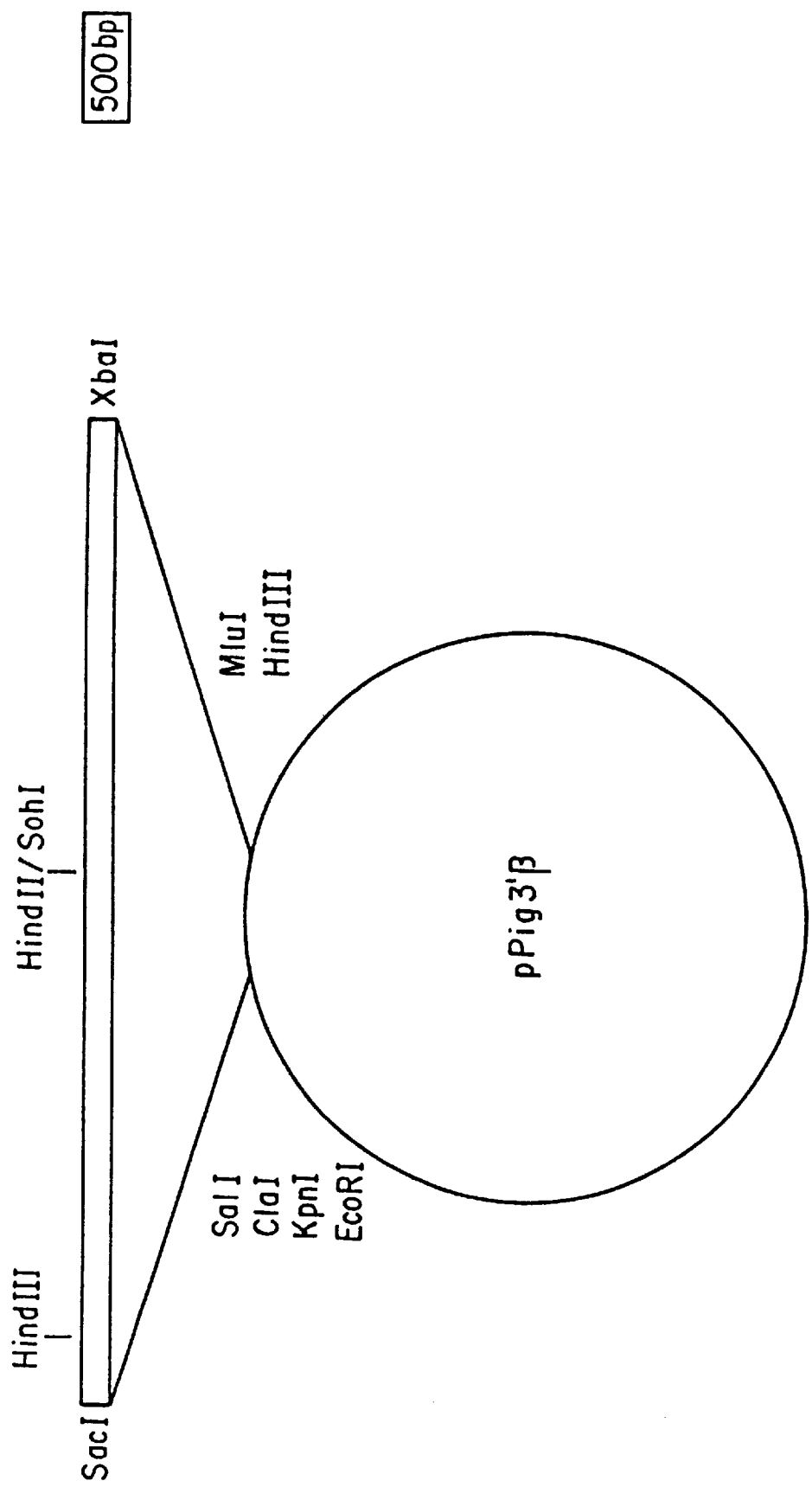

FIG. 16. Map of plasmid pig 3'β containing the 3' end of the pig beta globin gene.

FIG. 17. Transgenic pigs obtained from construct "339" (See FIG. 1R). Levels of human hemoglobin expression and copy number are shown.

Figures 18A, 18B:
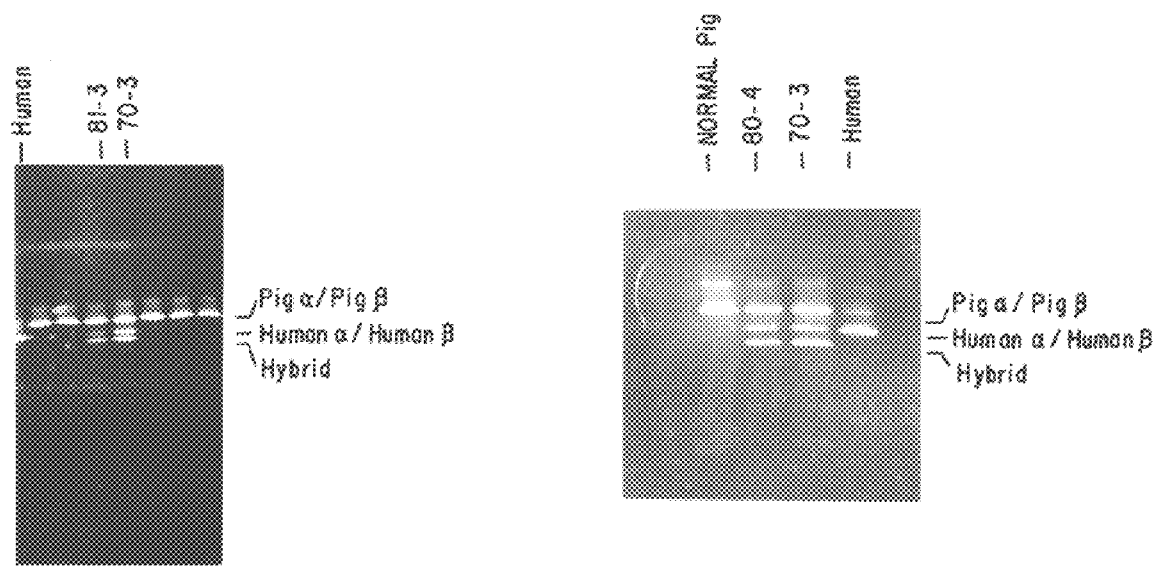

FIG. 18. Isoelectric focussing gel of hemoglobin levels in transgenic pigs obtained using construct "339".

Figure 19:
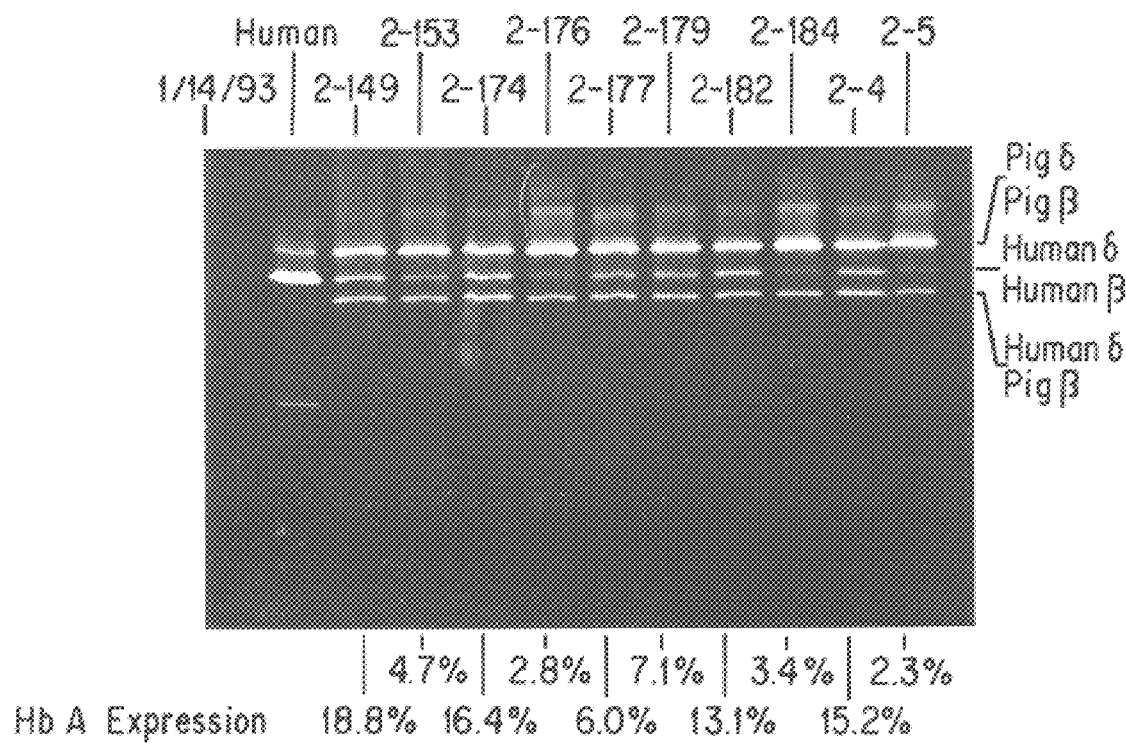

FIG. 19. Isoelectric focussing gel demonstrating levels of hemoglobin expression in representative transgene positive 38-4 offspring carrying the "185" construct (or αpβ construct; see FIG. 1B).

Figure 20:
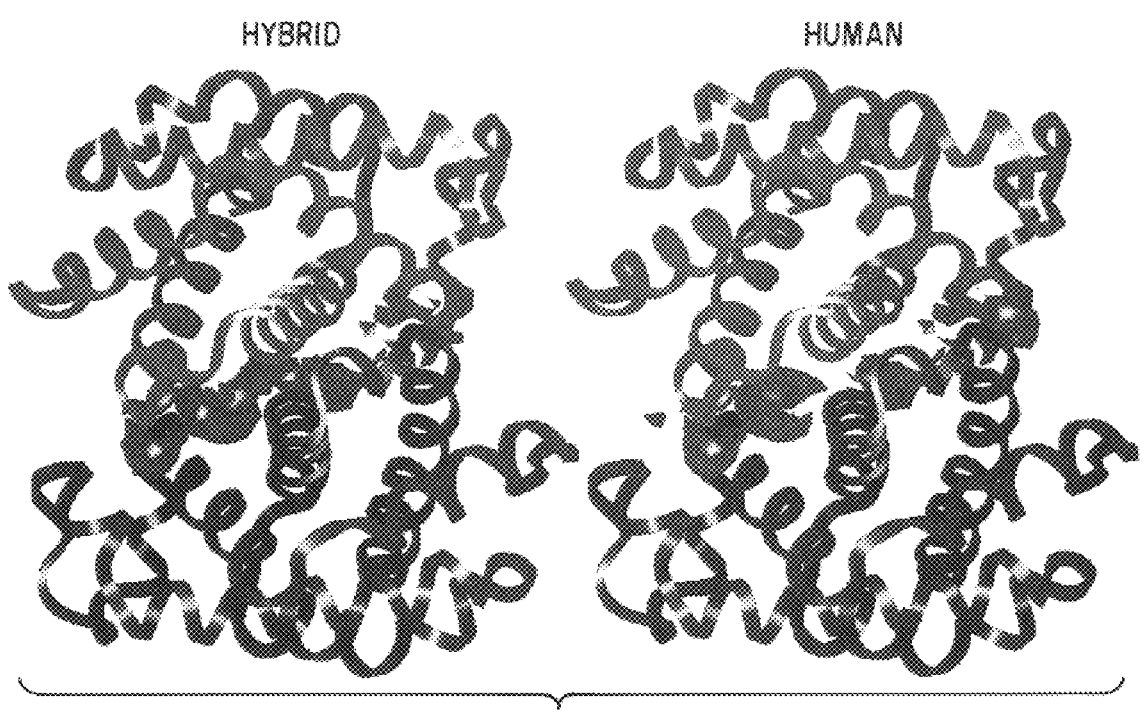

FIG. 20. Molecular modeling of hybrid human α/pig β and human α/human β hemoglobin molecules. β subunits are in blue, α subunits in red. Above the middle helix of the β human (blue) one can see a gap in the green contour (see arrow). In the hybrid this gap is filed in. This difference is due to a change at β112 Cys→Val where Valine contributes to greater hydrophobic interactions.

Figure 21:
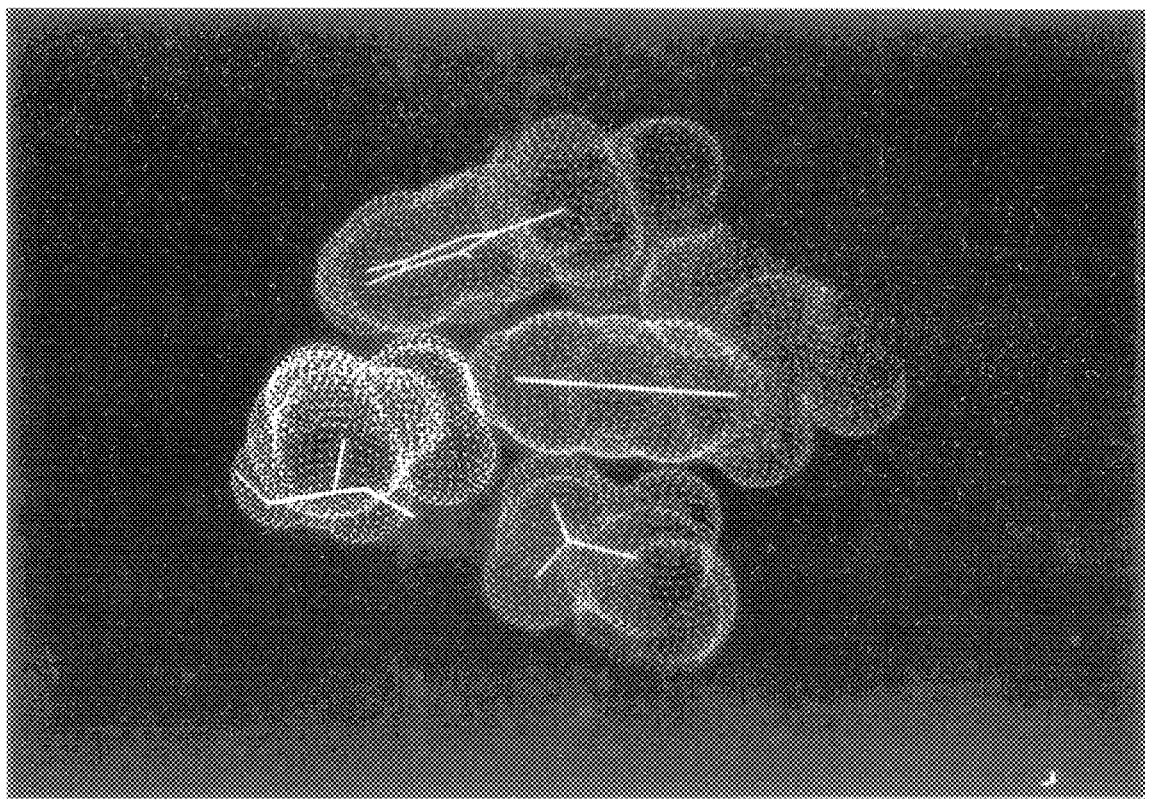

FIG. 21. Molecular modeling demonstrating the differences at the α$_1$β$_1$ interface between a β globin containing Cys at position 112 (the yellow molecule) and a β globin with Val at position 112 (the white molecule). Cys is yellow, Val is white and the opposing α interface is red. Val is flexible. One arm of its branch can easily move for a nearly perfect fit against the α subunit residues. The yellow Cys is slightly further allowing for a small gap (see arrow). Biosyn's standard default Van der Waal's distance was used.

Figure 22A:
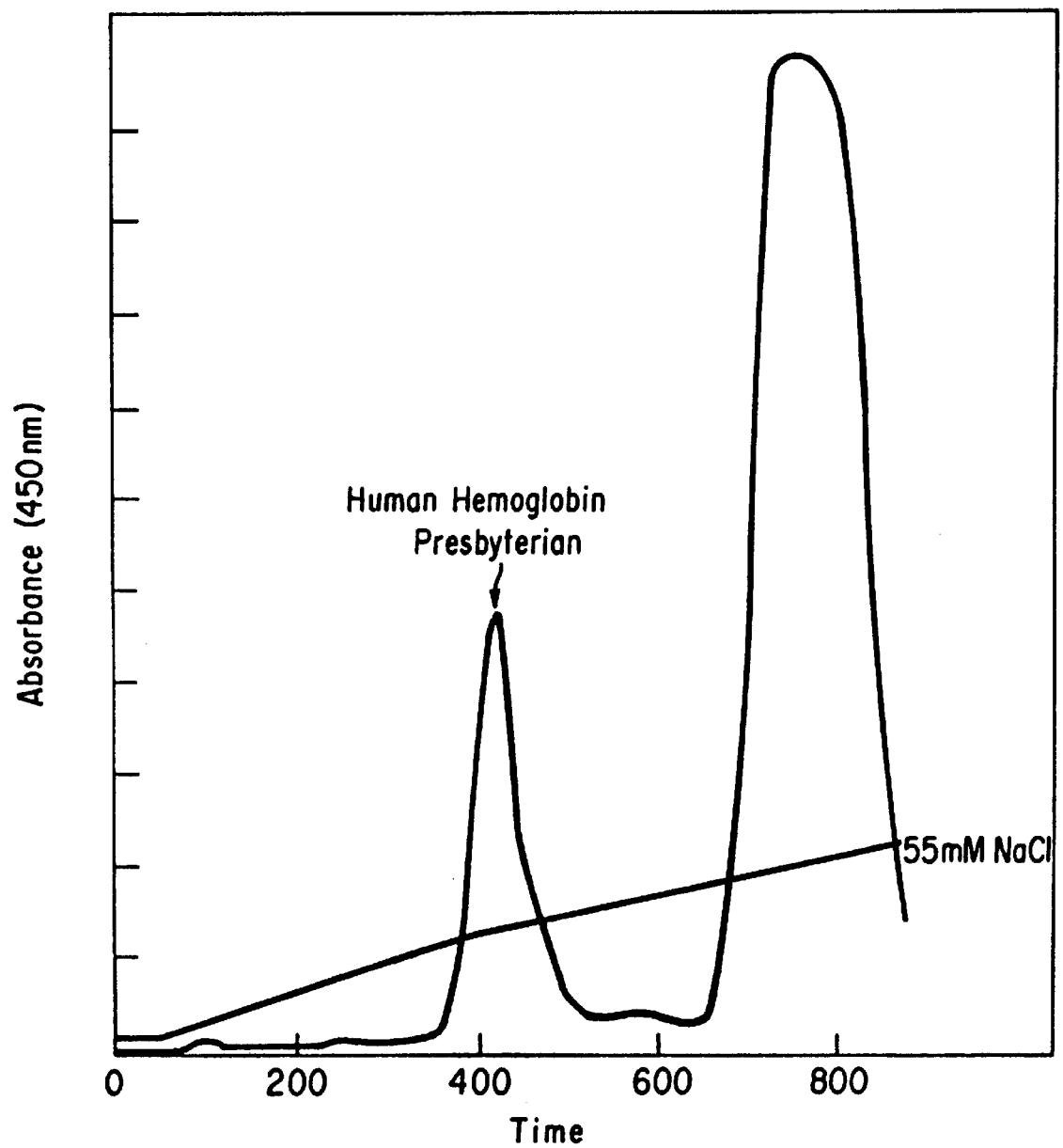
Figure 22B:
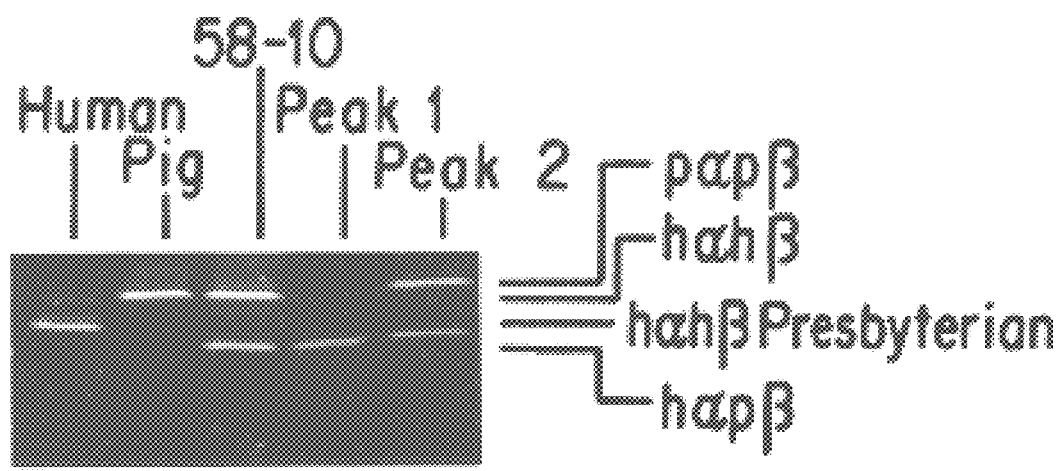

FIG. 22. Purification of Hb Presbyterian from transgenic pig hemosylate.

Figure 23:
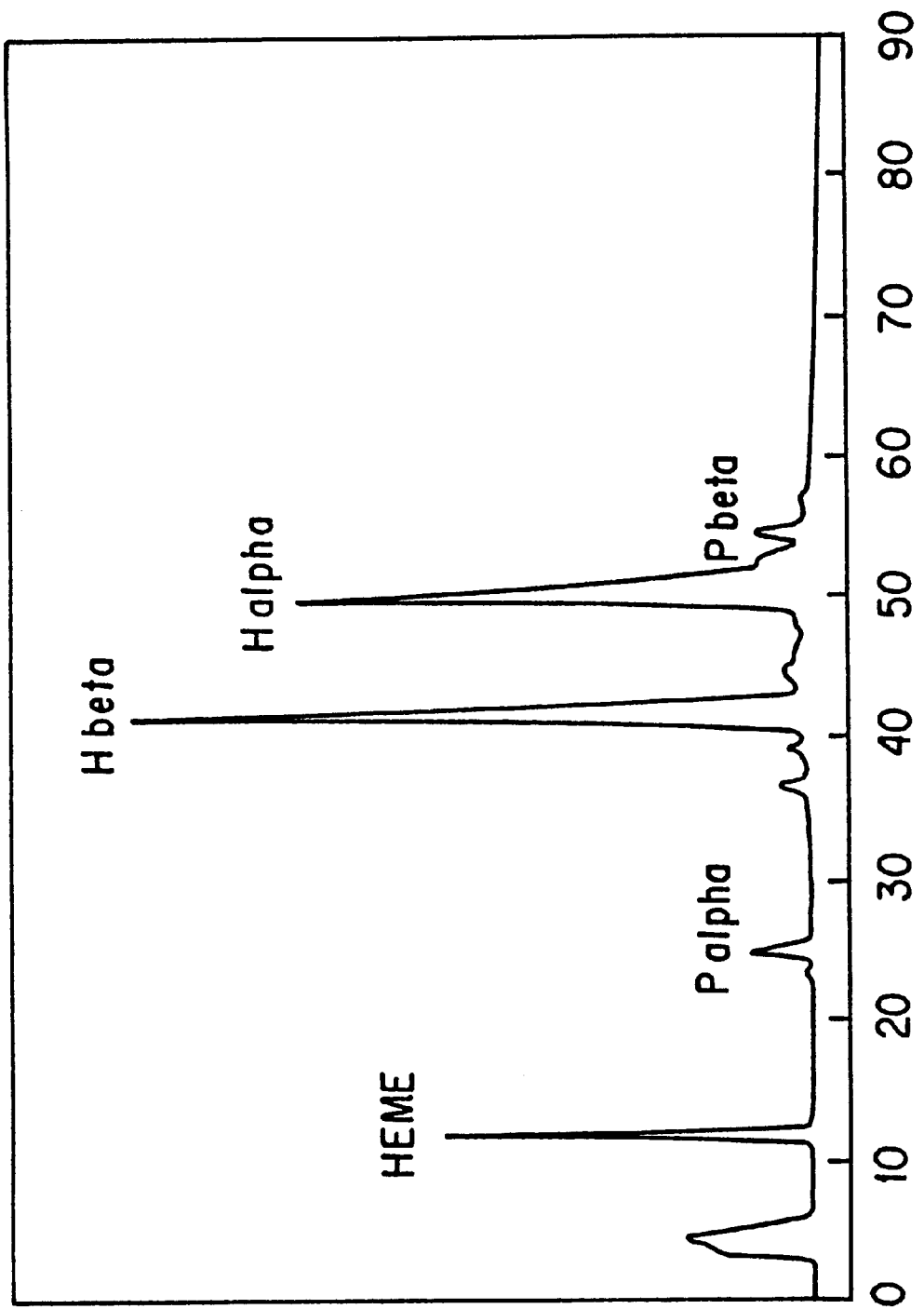

FIG. 23. Characterization of purified Hb Presbyterian by HPLC showing separation of the heme moiety, pig α globin ("p alpha"), human beta globin ("h beta"), human alpha globin ("h alpha") and pig beta globin ("p beta").

Figure 24:
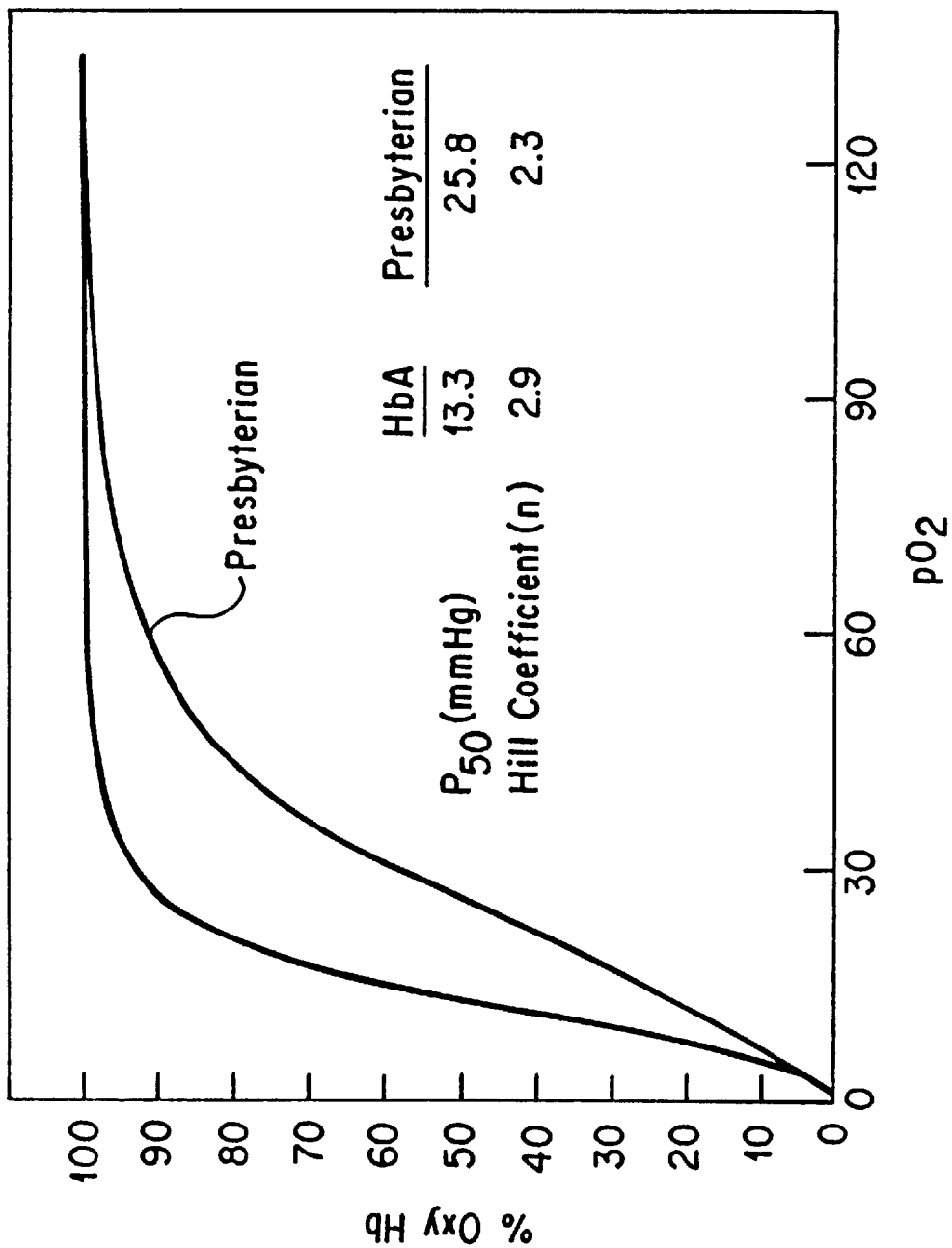

FIG. 24. Oxygen binding curve for Hb Presbyterian.

Figure 25:
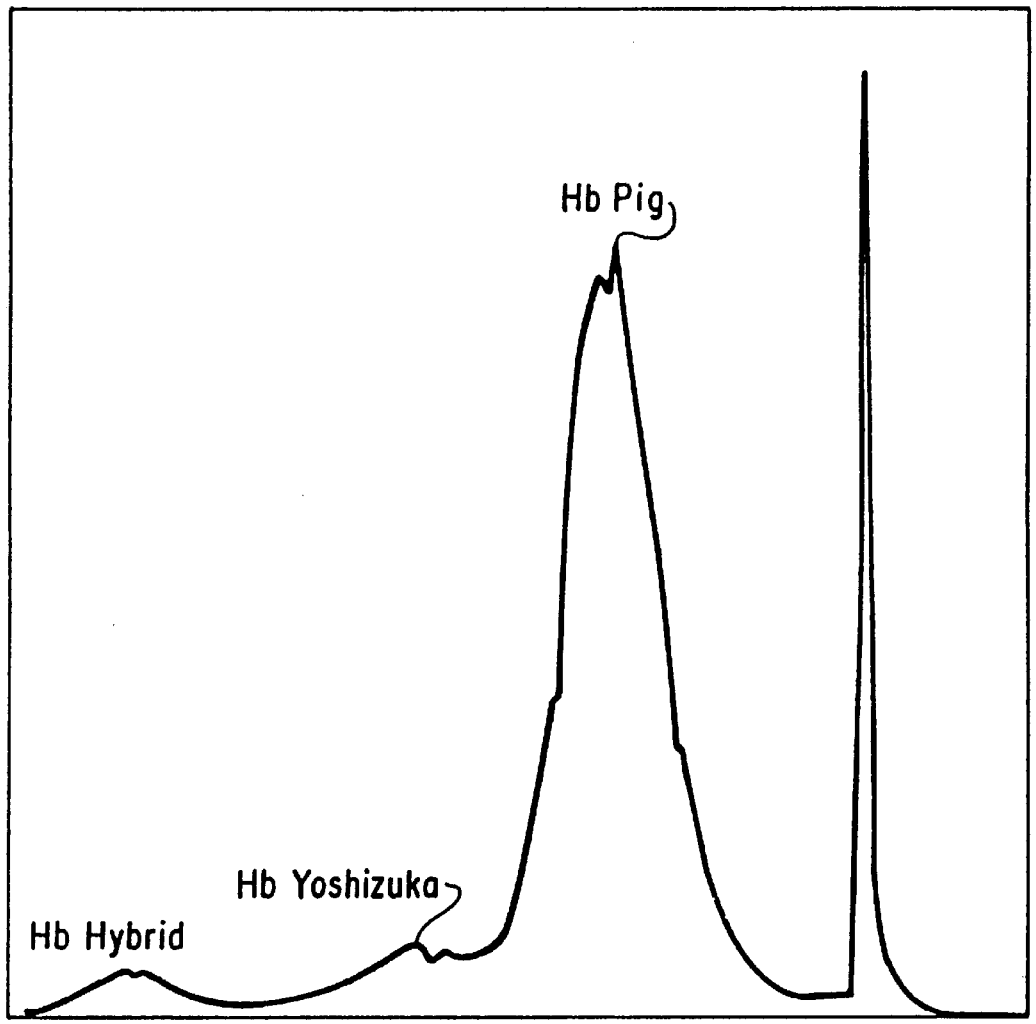

FIG. 25. Purification of Hb Yoshizuka from transgenic pig hemolysate.

Figure 26A:
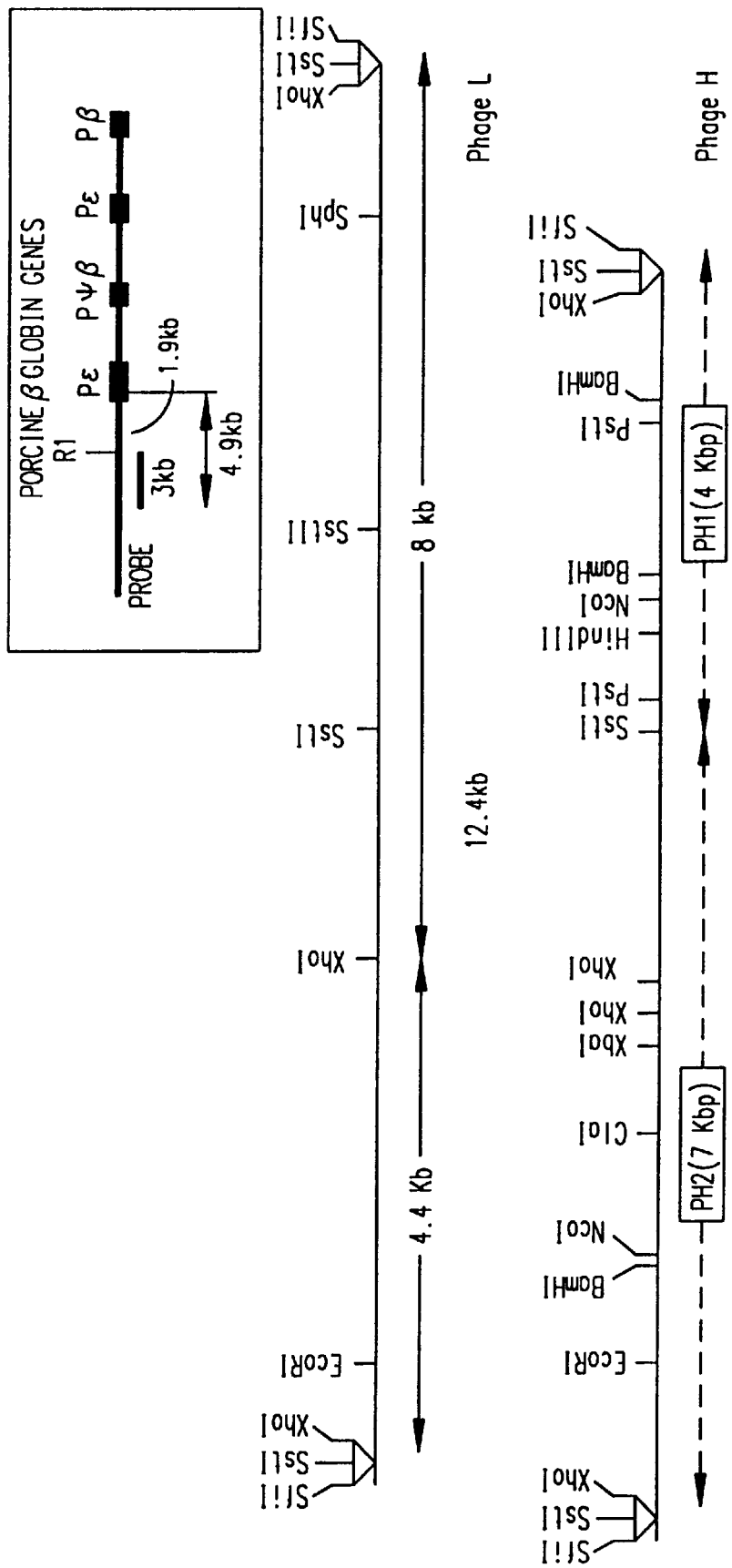
Figure 26B:
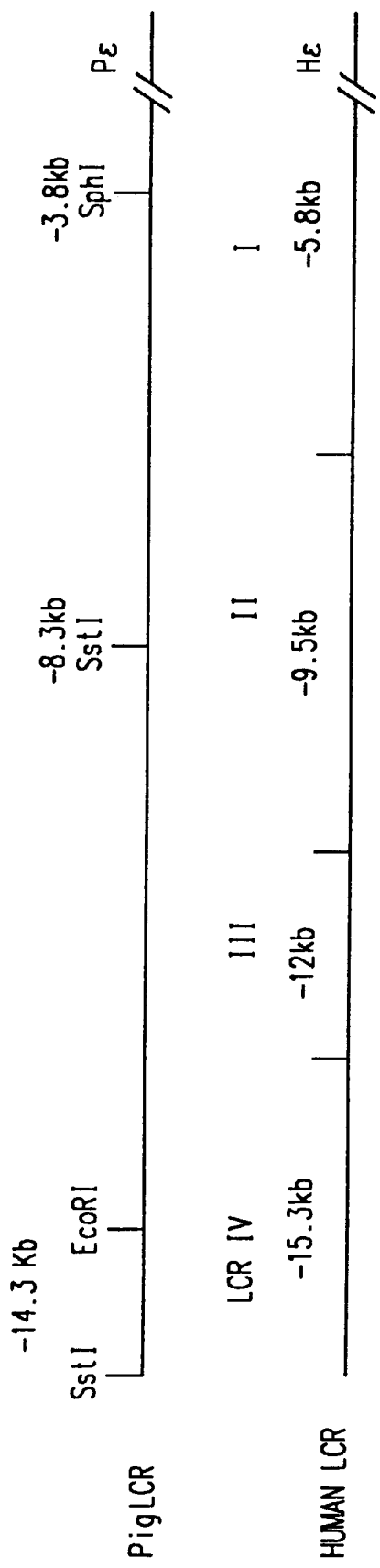

FIG. 26A and 26B. Porcine β LCR clones. FIG. 26A. Restriction analysis of lambda phage clone Phage L and Phage H. The insert shows the most probable arrangement of porcine β globin genes. The location of the probe used to screen the library is shown. FIG. 26B. Comparison of the distances of human LCRs from human ξ genes with porcine LCRs from porcine ξ genes.

FIG. 27.(A) PH1-TA1 (SEQ. ID NO:4). Sequence of 3' end of the plasmid PH1. This is part of porcine LCR I. (B) Comparison of PH1-TA1 with human β-globin region on chromosome 11 (SEQ. ID NO:5). The human sequence (from 12499–12901) is part of LCR I.

FIG. 28. joined plcr2(SEQ. ID NO:6): The 477 bp sequence of 5' end of plasmid PH1 was joined with 534 bp sequence of 3' end of plasmid PH2. This is part of porcine LCR II.

FIG. 29. Comparison of joined plcr2 with human β-globin region on chromosome 11 (SEQ. ID NO's: 7, 8 & 9). The human sequence (from 7276–8017) is part of LCR II.

FIG. 30A and 30B. PH2-T7. FIG. 30A. Sequence of 5' end of plasmid PH2-T7 (SEQ. ID NO:10). FIG. 30B. Comparison of PH2-T7 with human β-globin region on chromosome 11 (SEQ. ID NO:11). The human sequence (from 1450–1487) is part of LCR III.

Figure 31:
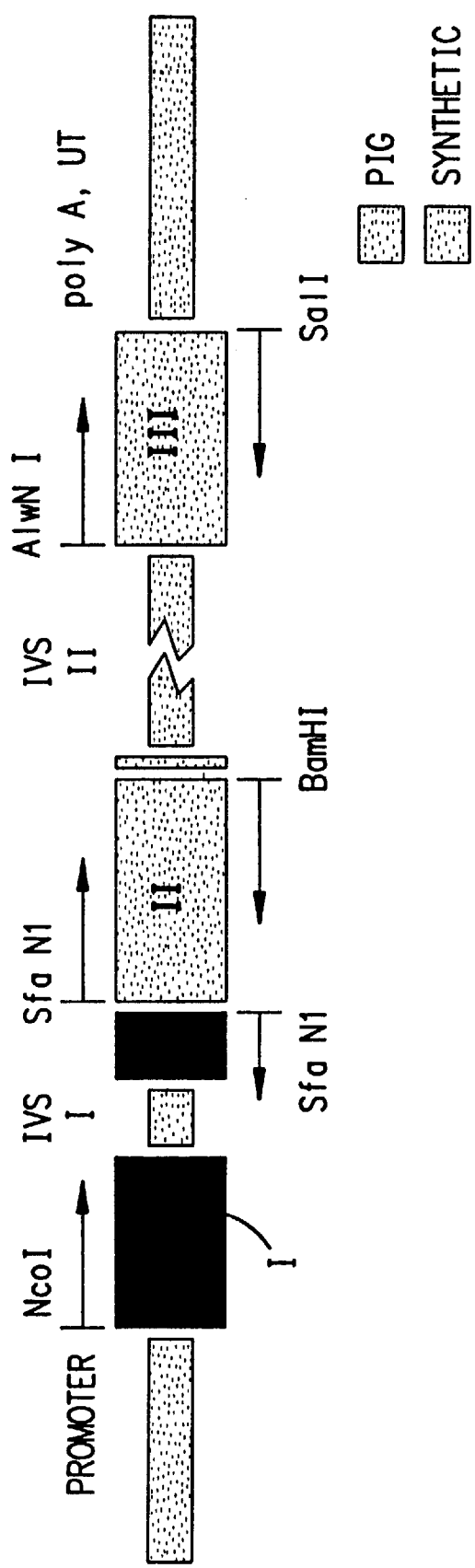

FIG. 31. Schematic of optimized β-globin gene including important restriction sites used for construction. Promoter region, Intervening sequences I and II (IVSI, IVSII) as wekk as poly-A and 3'UTR region are pig sequences. Exon 1, 2 and 3 encoded human β-globin with codons optimized for use in the pig system.

Figure 32:
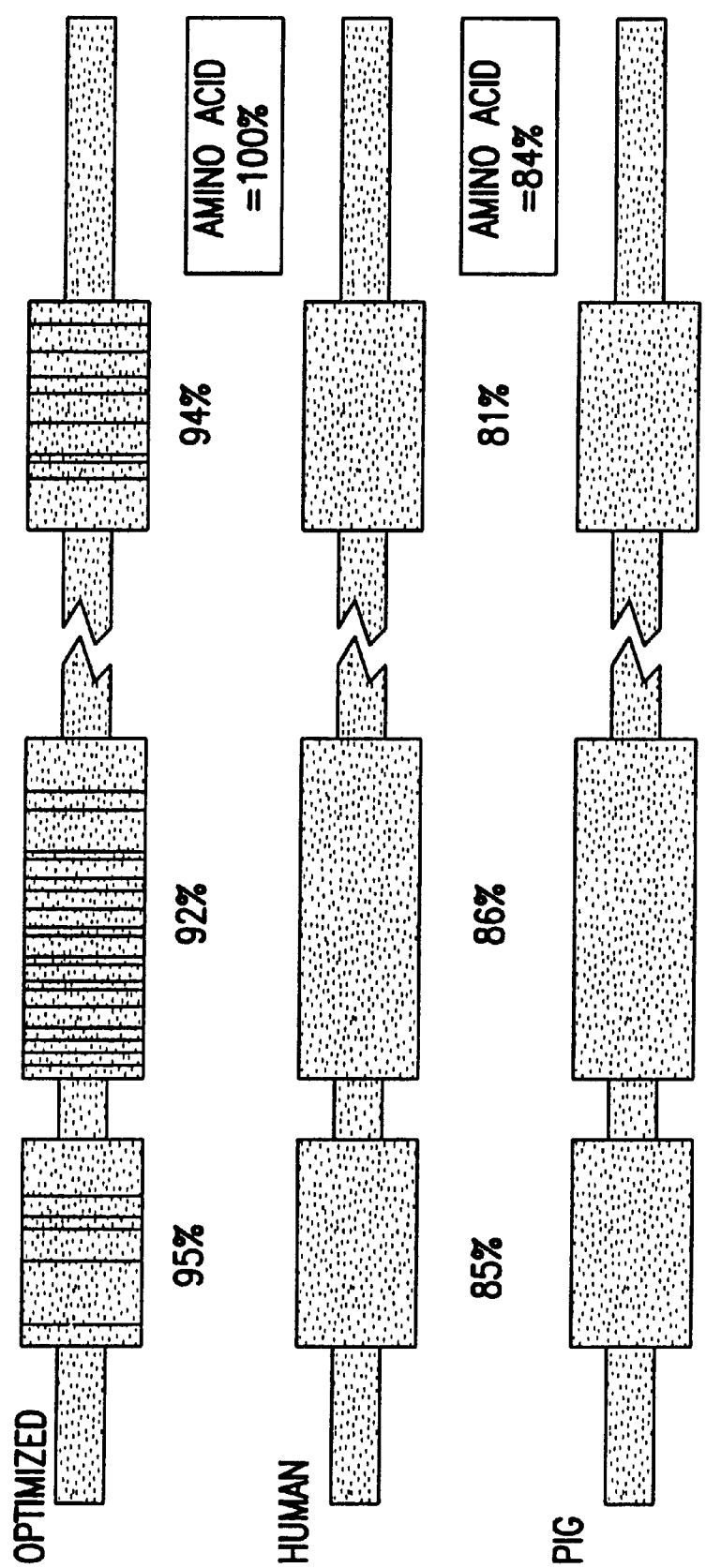

FIG. 32. Comparison of coding sequences of optizimed, human and pig β-globin genes showing percent homology between the optimized and human sequences and the human and pig sequences. Lines in the optimized sequence indicated codon changes from the human sequence.

Figure 33:
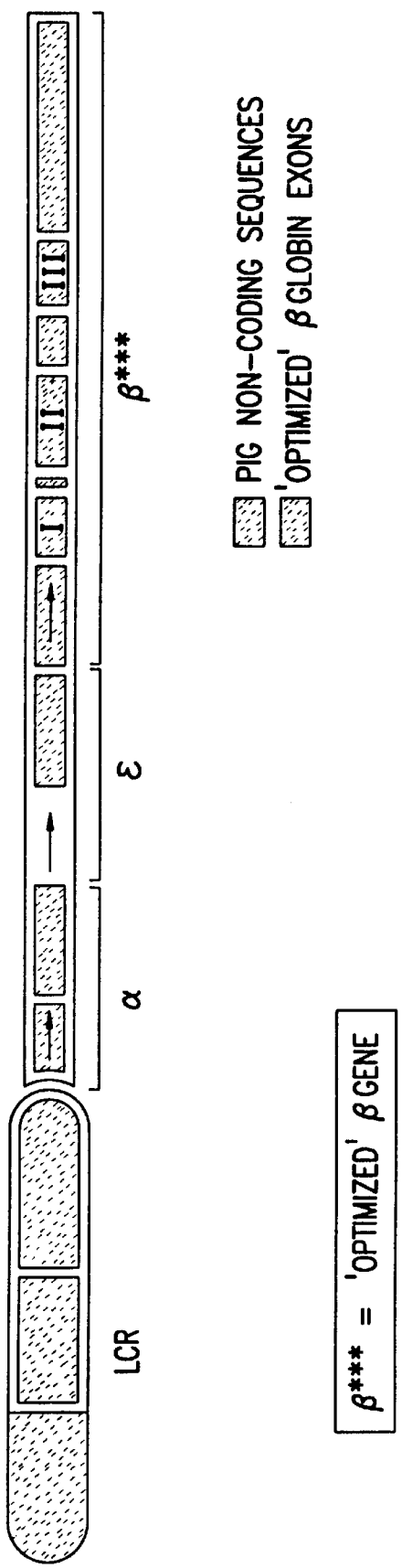

FIG. 33. Construct 505. This construct contains the human locus control region (LCR), the human α-globin gene driven by its own promoter, the human ξ-globin gene also driven by its own promoter, and the optimized β-globin gene which has the optimized coding region, includes the porcine introns, poly A and 3'UTR and is driven by the porcine promoter. The gene order in this construct is LCRαξβ* (where * signifies optimized β gene).

Figure 34:
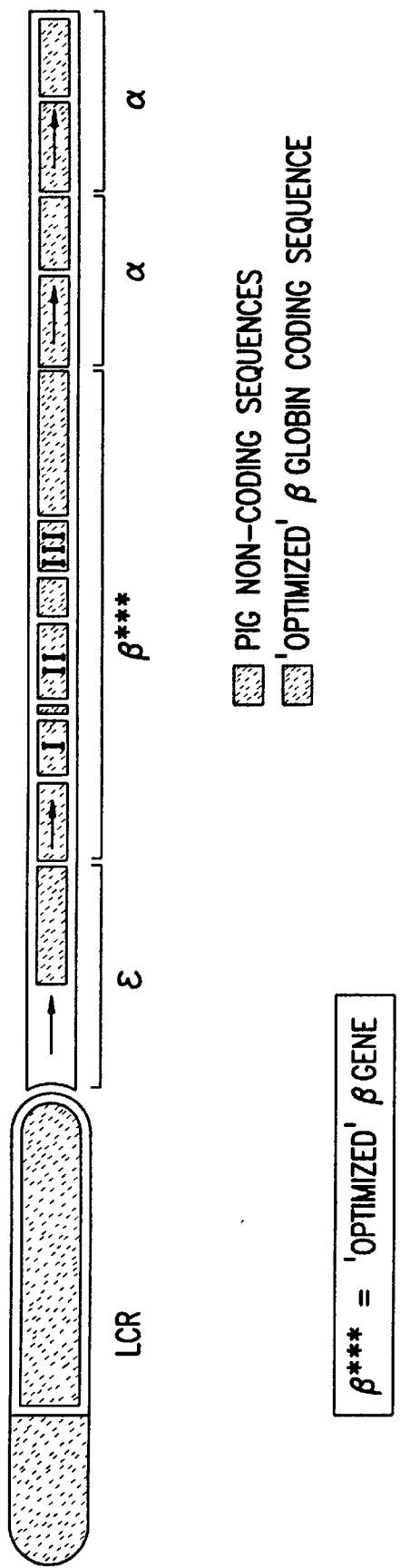

FIG. 34. Construct 515. This construct contains the human locus control region, the human α-globin gene driven by its own promoter, the human ξ-gene also driven by its own promoter, and the optimized β-globin gene which has the optimized coding region, includes the porcine introns, poly A and 3'UTR and is driven by the porcine promoter. The gene order in this construct is LCRξβαα (where * signifies optimized β gene).

FIG. 35. Comparison of human (SEQ. ID NO's: 12, 13 & 14) and pig (SEQ. ID NO's: 15, 16 & 17) β-globin coding sequences. The figure is divided into Exons 1, 2 and 3. Differences are signified by small letters in the pig (bottom) sequence. Codons with changes are underlined.

FIG. 36. Comparison of human (SEQ. ID NO's: 12, 13 & 14) and optimized (SEQ. ID NO's: 18, 20 & 22) β-globin coding sequences. The figure is divided into Exons 1, 2 and 3. Differences are signified by small letters in the optimized (bottom) sequence. Codons with changes are underlined.

FIG. 37. Comparison of optimized (SEQ. ID NO's: 18, 20 & 22) and pig (SEQ. ID NO's: 15, 16 & 17) β-globin coding sequences. Figure is divided into Exons 1, 2 and 3. Differences are signified by small letters in the pig (bottom) sequence. Codons with changes are underlined.

FIG. 38. Coding sequences (SEQ. ID NO's: 18, 20 & 22) and amino acid sequence (SEQ. ID NO's: 19, 21 & 23) of optimized β-globin gene. Three dashes are placed between Exons.

FIG. 39. Comparison of human (SEQ. ID NO's: 24, 25 & 26) and optimized (SEQ. ID NO's: 19, 21 & 23) β-globin amino acid sequence indicating that they are identical.

5. DETAILED DESCRIPTION OF THE INVENTION

The present invention provides for a method of producing human hemoglobin that utilizes transgenic pigs, novel globin-encoding nucleic acid constructs, and transgenic pigs that express human hemoglobin. For purposes of clarity of description, and not by way of limitation, the detailed description of the invention is divided into the following subsections:

(i) preparation of globin gene constructs;
(ii) preparation of transgenic pigs;
(iii) preparation of human hemoglobin and its separation from pig hemoglobin; and
(iv) preparation of human/pig hybrid hemoglobin.

5.1. PREPARATION OF GLOBIN GENE CONSTRUCTS

The present invention provides for a method of producing human globin and/or hemoglobin in transgenic pigs. Human hemoglobin is defined herein to refer to hemoglobin formed by globin chains encoded by human globin genes (including alpha, beta, delta, gamma, epsilon and zeta genes) or variants thereof which are naturally occurring or the products of genetic engineering. Such variants are at least about ninety percent homologous in amino acid sequence to a naturally occurring human hemoglobin. In preferred embodiments, the human hemoglobin of the invention comprises a human alpha globin and a human beta globin chain. The human hemoglobin of the invention comprises at least two different globin chains, but may comprise more than two chains, to form, for example, a tetrameric molecule, octameric molecule, etc. In preferred embodiments of the invention, human hemoglobin consists of two human alpha globin chains and two human beta globin chains. As discussed infra, the present invention also provides for hybrid hemoglobins comprising human α globin and pig β globin.

According to particular embodiments of the present invention, at least one human globin gene, such as a human alpha and/or a human beta globin gene, under the control of a suitable promoter or promoters, is inserted into the genetic material of a pig so as to create a transgenic pig that carries human globin in at least some of its red blood cells. This requires the preparation of appropriate recombinant nucleic acid sequences. In preferred embodiments of the invention, both human a and human β genes are expressed. In an alternative embodiment, only human α globin or human β globin is expressed. In further embodiments, human embryonic or fetal globin genes are expressed or are used as developmental expression regulators of adult genes.

Human alpha and beta globin genes may be obtained from publicly available clones, e.g. as described in Swanson et al., 1992, Bio/Technol. 10:557–559. Nucleic acid sequences encoding human alpha and beta globin proteins may be introduced into an animal via two different species of recombinant constructs, one which encodes human alpha globin, the other encoding human beta globin; alternatively, and preferably, both alpha and beta-encoding sequences may be comprised in the same recombinant construct. The pig epsilon globin gene is contained in plasmid psaf/pig ε (k) (FIG. 13), deposited with the ATCC and assigned accession number 75373.

A suitable promoter, according to the invention, is a promoter which can direct transcription of human alpha and/or beta globin genes in red blood cells. Such a promoter is preferably selectively active in erythroid cells. This would include, but is not limited to, a globin gene promoter, such as the human alpha, beta, delta, epsilon or zeta promoters, or a globin promoter from another species. It may, for example, be useful to utilize pig globin promoter sequences. For example, as discussed in Section 10, infra, the use of the endogenous pig β globin gene control region, as contained in plasmid Pgem5/Pigβpr(K), deposited with the ATCC and assigned accession number 75371 and having the sequence set forth in FIG. 8, has been shown to operate particularly efficiently. The human alpha and beta globin genes may be placed under the control of different promoters, but, since it has been inferred that vastly different levels of globin chain production may result in lethality, it may be preferable to place the human alpha and beta globin genes under the control of the same promoter sequence. In order to avoid chain imbalance and/or titration of transcription factors due to constitutive β-globin promoter activity in an inappropriate cell type, it is desirable to design a construct which leads to coordinate expression of human alpha and beta globin genes at the same time in development and at quantitatively similar levels.

In one particular, non-limiting embodiment of the invention, a construct comprising the ααβ construct (also termed the "116" construct; Swanson et al., 1992, Bio/Technol. 10:557–559; see FIG. 1A) may be utilized. Although this construct, when present as a transgene at high copy number, has resulted in deleterious effects in mice, it has been used to produce healthy transgenic pigs (see Example Section 6, infra).

In another particular, non-limiting embodiment of the invention, a construct comprising the αpβ sequence (also termed the "185" construct; see FIG. 1B) may be used. Such a construct has the advantage of placing both alpha and beta globin-encoding sequences under the control of the same promoter (the alpha globin promoter).

In another particular, non-limiting embodiment of the invention, a construct coding for di-alpha globin like polypeptides may be introduced to form transgenic pigs that produce human hemoglobins with decreased dimerization and an increased half-life (WO Patent 9013645).

In yet another particular, non-limiting embodiment of the invention, a construct comprising the human adult alpha globin and epsilon globin gene, the pig beta globin gene control region and the human beta globin gene (the "339construct, see FIG. 1R) may be used.

Furthermore, the incorporation of a human or pig epsilon globin gene into the construct may facilitate the production of high hemoglobin levels. The pig epsilon globin gene may permit correct developmental regulation of the adult β globin gene. High levels of expression of introduced adult alpha globin gene(s) may result in a chain imbalance problem during intrauterine development of a transgenic pig embryo (because an adult beta globin gene in the construct would not yet be expressed) thereby compromising the viability of the embryo. By providing high levels of embryonic globins during development, the viability of such embryos may be improved. The pig epsilon globin gene, as contained in plasmid Psaf/Pigε, deposited with the ATCC and assigned accession number 75373, is shown in FIG. 13.

The present invention, in further specific embodiments, provides for (i) the construct βpα, in which the human alpha and beta globin genes are driven by separate copies of the human beta globin promoter (FIG. 1C); (ii) the εpζβαpβ construct, which comprises human embryonic genes zeta and epsilon under the control of the epsilon promoter and both alpha and beta genes under the control of the beta promoter (FIG. 1D); (iii) the ζpεαpβ construct, which comprises human embryonic genes zeta and epsilon under the control of the zeta promoter and both alpha and beta genes under the control of the alpha promoter (FIG. 1E); (iv) the αpβ construct carrying a mutation that results in an aspartic acid residue (rather than an asparagine residue) at amino acid number 108 of β globin protein, to produce hemoglobin Yoshizuka (FIG. 1F, construct "294"); (v) the αpβ construct carrying a mutation that results in a lysine residue (rather than an asparagine residue) at amino acid number 108 of β-globin protein, to produce hemoglobin Presbyterian (FIG. 1G, construct "293"); (vi) the αpβ (Δα) construct, coinjected with LCR α which comprises the human β-globin gene under the control of the human α-globin promoter and a separate nucleic acid fragment comprising the human α-globin gene under its own promoter (FIG. 1H); (vii) the αpβ construct carrying a mutation that results in a cysteine residue (rather than a threonine residue) at amino acid number 134 of α-globin protein (FIG. 1I); (viii) the αpβ construct carrying a mutation that results in a serine residue (rather than a cysteine residue) at amino acid number 104 of the α-globin protein, an alanine residue (rather than a cysteine residue) at amino acid number 93 of the β-globin protein and a valine residue (rather than a cysteine residue) at amino acid number 112 of the β-globin protein (FIG. 1J); (ix) the αpδ construct, which comprises the human adult α-globin promoter under its own promoter and the human δ-globin gene under the control of the human adult α-globin promoter (FIG. 1K); (x) Construct αpδ(Δα) coinjected with LCR α, which comprises the human α-globin gene under the control of the human α-globin promoter and a separate nucleic acid fragment comprising the human α-globin gene under its own promoter (FIG. 1L); (xi) Construct LCR α coinjected with LCR εβ, which comprises the human α-globin gene under the control of its own promoter and a separate nucleic acid fragment comprising the human embryonic ε-globin gene and the adult β-globin gene under the control of their own promoters (FIG. 1M); (xii) the αpβ construct carrying a mutation that results in a methionine residue (rather than a lysine residue) at amino acid number 61 of the α-globin protein (FIG. 1N); (xiii) the εαβ construct, which comprises the human embryonic epsilon gene, the human adult alpha globin gene and the human adult beta globin gene linked in tandem from 5'- to 3' (FIG. 1O); (xiv) the αεβ construct, which comprises the human adult alpha-globin gene, the human embryonic epsilon globin gene and the human adult beta globin gene linked in tandem from 5'- to 3' (FIG. 1P); (xv) the ααεβ construct, which comprises two copies of the human adult alpha-globin gene, the human embryonic epsilon globin gene and the human adult beta globin gene linked in tandem from 5'- to 3' (FIG. 1Q); (xvi) the αε ($^{pig}$βp) β construct, which comprises the human adult alpha-globin gene, the human embryonic epsilon globin gene and the human adult beta globin gene under the control of the endogenous porcine adult beta globin promoter all linked in tandem from 5'- to 3' (FIG. 1R); (xvii) the αpβ construct carrying a mutation that results in a cysteine residue (rather than an aspartic acid residue) at amino acid number 75 of the α-globin protein (FIG. 1S); (xviii) the αpβ construct carrying a mutation that results in an arginine residue (rather than a tyrosine residue) at amino acid number 42 at the α-globin protein (FIG. 1T); (xvix) the LCR εβαα construct, which comprises the human embryonic epsilon globin gene, the human adult beta globin gene and two copies of the human adult alpha-globin gene linked in tandem from 5'- to 3' (FIG. 1U); (xx) the LCR εβα construct, which comprises the human embryonic epsilon globin gene, the human adult beta globin gene and the human adult alpha-globin gene linked in tandem from 5'- to 3' (FIG. 1V); (xxi) the αpβ construct carrying a mutation that results in a lysine residue (rather than a tyrosine residue) at amino acid number 42 of the α-globin protein (FIG. 1W);

(xxii) the αpβ construct carrying a mutation that results in an arginine residue (rather than a tyrosine residue) at amino acid number 42 at the α-globin protein and a glutamic acid residue (rather than an aspartic acid residue) at amino acid number 99 of the β-globin protein (FIG. 1X); (xxiii) the αpβ construct carrying a mutation that results in a lysine residue (rather than a tyrosine residue) at amino acid number 42 of the aglobin protein and a glutamic acid residue (rather than an aspartic acid residue) at amino acid number 99 of the β-globin protein (FIG. 1Y); and (xxiv) the α$^{pig}$ε ($^{pig}$βp)β construct comprising the pig epsilon globin gene and beta globin control region (constructs 426 and 427, FIG. 14).

In transgenic pigs expressing human hemoglobin three types of hemoglobin dimers are detectable: pig α/pig β, human α/human β, and hybrid human α/pig β. In certain embodiments of the invention, it may be desirable to decrease the amount of hybrid hemoglobin. Accordingly, the molecular basis for the formation of hybrid hemoglobin has been investigated using molecular modeling studies. Based on the information derived from these studies, the human alpha and beta globin structures can be modified to increase the level of human α/human β dimers (see Section 11.), so that in further embodiments of the invention, constructs comprising the αpβ sequence may be modified to code for α or β globin proteins carrying amino acid changes that will lead to increases in the level of human α/human β hemoglobin dimers in transgenic pigs. The present invention, provides for constructs which encode human α globin and human β globin carrying one or more of the following mutations in the α globin molecule: (1) a Thr at position 30 instead of Glu; (ii) a Tyr at position 36 instead of Phe; (iii) a Phe instead of Leu at position 106; (iv) a Ser or Cys instead of Val at position 107; and/or (v) a Cys instead of Ala at position 111. In specific embodiments, the construct carrying such mutation(s) is the αpβ construct. The present invention, in further embodiments, provides for constructs which encode human a globin and human β globin carrying one or more of the following mutations in the β globin molecule: (1) a Leu instead of Val at position 33; (ii) a Val or Ile instead of Cys at position 112; (iii) a Val or Leu instead of Ala at position at position 115; (iv) a His instead of Gly at position 119; (v) a Met instead of Pro at position 125; (vi) an Ile instead of Ala at position 128; and/or (vii) a Glu instead of Gln at position 131; and/or (viii) a Glu instead of Gln at position 131. In specific embodiments, the construct carrying the mutation(s) is the αpβ construct.

In further embodiments it may be desirable to modify the human β-globin gene to optimize expression in transgenic pigs. For example, the human β-globin gene, from the promoter region through the coding sequence and into the polyadenylation site and 3' untranslated region, may be engineered to be similar to the pig β-globin gene, but without altering the amino acid sequence from that of the authentic wild-type human β-globin. Such an optimized gene is contained in the plasmid designated pGEM3 β* Δ3', deposited with the American Type Culture Collection (ATCC) and assigned accession number 75520. Constructs which contain the optimized human β-globin gene, may be used to increase the levels of β-globin expressed in transgenic animals (constructs 505 and 515, FIGS. 34 and 35 respectively).

In further embodiments the porcine LCR region as depicted in FIG. 26A and contained in plasmids designated pPH1 and pPH2 (deposited with the ATCC and assigned accession numbers 75518 and 75519), may be used in plasmid constructs to enhance the expression of globin proteins in transgenic pigs. The porcine LCR may also be useful in the expression of non-globin proteins in pig erythrocytes.

In further embodiments it may be desirable to include, in constructs, the untranslated 3' end of the pig beta globin gene as contained in plasmid pPig3'β (FIG. 16) as deposited with the ATCC and assigned accession number 75372. (see, for example, construct 354 in FIG. 12 and FIGS. 426 and 427 in FIG. 14). Such constructs may also be useful in the expression of non-globin protein in pig erythrocytes.

In further embodiments, the pig beta globin control region depicted in FIGS. 8 and 9 may be used in constructs that encode non-globin proteins for the expression of said proteins in transgenic pig or other non-human erythrocytes.

The recombinant nucleic acid constructs described above may be inserted into any suitable plasmid, bacteriophage, or viral vector for amplification, and may thereby be propagated using methods known in the art, such as those described in Maniatis et al., 1989, Molecular Cloning: A Laboratory Manual, Cold Spring Harbor, N.Y. In the working examples presented below, the pUC vector (Yanish-Perron et al., 1985, Gene 103–119) was utilized.

The present invention further provides for isolated and purified nucleic acids comprising the pig adult beta globin promoter regulatory region, the pig 3' beta globin region, and the pig epsilon globin gene as comprised, respectively, in plasmids pGem5/Pigβpr(K) (ATCC accession no. 75371), pPig3'β (ATCC accession no. 75372), and Psaf/pigε(k) (ATCC accession no. 75373), respectively.

Constructs may desirably be linearized for preparation of transgenic pigs. Vector sequence may desirably be removed.

5.2. PREPARATION OF TRANSGENIC PIGS

The recombinant constructs described above may be used to produce a transgenic pig by any method known in the art, including but not limited to, microinjection, embryonic stem (ES) cell manipulation, electroporation, cell gun, transfection, transduction, retroviral infection, etc. Species of constructs may be introduced individually or in groups of two or more types of construct.

According to a preferred specific embodiment of the invention, a transgenic pig may be produced by the methods as set forth in Example Section 6, infra. Briefly, estrus may be synchronized in sexually mature gilts (>7 months of age) by feeding an orally active progestogen (allyl trenbolone, AT: 15 mg/gilt/day) for 12 to 14 days. On the last day of AT feeding all gilts may be given an intramuscular injection (IM) of prostaglandin $F_{2a}$ (Lutalyse: 10 mg/injection) at 0800 and 1600 hours. Twenty-four hours after the last day of AT consumption all donor gilts may be administered a single IM injection of pregnant mare serum gonadotropin (PMSG: 1500 IU). Human chorionic gonadotropin (HCG: 750 IU) may be administered to all donors at 80 hours after PMSG.

Following AT withdrawal, donor and recipient gilts may be checked twice daily for signs of estrus using a mature boar. Donors which exhibited estrus within 36 hours following HCG administration may be bred at 12 and 24 hours after the onset of estrus using artificial and natural (respectively) insemination.

Between 59 and 66 hours after the administration of HCG one- and two-cell ova may be surgically recovered from bred donors using the following procedure. General anesthesia may be induced by administering 0.5 mg of acepromazine/kg of bodyweight and 1.3 mg ketamine/kg of bodyweight via a peripheral ear vein. Following anesthetization, the reproductive tract may be exteriorized following a mid-ventral laparotomy. A drawn glass cannula (O.D. 5 mm, length 8 cm) may be inserted into the ostium of the oviduct and anchored to the infundibulum using a single silk (2-0)

suture. Ova may be flushed in retrograde fashion by inserting a 20 g needle into the lumen of the oviduct 2 cm anterior to the uterotubal junction. Sterile Dulbecco's phosphate buffered saline (PBS) supplemented with 0.4% bovine serum albumin (BSA) may be infused into the oviduct and flushed toward the glass cannula. The medium may be collected into sterile 17×100 mm polystyrene tubes. Flushings may be transferred to 10×60 mm petri dishes and searched at lower power (50×) using a Wild M3 stereomicroscope. All one- and two-cell ova may be washed twice in Brinster's Modified Ova Culture-3 medium (BMOC-3) supplemented with 1.5% BSA and transferred to 50 µl drops of BMOC-3 medium under oil. Ova may be stored at 38° C. under a 90% $N_2$, 5% $O_2$, 5% $CO_2$ atmosphere until microinjection is performed.

One- and two-cell ova may be placed in a Eppendorf tube (15 ova per tube) containing 1 ml HEPES Medium supplemented with 1.5% BSA and centrifuged for 6 minutes at 14000×g in order to visualize pronuclei in one-cell and nuclei in two-cell ova. Ova may then be transferred to a 5–10 µl drop of HEPES medium under oil on a depression slide. Microinjection may be performed using a Laborlux microscope with Nomarski optics and two Leitz micromanipulators. 10–1700 copies of construct DNA (linearized at a concentration of about 1 ng/µl of Tris-EDTA buffer) may be injected into one pronuclei in one-cell ova or both nuclei in two-cell ova.

Microinjected ova may be returned to microdrops of BMOC-3 medium under oil and maintained at 38° C. under a 90% $N_2$, 5% $CO_2$, 5% $O_2$ atmosphere prior to their transfer to suitable recipients. Ova may preferably be transferred within 10 hours of recovery.

Only recipients which exhibit estrus on the same day or 24 hours later than the donors may preferably be utilized for embryo transfer. Recipients may be anesthetized as described earlier. Following exteriorization of one oviduct, at least 30 injected one-and/or two-cell ova and 4–6 control ova may be transferred in the following manner. The tubing from a 21 g×¾ butterfly infusion set may be connected to a 1 cc syringe. The ova and one to two mls of BMOC-3 medium may be aspirated into the tubing. The tubing may then be fed through the ostium of the oviduct until the tip reaches the lower third or isthmus of the oviduct. The ova may be subsequently expelled as the tubing is slowly withdrawn.

The exposed portion of the reproductive tract may be bathed in a sterile 10% glycerol-0.9% saline solution and returned to the body cavity. The connective tissue encompassing the linea alba, the fat and the skin may be sutured as three separate layers. An uninterrupted Halstead stitch may be used to close the lina alba. The fat and skin may be closed using a simple continuous and mattress stitch, respectively. A topical antibacterial agent (e.g. Furazolidone) may then be administered to the incision area.

Recipients may be penned in groups of about four and fed 1.8 kg of a standard 16% crude protein corn-soybean pelleted ration. Beginning on day 18 (day 0=onset of estrus), all recipients may be checked daily for signs of estrus using a mature boar. On day 35, pregnancy detection may be performed using ultrasound. On day 107 of gestation recipients may be transferred to the farrowing suite. In order to ensure attendance at farrowing time, farrowing may be induced by the administration of prostaglandin $F_{2\alpha}$ (10 mg/injection) at 0800 and 1400 hours on day 112 of gestation. In all cases, recipients may be expected to farrow within 34 hours following PGF2a administration.

Twenty-four hours after birth, all piglets may be processed, i.e. ears notched, needle teeth clipped, 1 cc of iron dextran administered, etc. A tail biopsy and blood may also be obtained from each pig.

Pigs produced according to this method are described in Example Section 6, infra, and are depicted in FIG. 2. Such pigs are healthy, do not appear to be anemic, and appear to grow at a rate comparable to that of their non-transgenic littermates. Such pigs may transmit the transgene to their offspring.

Pigs having certain characteristics may be especially useful for the production of human hemoglobin; such pigs, examples of which follow, represent preferred, non-limiting, specific embodiments of the invention.

According to one preferred specific embodiment of the invention, a transgenic pig contains at least twenty copies of a globin transgene.

According to a second preferred specific embodiment, the $P_{50}$ of whole blood of a transgenic pig according to the invention is increased by at least ten percent over the $P_{50}$ of the whole blood of a comparable non-transgenic pig, taking into consideration factors such as altitude, oxygen concentrations, pregnancy, the presence of mutant hemoglobin, etc. Thus, the present invention provides for a non-pregnant transgenic pig that carries and expresses a human globin transgene in which the $P_{50}$ of whole blood of the transgenic pig is at least ten percent greater than the $P_{50}$ of whole blood of a comparable non-pregnant non-transgenic pig at the same altitude.

In other preferred specific embodiments, the present invention provides for a transgenic pig in which the amount of human globin produced relative to total hemoglobin is at least two percent, more preferably at least five percent, and most preferably at least ten percent.

Section 6, infra, describes transgenic pigs which serve as working examples of preferred, non-limiting, specific examples of the invention.

5.3. PREPARATION OF HUMAN HEMOGLOBIN AND ITS SEPARATION FROM PIG HEMOGLOBIN

The present invention provides for a method for producing human hemoglobin comprising introducing a transgene or transgenes encoding human hemoglobin, such as a human alpha globin and a human beta globin gene, under the control of a suitable promoter or promoters, into the genetic material of a pig so as to create a transgenic pig that expresses human hemoglobin in at least some of its blood cells.

The present invention also provides for a method of producing human hemoglobin comprising (i) introducing a human alpha globin and a human beta globin gene, under the control of a suitable promoter or promoters, into the genetic material of a pig so as to create a transgenic pig that expresses human hemoglobin in at least some of its red blood cells; (ii) collecting red blood cells from the transgenic pig; (iii) releasing the contents of the collected red blood cells to form a lysate; (iv) subjecting the lysate of the red blood cells to a purification procedure that substantially separates human hemoglobin from pig hemoglobin; and (v) collecting the fractions that contain purified human hemoglobin. Such fractions may be identified by isoelectric focusing in parallel with appropriate standards. In a preferred embodiment of the invention, human hemoglobin may be separated from pig hemoglobin by DEAE anion exchange column chromatography.

In order to prepare human hemoglobin from the transgenic pigs described above, red blood cells are obtained from the pig using any method known in the art. The red blood cells are then lysed using any method, including hemolysis in a hypotonic solution such as distilled water, or using techniques as described in 1981, Methods in Enzymology Vol. 76, and/or tangential flow filtration.

For purposes of ascertaining whether human hemoglobin is being produced by a particular transgenic pig, it may be useful to perform a small-scale electrophoretic analysis of the hemolysate, such as, for example, isoelectric focusing using standard techniques.

Alternatively, or for larger scale purification, human hemoglobin may be separated from pig hemoglobin using ion exchange chromatography. Surprisingly, as discussed in Section 7, supra, human hemoglobin was observed to readily separate from pig hemoglobin using ion exchange chromatography whereas mouse hemoglobin and human hemoglobin were not separable by such methods. Any ion exchange resin known in the art or to be developed may be utilized, including, but not limited to, resins comprising diethylaminoethyl, Q-Sepharose, QCPI (I.B.F.) Zephyr, Spherodex, ectiola, carboxymethylcellulose, etc. provided that the resin results in a separation of human and pig hemoglobin comparable to that achieved using DEAE resin.

According to a specific, nonlimiting embodiment of the invention, in order to separate human from pig hemoglobin (including human/pig hemoglobin hybrids) to produce substantially pure human hemoglobin, a hemolysate of transgenic pig red blood cells, prepared as above may be applied to a DEAE anion exchange column equilibrated with 0.2 M glycine buffer at pH 7.8 and washed with 0.2 M glycine pH 7.8/5 Mm NaCl, and may then be eluted with a 5–30 Mm NaCl gradient, or its equivalent (see, for example, Section 9 infra). Surprisingly, despite about 85 percent homology between human and pig globin chains, human and pig hemoglobin separates readily upon such treatment, with human hemoglobin eluting earlier than pig hemoglobin. Elution may be monitored by optical density at 405 nm and/or electrophoresis of aliquots taken from serial fractions. Pig hemoglobin, as well as tetrameric hemoglobin composed of heterodimers formed between pig and human globin chains, may be separated from human hemoglobin by this method. Human hemoglobin produced in a transgenic pig and separated from pig hemoglobin by this method has an oxygen binding capability similar to that of native human hemoglobin.

According to another specific, non-limiting embodiment of the invention, human hemoglobin may be separated from pig hemoglobin (including human/pig hemoglobin hybrids) using QCPI ion exchange resin as follows:

About 10 mg of hemoglobin prepared from transgenic pig erythrocytes may be diluted in 20 ml of Buffer A (Buffer A=10 mM Tris, 20 mM Glycine pH 7.5). This 20 ml sample may then be loaded at a flow rate of about 5 ml/min onto a QCPI column (10 ml) which has been equilibrated with Buffer A. The column may then be washed with 2 volumes of Buffer A, and then with 20 column volumes of a 0–50 mM NaCl gradient (10 column volumes of Buffer A+10 column volumes of 10 mM Tris, 20 mM Glycine, 50 mM NaCl pH 7.5) or, alteratively, 6 column volumes of 10 mM Tris, 20 mM Glycine, 15 mM NaCl, pH 7.5, and the $O.D._{280}$ absorbing material may be collected in fractions to yield the separated hemoglobin, human hemoglobin being identified, for example, by isoelectric focusing using appropriate standards. The QCPI column may be cleaned by elution with 2 column volumes of 100 mM Tris, 20 mM Glycine, 1M NaCl, pH 7.5.

For certain mutant hemoglobins, it may be desirable to utilize a modified purification procedure. Accordingly, for the separation of Hb Presbyterian from pig Hb, a procedure as described in Example Section 12.1, infra, may be used, and for separation of Hb Yoshizuka, a procedure as described in Example Section 12.2, infra, may be used.

5.4. PREPARATION OF HUMAN/PIG HYBRID HEMOGLOBIN

The present invention also provides for essentially purified and isolated human/pig hybrid hemoglobin, in particular human $\alpha$/pig $\beta$ hybrid hemoglobin. Pig $\alpha$/human $\beta$ hybrid has not been observed to form either in vitro in reassociation experiments or in vivo in transgenic pigs.

The present invention provides for hybrid hemoglobin and its use as a blood substitute, and for a pharmaceutical composition comprising the essentially purified and isolated human/pig hemoglobin hybrid in a suitable pharmacological carrier.

Hybrid hemoglobin may be prepared from transgenic pigs, as described herein, and then purified by chromatography, immunoprecipitation, or any other method known to the skilled artisan. The use of isoelectric focusing to separate out hemoglobin hybrid is shown in FIGS. 3 and 5.

Alternatively, hybrid hemoglobin may be prepared using nucleic acid constructs that comprise both human and pig globin sequences which may then be expressed in any suitable microorganism, cell, or transgenic animal. For example, a nucleic acid construct that comprises the human $\alpha$ and pig $\beta$ globin genes under the control of a suitable promoter may be expressed to result in hybrid hemoglobin. As a specific example, human $\alpha$ globin and pig $\beta$ globin genes, under the control of cytomegalovirus promoter, may be transfected into a mammalian cell such as a COS cell, and hybrid hemoglobin may be harvested from such cells. Alternatively, such constructs may be expressed in yeast or bacteria.

It may be desirable to modify the hemoglobin hybrid so as to render it non-immunogenic, for example, by linkage with polyethylene glycol or by encapsulating the hemoglobin in a membrane, e.g. in a liposome.

6. EXAMPLE: GENERATION OF TRANSGENIC PIGS THAT PRODUCE HUMAN HEMOGLOBIN

6.1. MATERIALS AND METHODS

6.1.1. NUCLEIC ACID CONSTRUCTS

Constructs 116 (the $\alpha\alpha\beta$ construct), 185 (the $\alpha\beta$ construct), 263 (the $\alpha\rho\delta$ construct) 339, 293 and 294 were microinjected into pig ova as set forth below in order to produce transgenic pigs.

6.1.2. PRODUCTION OF TRANSGENIC PIGS

Estrus was synchronized in sexually mature gilts (>7 months of age) by feeding an orally active progestogen (allyl trenbolone, AT: 15 mg/gilt/day) for 12 to 14 days. On the last day of AT feeding all gilts received an intramuscular injection (IM) of prostaglandin $F_{2a}$ (Lutalyse: 10 mg/injection) at 0800 and 1600. Twenty-four hours after the last day of AT consumption all donor gilts received a single IM injection of pregnant mare serum gonadotropin (PMSG: 1500 IU). Human chorionic gonadotropin (HCG: 750 IU) was administered to all donors at 80 hours after PMSG.

Following AT withdrawal, donor and recipient gilts were checked twice daily for signs of estrus using a mature boar. Donors which exhibited estrus within 36 hours following HCG administration were bred at 12 and 24 hours after the onset of estrus using artificial and natural (respectively) insemination.

Between 59 and 66 hours after the administration of HCG, one- and two-cell ova were surgically recovered from bred donors using the following procedure. General anesthesia was induced by administering 0.5 mg of acepromazine/kg of bodyweight and 1.3 mg ketamine/kg of bodyweight via a peripheral ear vein. Following anesthetization, the reproductive tract was exteriorized following a mid-ventral laparotomy. A drawn glass cannula (O.D. 5 mm, length 8 cm) was inserted into the ostium of the oviduct and anchored to the infundibulum using a single silk (2-0) suture. Ova were flushed in retrograde fashion by inserting a 20 g needle into the lumen of the oviduct 2 cm anterior to the uterotubal junction. Sterile Dulbecco's phosphate buffered saline (PBS) supplemented with 0.4% bovine serum albumin (BSA) was infused into the oviduct and flushed toward the glass cannula. The medium was collected into sterile 17×100 mm polystyrene tubes. Flushings were transferred to 10×60 mm petri dishes and searched at lower power (50×) using a Wild M3 stereomicroscope. All one- and two-cell ova were washed twice in Brinster's Modified Ova Culture-3 medium (BMOC-3) supplemented with 1.5% BSA and transferred to 50 µl drops of BMOC-3 medium under oil. Ova were stored at 38° C. under a 90% $N_2$, 5% $O_2$, 5% $CO_2$ atmosphere until microinjection was performed.

One- and two-cell ova were placed in an Eppendorf tube (15 ova per tube) containing 1 ml HEPES Medium supplemented with 1.5% BSA and centrifuged for 6 minutes at 14000×g in order to visualize pronuclei in one-cell and nuclei in two-cell ova. Ova were then transferred to a 5 –10 µl drop of HEPES medium under oil on a depression slide. Microinjection was performed using a Laborlux microscope with Nomarski optics and two Leitz micromanipulators. 10–1700 copies of construct DNA (1 ng/µl of Tris-EDTA buffer) were injected into one pronuclei in one-cell ova or both nuclei in two-cell ova.

Microinjected ova were returned to microdrops of BMOC-3 medium under oil and maintained at 38° C. under a 90% $N_2$, 5% $CO_2$, 5% $O_2$ atmosphere prior to their transfer to suitable recipients. Ova were transferred within 10 hours of recovery.

Only recipients which exhibited estrus on the same day or 24 hours later than the donors were utilized for embryo transfer. Recipients were anesthetized as described earlier. Following exteriorization of one oviduct, at least 30 injected one- and/or two-cell ova and 4–6 control ova were transferred in the following manner. The tubing from a 21 g×¾ butterfly infusion set was connected to a 1 cc syringe. The ova and one to two mls of BMOC-3 medium were aspirated into the tubing. The tubing was then fed through the ostium of the oviduct until the tip reached the lower third or isthmus of the oviduct. The ova were subsequently expelled as the tubing was slowly withdrawn.

The exposed portion of the reproductive tract was bathed in a sterile 10% glycerol-0.9% saline solution and returned to the body cavity. The connective tissue encompassing the linea alba, the fat and the skin were sutured as three separate layers. An uninterrupted Halstead stitch was used to close the lina alba. The fat and skin were closed using a simple continuous and mattress stitch, respectively. A topical antibacterial agent (Furazolidone) was then administered to the incision area.

Recipients were penned in groups of four and fed 1.8 kg of a standard 16% crude protein corn-soybean pelleted ration. Beginning on day 18 (day 0=onset of estrus), all recipients were checked daily for signs of estrus using a mature boar. On day 35, pregnancy detection was performed using ultrasound. On day 107 of gestation recipients were transferred to the farrowing suite. In order to ensure attendance at farrowing time, farrowing was induced by the administration of prostaglandin $F_{2a}$ (10 mg/injection) at 0800 and 1400 hours on day 112 of gestation. In all cases, recipients farrowed within 34 hours following PGF2a administration.

Twenty-four hours after birth, all piglets were processed, i.e. ears were notched, needle teeth clipped, 1 cc of iron dextran was administered, etc. A tail biopsy and blood were also obtained from each pig.

6.2. RESULTS AND DISCUSSION

Of 3566 injected ova, thirteen transgenic pigs that expressed human hemoglobin were born, two of which died shortly after birth due to normal breeding-related incidents completely unrelated to the fact that they were transgenic pigs (Table I). The remaining 11 appeared to be healthy. A photograph of one transgenic pig is presented in FIG. 2. Profiles of the pigs and of the percent "authentic" and "hybrid" human hemoglobin ("HB") produced are set forth in Table II, infra. Total hemoglobin was calculated as the sum of human $\alpha\beta$ plus one-half of the human $\alpha$ pig $\beta$ hybrid. FIG. 3A and 3B presents the results of isoelectric focussing and triton acid urea gels of hemoglobin produced by three of these pigs (numbers 12-1, 9-3, and 6-3) which demonstrate the expression of human alpha and beta globin in these animals.

TABLE I

Efficiency of Transgenic Pig Production
Human Hemoglobin Gene Construct(s)

| Parameter | Total After 22 Trials |
| --- | --- |
| Total Ova Collected | 8276 |
| Total # Fertilized | 7156 |
| Total # Injected | 3566 |
| # Injected Ova Transferred | 3566 |
| # Control Ova Transferred | 279 |
| #Recipients Used | 104 |
| # Pigs Born (Male, Female) | 208, 332 |

TABLE I-continued

Efficiency of Transgenic Pig Production Human Hemoglobin Gene Construct(s)

| Parameter | Total After 22 Trials |
|---|---|
| # Transgenic (Male, Female) | 8, 5 (0.36)[a] |
| # Expressing | 13 |

[a]Proportion of injected ova which developed into transgenic pigs (13 transgenics/3566 injected ova).

TABLE II

FOUNDERS

| PIG | GEN-DER | TRANS-GENE CON-STRUCT | AUTH ENTIC HUMAN HB | HYBRID HB | TOTAL HUMAN HB | COPY # |
|---|---|---|---|---|---|---|
| 6-3 | F | 116 | 6.2% | 8.1% | 10.3% | 57 |
| 9-3 | F | 116 | 1.0% | 33.1% | 16.6% | 1 |
| 22-2 | M | 185 | <1% | 5.0% | 5.0% | 55 |
| 33-7 | F | 185 | *died shortly after birth | | | 0.5 |
| 38-1 | F | 185 | 1.0% | 8.3% | 5.2% | 17 |
| 38-3 | M | 185 | 4.7% | 17.2% | 13.2% | 22 |
| 38-4 | M | 185 | 3.2% | 7.0% | 6.7% | 5 |
| 47-3 | M | 263 | <1% | 2.9% | 2.0% | 4-6 |
| 47-4 | F | 263 | <1% | 18.5% | 10.0% | 1-2 |
| 52-3 | M | 263 | <1% | 7.6% | 4.0% | |
| 52-7 | M | 263 | <1% | 26.4% | 13.0% | |
| 53-11 | M | 263 | <1% | 15.5% | 8.0% | |
| 70-3 | F | 339 | 23 | 31 | 38 | 3 |

Table III presents the profiles of offspring of pig number 9-3, which shows that the F1 generation of transgenic pigs are capable of expressing hemoglobin. Of note, none of the offspring of pig number 6-3 were found to be transgenic, possibly due to the absence of transgene in the animal's reproductive tissue.

Table IV presents hemoglobin expression data of offspring of pig 38-4 carrying the "185" construct (the "αpβ" construct; see FIG. 1B). Table V presents a summary of the profiles of offspring of pig number 38-4 in which a large percentage (37.1%) of offspring were positive for expression of human hemoglobin indicating germ line transmission of the transgene. FIG. 19 presents the results of isoelectric focussing which demonstrates the levels of hemoglobin expression in representative transgene positive 38-4 offspring.

TABLE IV

EXPRESSION DATA PER LITTER FOR TRANSGENIC PIGS CARRYING THE "185" CONSTRUCT

| Founder | Litter No. | Gilt | Pigs | % Positive | #Tg | Avg. Authentic HbA |
|---|---|---|---|---|---|---|
| 38-4 | 1 | 544 | 10 | 20.0% | 2 | 8.8% |
| | 2 | 213 | 11 | 45.4% | 5 | 4.9% |
| | 3 | 882 | 5 | 20.0% | 1 | 10.9% |
| | 4 | 4923 | 6 | 83.3% | 5 | 9.4% |
| | 5 | 710 | 6 | 75.0% | 4 | 4.5% |
| | 6 | 978 | 11 | 36.4% | 4 | 7.1% |
| | 7 | 466 | 4 | 25.0% | 1 | 3.6% |
| | 8 | 464 | 15 | 33.3% | 5 | 5.1% |
| | 9 | 461 | 8 | 62.5% | 5 | 6.6% |
| | 10 | 1657 | 10 | 30.0% | 3 | 9.0% |
| | 11 | 892 | 3 | 33.3% | 1 | 5.7% |
| | 12 | 995 | 11 | 27.3% | 3 | 4.4% |
| | 13 | 209 | 11 | 36.4% | 4 | 5.4% |
| | 14 | 424 | 10 | 30.0% | 3 | 5.9% |
| | 15 | 1659 | 14 | 35.7% | 5 | 4.4% |
| | 16 | 420 | 12 | 8.3% | 1 | 2.0% |
| | 17 | 373 | 7 | 28.6% | 2 | 11.8% |
| | 18 | 497 | 8 | 62.5% | 5 | 6.0% |
| | 19 | 742 | 8 | 25.0% | 2 | 1.0% |
| | 20 | 1420 | 14 | 42.9% | 6 | 8.1% |
| | 21 | 41 | 5 | 40.0% | 2 | 1.0% |
| | 22 | 540 | 11 | 36.4% | 4 | 5.3% |
| | 23 | 7114 | 11 | 54.5% | 6 | 3.4% |
| | 24 | 744 | 11 | 27.3% | 3 | 4.9% |
| | 25 | 600 | 14 | 42.9% | 6 | 5.5% |
| | 26 | 1180 | 9 | 44.4% | 4 | 2.0% |
| | 27 | 1137 | 12 | 25.0% | 3 | 6.1% |
| | 28 | 970 | 8 | 37.5% | 3 | 10.8% |
| | 29 | 78 | 6 | 0 | 0 | |
| | 30 | 214 | 14 | 50.0% | 7 | 5.5% |
| | 31 | 279 | 6 | 50.0% | 3 | 10.3% |
| | 32 | 281 | 11 | 45.5% | 5 | 5.1% |
| | 33 | 21–474 | 6 | 33.3% | 2 | 12.3% |
| | 34 | 1151 | 10 | 30.0% | 3 | 5.3% |
| | | | 318 | | 118 | |

TABLE III

F1 (OFFSPRING) OF PIG 9-3

| PIG | GENDER | CONST. | AUTHENTIC HUMAN HB | HYBRID HUMAN HB | TOTAL HUM. | COPY # |
|---|---|---|---|---|---|---|
| 9-3-1 | F | 116 | 1.0% | 31.5% | 16.0% | 1 |
| 9-3-2* | F | 116 | 1.0% | 32.9% | 17.0% | 1 |
| 9-3-3 | M | 116 | 1.0% | 29.7% | 15.0% | 1 |
| 9-3-4 | M | 116 | 1.0% | 32.8% | 17.0% | 1 |
| 9-3-6 | F | 116 | 1.0% | 29.1% | 15.0% | 1 |
| 9-3-8 | M | 116 | 1.0% | 31.6% | 16.0% | 1 |
| 9-3-9 | M | 116 | 1.0% | 30.2% | 16.0% | 1 |

*9-3-2 died the day after birth.

TABLE V

38-4 BREEDING SUMMARY

| FOUNDER | LITTERS | PIGLETS | PIGS/LITTER | TRANSGENIC | FREQUENCY | AVG. AUTHENTIC HbA |
|---|---|---|---|---|---|---|
| 38–4(M) | 34 | 318 | 9.4 | 118 | 37.1% | 6.2% |

| MALES | AUTHENTIC HUMAN HB EXPRESSION LEVEL | FEMALES | AUTHENTIC HUMAN HB EXPRESSION LEVEL |
|---|---|---|---|
| 59 | 5.7% | 59 | 6.8% |

The birth weights of the transgenic pigs have been approximately equivalent to the birth weights of their non-transgenic littermates. As the transgenic pigs matured, their weights remained comparable to the weights of control animals.

7. EXAMPLE: SEPARATION OF HUMAN HEMOGLOBIN FROM PIG HEMOGLOBIN BY DEAE CHROMATOGRAPHY

7.1. MATERIALS AND METHODS
7.1.1. PURIFICATION BY DEAE CHROMATOGRAPHY

For purification, red blood cells were collected by centrifugation of 5000 rpm for 3 minutes in an eppendorf microcentrifuge and washed three times with an equal volume (original blood) of 0.9% NaCl. Red cells were lysed with 1.5 volumes deionized $H_2O$, centrifuged at 15,000 rpm, and the supernatant was fractionated by anion exchange chromatography. DEAE cellulose chromatography (DE-SE manufactured by Whatman, Ltd.) was performed according to W. A. Schroeder and T. H. J. Huisman "The Chromatography of Hemoglobin", Dekker, New York, pp. 74–77. The 0.25 ml red cell hemolysate described above was applied to 1 cm×7 cm DE-52 column pre-equilibrated in 0.2M glycine Ph 7.8 and was washed with 5 column volumes of 0.2M glycine Ph 7.8/5 Mm NaCl. Hemoglobins were eluted with a 200 ml 5–30 mM NaCl/0.2M glycine pH 7.8 gradient. To complete elution of pig-hemoglobin, an additional 50 to 100 ml of 30 mM CaCl/glycine pH 7.8 was added to the column. Elution of hemoglobin was monitored by absorbance of 415 mM and by IEF analysis of column fractions.

7.1.2. REASSOCIATION OF GLOBIN CHAINS

Reassociation of globin chains was performed essentially as described in Methods in Enzymol. 76:126–133. 25 lambda of pig blood, 25 lambda of human blood,or a 25 lambda mixture of 12.5 lambda human blood and 12.5 lambda pig blood were treated as follows. The blood was pelleted at a setting of 5 on microfuge for 2 minutes, then washed three times with 100 lambda 0.9 percent NaCl. The cells were lysed with 50 lambda $H_2O$, then spun at high speed to confirm lysis. 50 lambda of the lysed cells was then combined with 50 lambda 0.2M Na Acetate, pH 4.5, put on ice and then incubated in a cold room overnight. After adding 1.9 ml 0.1M $NaH_2PO_4$4, pH 7.4 each sample was spun in centricon tubes at 4° C. and 5K until about 0.5 ml remained. Then 1 ml of 0.1M $NaH_2PO_4$ pH 7.4 was added and spun through at about 5K until about 0.2 ml volume was left. The hemoglobin was then washed from the walls of the centricon tube, an eppendorf adaptor was attached, and a table top microfuge was used to remove each sample from its centricon tube. The samples were then analyzed by isoelectric focusing.

7.2. RESULTS AND DISCUSSION
7.2.1. HUMAN AND PIG HEMOGLOBIN WERE SEPARATED FROM A HEMOLYZED MIXTURE OF HUMAN AND PIG BLOOD

Equal proportions of human and of pig blood were mixed and lysed, and the resulting hemolysate was subjected to DEAE chromatography as described supra.

As shown in FIG. 4A, pig hemoglobin separated virtually completely from human hemoglobin. This complete separation is surprising in light of the structural similarity between human and pig hemoglobin; pig and human alpha globin chains are 84.4 percent homologous and pig and human beta globin chains are 84.9 percent homologous. It is further surprising because, as shown in FIG. 4C, when human and mouse blood was mixed, hemolyzed, applied to and eluted from a DEAE column according to methods set forth in Section 7.1.1., supra, human and mouse hemoglobin were not observed to separate despite the fact that mouse and human alpha globin chains are about 85.8 percent homologous and mouse and human beta globin chains are 80.1 percent homologous. The ease of separation of human and pig hemoglobin on DEAE resin appears to be both efficient and economical.

Interestingly, the order of elution of the proteins from the anion exchange column was not as expected. Based on the relative pI's of the proteins as deduced from the IEF gels, the predicted order of elution would be first the hybrid (human α/pig β) followed by the authentic human α/human β. The last protein to elute from the anion exchange column then would be the endogenous pig α/pig β protein. However, under all the conditions currently attempted the order of elution was altered such that the human hemoglobin was the first to elute. The second peak was an enriched fraction of the hybrid followed very closely by the pig hemoglobin.

7.2.2. HUMAN AND PIG HEMOGLOBIN AND HUMAN/PIG HETEROLOGOUS HEMOGLOBIN WERE SEPARATED FROM HEMOLYSATE PREPARED FROM A TRANSGENIC PIG

Blood from transgenic pig 6-3 (as described in Section 6, supra) was lysed by hypotonic swelling and the resulting hemolysate was subjected to DEAE chromatography as described supra. As shown in FIG. 4B, human hemoglobin was separated from pig hemoglobin and from human α globin/pig beta globin heterologous hemoglobin. As shown in FIG. 4D, human hemoglobin was substantially purified by this method.

7.2.3. PIG ALPHA GLOBIN/HUMAN BETA GLOBIN HETEROLOGOUS HEMOGLOBIN DOES NOT APPEAR TO FORM BASED ON REASSOCIATION DATA

Heterologous association between pig alpha globin and human beta globin chains has not been detected in hemolysates obtained from human hemoglobin-expressing transgenic pigs. It was possible, however, that this observation could be explained by relatively low levels of human beta globin expression. Alternatively, association between pig alpha globin and human beta globin may be chemically unfavorable. In order to explore this possibility, reassociation experiments were performed in which pig and human hemoglobin were mixed, dissociated, and then the globin chains were allowed to reassociate. As shown in the isoelectric focusing gels depicted in FIG. 5, although pig α/pig β, human α/human β, and human α/pig β association was observed, no association between pig α globin and human β globin appeared to have occurred. Therefore the pig α/human β heterologous hemoglobin should not be expected to complicate the purification of human hemoglobin from transgenic pigs.

8. EXAMPLE: SEPARATION OF HUMAN HEMOGLOBIN FROM PIG HEMOGLOBIN BY OCPI CHROMATOGRAPHY

8.1. MATERIALS AND METHODS

Clarified hemolysate from transgenic pig 6-3 13 mg/ml; Buffer A: 10 mM Tris, 20 mM Glycine pH 7.5; Buffer B: 10 mM Tris, 20 mM Glycine, 15 mM NaCl pH 7.5; Buffer C: 10 mM Tris, 20 mM Glycine, 1M NaCl pH 7.5; Buffer D: 10 mM Tris, 20 mM Glycine, 50 mM NaCl pH 7.5; QCPI column 10ml Equilibrated in Buffer A; Trio purification system. 10 mg of hemoglobin prepared from transgenic pig 6-3 was diluted in 20 ml Buffer A. 20 ml of sample was loaded at a flow rate of 5 ml/min onto the QCPI column, and washed with 2 column volumes of Buffer A. The column was then washed with 20 column volumes of a 0–50 mM NaCl gradient. (10 column volumes Buffer A+10 column volumes of Buffer D) and the O.D.$_{280}$ absorbing material was collected. The column was then cleaned with 2 column volumes of Buffer C, and then re-equilibrated with 2 column volumes of Buffer A.

8.2. RESULTS

Analysis of the UV trace (peak vs. volume of gradient) (FIG. 6) revealed that the human hemoglobin was eluted at 15 mM NaCl. Subsequent purifications have been performed utilizing the same protocol as above, only using 6 column volumes of Buffer B (15 mM NaCl) to elute the human hemoglobin rather than the gradient. In addition, non-transgenic pig chromatographed by this method does not elute from the QCPI with Buffer B, while native human hemoglobin does. The protein that eluted at 15 mM NaCl was analyzed on the Resolve isoelectric focussing system and found to be essentially pure of contaminating pig hemoglobin or hybrid hemoglobin.

9. EXAMPLE: HUMAN ALPHA/PIG BETA GLOBIN

HYBRID HEMOGLOBIN EXHIBIT INCREASED P$_{50}$As shown in Tables II and III, supra, transgenic pigs of the invention were all found to produce significant amounts of human α/pig β globin hybrid hemoglobin (the pig α/human β hybrid was not observed). Significantly, pigs that expressed higher percentages of hybrid also appeared to exhibit elevated P$_{50}$ values for their whole blood (FIG. 7).

10. EXAMPLE: ENHANCED EXPRESSION USING PIG BETA GLOBIN REGULATORY SEQUENCES

The 339 construct (FIGS. 1R and 12) containing the pig adult beta globin gene promoter region (FIG. 8), was used to prepare transgenic pigs according to the method set forth in Section 6.1.2. supra. FIG. 15 depicts an isoelectric focusing gel analysis of hemoglobin produced by pig 70-3; equal amounts of hemoglobin from transgenic pig 6-3, carrying the 116 construct (FIG. 1A) and human hemoglobin are run in adjacent lanes for comparison. As indicated by the brighter bands observed in the lane containing pig 70-3 hemoglobin at positions corresponding to human and hybrid hemoglobins (relative to the lane containing pig 6-3 hemoglobin), the amount of human hemoglobin produced by pig 70-3 is greater than the amount produced by pig 6-3. It has been calculated that 38 percent of the total hemoglobin produced by pig 70-3 is human hemoglobin, whereas 10 percent of total hemoglobin produced by pig 6-3 is human hemoglobin (see Table II and Section 6.2. supra, for data and calculations). This suggests that the pig beta globin promoter region is more efficient than the human beta globin promoter in transgenic pigs.

In a separate series of experiments, two more transgenic pigs, expressing human hemoglobin, were obtained using construct "339" (pigs 80-4 and 81-3) (FIG.17). Human hemoglobin levels in these transgenic pigs was determined by running isoelectric focussing gels and densitometric scanning of the individual bands (FIG. 18). As indicated in FIG. 17, both pig 70-3 and pig 80-4 expressed high levels of authentic human hemoglobin. To obtain the copy number of transgenes, genomic DNA (isolated from the tail) was digested with EcoR I and a Southern Blot was performed. The probe used was a 427 bp NcoI/Bam HI fragment of human beta globin gene containing the first exon, first intron and part of the second exon.

11. EXAMPLE: MOLECULAR MODELING OF PIG HEMOGLOBIN AND THE α$_1$β$_1$ INTERFACE OF A HYBRID BETWEEN PIG β AND HUMAN α GLOBIN

It has been found that the amount of hybrid human α/pig β hemoglobin often exceeds the amount of human hemoglobin. The molecular basis of this observation has been investigated using molecular modeling and molecular biology. The model structure of the hybrid molecule is based on the known structures of human hemoglobins and the structural homology between the human and pig structures (A. M. Lesk, 1991, Protein Architecture: A Practical Approach, Oxford University Press, N.Y.). The pig and hybrid hemoglobin structures were modeled using the following four steps: (1) hydrogen atoms were added to the X-ray model and their positions modified using energy minimization; (2) amino acid residue replacements were introduced to model the target pig and hybrid structures (no chain alignment was necessary); (3) the side chain positions of these modified residues were energy minimized; and (4) the result was visually examined and found to be sound. The modeled structures are shown in FIG. 20.

Detailed examination of all the relevant contacts indicated striking differences at several residues. For example, at position β112 the human hemoglobin has a cysteine residue but the hybrid has a valine residue. The valine is in apparent closer contact (arrow in FIG. 20) with the opposing subunit, and thus may be more effective in stabilizing the α$_1$β$_1$ interface (FIG. 21).

The effect of amino acid substitutions at the α$_1$β$_1$ interface on the hydrophobic and polar interactions as predicted by HINT are shown in TABLE VI. HINT is software from Virginia Commonwealth University Licensed from Medical College of Virginia, Richmond, Virginia that can analyze the positive and negative scores as determined by attractive and repulsive interactions known from experimental physical chemistry measurements. TABLE VI represents the differences between the unmodified dimer and the one with the specified replacement. TABLE VII has the same format as TABLE VI with the following two exceptions: (1) as each replacement is added, the previous one(s) are kept, and (2) the reported difference is a comparison between the current dimer and the one reflected in the preceding row. As the subsequential changes are made, the predicted attractive forces at the interface increase. If each column is summed up the total difference between the unmodified dimer and the one with seven changes is obtained. The sums are +1340 for hydrophobic and +660 for polar.

TABLE VI

Effect of amino acid replacements at the α1β1 interface

| | | | Predicted Difference | |
|---|---|---|---|---|
| Chain | Residue | Replacement | Hydrophobic | Polar |
| α | 30 | E to T | +250 | +10 |
| α | 36 | F to Y | −110 | +220 |
| α | 106 | L to F | +20 | +10 |
| α | 107 | V to S | −10 | +120 |
| α | 107 | V to C | 0 | +150 |
| α | 111 | A to C | +30 | +100 |
| β | 33 | V to L | +70 | 0 |
| β | 112 | C to V | +330 | −60 |
| β | 112 | C to I | +360 | −50 |
| β | 115 | A to V | +80 | +10 |
| β | 115 | A to L | +90 | +10 |
| β | 119 | G to H | +250 | +120 |
| β | 125 | P to M | +80 | 0 |
| β | 128 | A to I | +80 | 0 |
| β | 131 | Q to E | +120 | +110 |

TABLE VII

Effect of combinations of amino acid replacements at the α1β1 interface on the hydrophobic and polar interactions

| | | | Predicted Difference | |
|---|---|---|---|---|
| Chain | Residue | Replacement | Hydrophobic | Polar |
| β | 112 | C to I | +360 | −50 |
| α | 110 | A to I | +200 | +10 |
| β | 115 | A to V | +150 | +10 |
| β | 119 | G to H | +270 | +130 |
| α | 36 | F to Y | −130 | +240 |
| β | 33 | V to L | +80 | +0 |
| α | 30 | E to T | +260 | +10 |
| β | 131 | Q to E | +150 | +310 |

12. EXAMPLE: EXPRESSION OF GENETICALLY MODIFIED HEMOGLOBINS IN TRANSGENIC ANIMALS

Of the known human hemoglobin variants, about two dozen exhibit a lower oxygen affinity, which could be advantageous in clinical applications. While many of these mutants result in unstable hemoglobin molecules, several variants have desirable biochemical properties and can be used for the generation of blood substitutes using recombinant DNA technology. Transgenic pigs expressing two of these variants, Hb Presbyterian (108 Asn→Lys, FIG. 1G) and Hb Yoshizuka (108 Asn→Asp, FIG. 1F) have been produced and purification and characterization of the expressed human globins is described below.

12.1. PURIFICATION AND CHARACTERIZATION OF Hb PRESBYTERIAN

The amino acid substitution generated in Hb Presbyterian (108 Asn→Lys) results in the comigration of Hb Presbyterian with the hybrid (hαpβ) hemoglobin on isoelectric focussing gels. Based on previous results with the purification of human hemoglobin from hybrid and porcine hemoglobins and the more positive nature of the Hb Presbyterian it should be easier to purify this variant hemoglobin on an anion exchange resin. Approximately 500 ml of blood was obtained from the transgenic pig 57-10. The blood was washed several times with isotonic saline and then lysed by hypotonic swelling in water. The cell membranes were removed by centrifugation at 10000×g to yield a final hemoglobin concentration of about 100 mg/ml. Hb Presbyterian was purified from the hybrid and porcine hemoglobins as follows: 1–2.5 g of hemolysate was loaded onto an XK 50/30 column packed with 450 ml of Biorad Macroprep High Q resin equilibrated with 10 mM Tris-Cl and 20 mM Glycine at pH 8.1 (Buffer A). The proteins were eluted at a flow rate of 10 ml/min with a linear salt gradient of 9–16% Buffer B (Buffer A containing 250 mM NaCl) over 3000 ml.

The initial peak was thought to be Hb Presbyterian followed by the co-elution of the hybrid and porcine hemoglobins (FIG. 20). To confirm the identity of the first peak as Hb Presbyterian and not the hybrid hemoglobin, a sample of the protein was run on Reversed Phase HPLC (FIG. 21). The initial peak from the anion exchange column was Hb Presbyterian with the α-chains eluting at the same time as normal human α-chains and the β-chains eluting slightly faster than normal human β-chains. This was also found to be an excellent way of determining if porcine hemoglobin was contaminating the column fractions. Using this purification procedure and the analysis on HPLC the recombinant Hb Presbyterian derived from the transgenic pig 58-10 was judged to be greater than 95% pure.

Purified Hb Presbyterian was dialyzed against 50 mM HEPES and 100 mM NaCl at pH 7.4 and oxygen equilibrium curves determined using a Hemox Analyzer (TCS Products, Southampton, Pa.). The Hemox Analyzer was modified to allow analog to digital data conversion for ease of oxygen binding calculations. Under these conditions the Hb Presbyterian had a $P_{50}$ of 25.8 mmHg (Hill Coefficient n=2.3) versus 13.3 mm Hg (n=2.9) for Hb A indicating that the Hb Presbyterian bound oxygen with lower affinity than native Hb. Preliminary results to determine the Bohr Effect (Influence of pH on the oxygen affinity) indicated a normal Bohr effect for Hb Presbyterian (FIG. 22).

12.2. PURIFICATION AND CHARACTERIZATION OF Hb YOSHIZUKA

Blood samples taken from the transgenic pigs expressing Hb Yoshizuka (68-3 and 68-2) were treated essentially the same as described above. The final concentration of the hemolysate was approximately 100 mg/ml. The purification of the protein required a slightly different strategy, however. A sample of hemolysate from 68-3 (about 10 mg) was loaded onto an HR 10/30 Biorad Macroprep High Q resin column equilibrated with 10 mM Tris-Cl and 20 mM Glycine at pH 8.7 (Buffer A). The hemoglobins were eluted at 2.5 mls/min with a 5–30% linear gradient of Buffer B (Buffer A plus 250 mM NaCl) over 500 ml (FIG. 23). Fractions were collected and analyzed by IEF to assess purity which was determined to be about 75% or better.

13. EXAMPLE: CLONING OF PORCINE β GLOBIN LOCUS CONTROL REGIONS (LCR)

The porcine β Locus Control Region (LCR) was cloned and sequenced. Constructs comprising the human globin genes under the control of the porcine LCR may be used to generate transgenic pigs with enhanced hemoglobin expression.

A porcine genomic library in EMBL-3 (Clonetech, Calif.) was plated and 2 million plaques were screened. A 3 kb Sal I to Eco RI fragment (extending from −1.9 kb to −4.9 kb with respect to porcine ξ gene) derived from the 12 Kb SALI fragment of ξ gene was used as a probe. Two positive clones (Phage L and Phage H) were isolated.

Southern analysis of restricted Phage L and Phage H suggested that the two clones overlapped (FIG. 26A). The 7 kb and 4 kb SSt1 fragments of Phage H were subcloned into plasmid pGem3 to obtain plasmids pPH2 and pPH1, respectively (deposited with the ATCC and assigned accession numbers 75519 for pPH2 and 75519 for pPH1). These plasmids were sequenced (from Sp6 and T7 promoter) and the sequence was compared with the human genomic sequences. All the matches were with the sequence of the human beta globin region located on chromosome 11, which contains the entire beta globin locus. Further sequencing was carried out for PH1 using additional primers. Sequence analysis revealed that the 3' end of clone PH1 (PH1-TA1, FIG. 27A) was 69% homologous to human LCRI (FIG. 27B). The sequence of the 5' end of PH1 and 3' end of PH2 were joined (joined plcr2, FIG. 28) and found to be similar to human LCRII (FIG. 29). The 5' end of PH2 (PH2-T7, FIG. 30A) had a stretch of 38 bp which was 78.9% homologous to a sequence in human LCRIV (FIG. 30B).

14. EXAMPLE: OPTIMIZATION OF HUMAN β GLOBIN GENE

Analysis of blood samples from transgenic pigs carrying human hemoglobin genes indicates that human α-globin is expressed at higher levels than human beta globin. The overall production of human hemoglobin tetramers in transgenic animals may be increased by optimizing the expression of human β-globin gene expression. Such optimization may improve expression of β-globin by affecting mRNA structure, stability or rate of translation.

One approach to increasing the level of expressed β-globin is to engineer the human β-globin gene, from the promoter region through the coding sequence and into the polyadenylation site and 3' untranslated region, to be similar to the pig β-globin gene, but without altering the amino acid sequence from that of the authentic wild-type human β-globin.

Using polymerase chain reactions, synthetic oligonucleotides and restriction digests, constructs were genetically engineered to optimize the human β-globin gene for porcine expression. As shown in FIG. 31, the promoter region, intervening sequences I and II (IVSI and IVSII), as well as poly A and 3' UTR region are pig sequences and were obtained by restriction digests from pig β-globin gene. Exon 1, Exon 2 and Exon 3 were generated either by polymerase chain reaction or by oligonucleotide synthesis (exon 2 SfaN1 through Bam HI, and all of exon 3).

A comparison of coding sequences of optimized, human and pig sequences is diagrammed in FIG. 32. Lines in the optimized sequence indicates nucleic acid changes from the human sequence.

Table VIII shows the number of changes between human, optimized and pig coding sequences. The Table is subdivided into the 3 Exons and shows changes at the nucleotide, codon and amino acid level.

TABLE VIII

Optimization of β Globin Codons

Number of Changes

| | Exon 1 | | Exon 2 | | Exon 3 | |
|---|---|---|---|---|---|---|
| | H→H* | H→P | H→H* | H→P | H→H* | H→P |
| Nucleotides | 5 | 14 | 18 | 31 | 8 | 24 |
| Codons | 5 | 10 | 18 | 25 | 8 | 18 |
| Amino acids | 0 | 5 | 0 | 7 | 0 | 10 |

H* = Optimized human β globin gene

Comparisons between the human and pig β-globin coding sequences are depicted in FIG. 35. Differences are signified by small letters in the pig (bottom) sequence and codons containing nucleotide changes are underlined. Comparisons of human and optimized β-globin coding sequences and optimized and pig β-globin coding sequences are shown in FIGS. 36 and 37, respectively. The coding sequence and amino acid sequence of optimized β-globin gene are indicated in FIG. 38. A plasmid containing the optimized β-globin gene, designated pGEM3B*Δ3', has been deposited with the ATCC and assigned accession number 75518

A number of constructs were engineered to express the optimized β-globin gene. Construct 505 (FIG. 33) contains the human locus control region, the human α-globin gene driven by its own promoter, the human ξ-globin gene also driven by its own promoter, and the optimized β-globin gene which has the optimized coding region. The gene order in this construct is LCRαξβ (where * signifies optimized β gene). A second construct, designated Construct 515 (FIG. 34), contains the human locus control region, the human α-globin gene driven by its own promoter, the human ξ-globin gene also driven by its own promoter and the optimized β-globin gene which includes the porcine introns, poly A and 3' UTR driven by the porcine promoter. The gene order in this construct is LCR ξβ*αα (where * signifies optimized β gene). Constructs 505 or 515 may be used to generate transgenic pigs expressing human hemoglobin.

15. DEPOSIT OF MICROORGANISMS

The following plasmids were deposited with the American Type Culture Collection (ATCC), 12301 Parklawn Drive, Rockville, Md. 20852.

| plasmid | containing | accession no. |
|---|---|---|
| psaf/pigε(k) | pigε globin gene | 75371 |
| pGem5/Pigβpr(K) | pig adult β globin gene regulatory region | 753727 |
| pPig3'β | 3' end of pig β globin gene | 75373 |
| pGEM3 β* Δ3' | optimized human β globin | 75520 |
| pPH1 | pig β globin LCR | 75518 |
| pPH2 | pig β globin LCR | 75519 |

Various publications are cited herein which are hereby incorporated by reference in their entirety.

What is claimed is:

1. A purified and isolated nucleic acid comprising: the pig adult β globin regulatory region as contained in a plasmid pGem5/Pigβpr(K), as deposited with the American Type Culture Collection and assigned accession number 75371.

2. A purified and isolated nucleic acid comprising: the pig ε globin gene as contained in plasmid pSaf/pigε(K), as deposited with the American Type Culture Collection and assigned accession number 75373.

3. A purified and isolated nucleic acid comprising: the 3' region of the pig adult β globin gene as contained in plasmid pPig3'β, as deposited with the American Type Culture Collection and assigned accession number 75372.

4. A purified and isolated nucleic acid comprising the pig β-globin LCR, as contained in plasmid pPH1, as deposited with the American Type Culture Collection and assigned accession number 75518.

5. A purified and isolated nucleic acid comprising the pig β-globin LCR, as contained in plasmid pPH2, as deposited with the American Type Culture Collection and assigned accession number 75519.

6. A purified and isolated nucleic acid comprising an optimized human β-globin gene as contained in plasmid pGEM3 β* Δ3', as deposited with the American Type Culture Collection and assigned accession number 75520.

7. A method of purifying human hemoglobin from a mixture of human hemoglobin, pig hemoglobin, and human/pig hybrid hemoglobin, comprising:
   (i) collecting red blood cells from a transgenic pig comprised of the DNA sequences for human alpha globin and human beta globin operably linked to promoter elements where human hemoglobin is produced in at least some of the red cells of said pig;
   (ii) releasing the contents of the collected red blood cells to produce a lysate;
   (iii) applying the lysate of step (ii) to DEAE-Cellulose anion exchange column equilibrated to a pH of about 7.8;
   (iv) eluting the column with a salt gradient of 5 mM–30 mM NaCl; and
   (v) collecting the fractions that contain purified human hemoglobin.

8. A method of purifying human hemoglobin from a mixture of human hemoglobin, pig hemoglobin, and human/pig hybrid hemoglobin, comprising:
   (i) collecting red blood cells from a transgenic pig comprised of the DNA sequences for human alpha globin and human beta globin operably linked to promoter elements where human hemoglobin is produced in at least some of the red cells of said pig;
   (ii) releasing the contents of the collected red blood cells to produce a lysate;
   (iii) applying the lysate of step (ii) to an anion exchange column equilibrated to a pH of about 7.8;
   (iv) eluting the column with a salt gradient; and
   (v) collecting the fractions that contain purified human hemoglobin.

9. A method for purifying human Presbyterian Hemoglobin from a mixture of human hemoglobin, pig hemoglobin, and human/pig hybrid hemoglobin comprising;
   (i) collecting red blood cells from a transgenic pig to producing human Presbyterian hemoglobin in at least some its red cells;
   (ii) releasing the contents of the collected red blood cells to produce a lysate;
   (iii) applying the lysate of step (ii) to a High Q resin column equilibrated with 20 mM Tris-C1 and 20 mM Glycine at a pH 8.1;
   (iv) eluting the column with a linear salt gradient of 9–16% in buffer containing 10 mM Tris-C1, 20 mM Glycine, 250 mM NaCl at pH 8.1; and
   (v) collecting the fractions that contain purified human Presbyterian Hb.

10. A method for purifying human Yoshizuka Hemoglobin from a mixture of human hemoglobin, pig hemoglobin, and human/pig hybrid hemoglobin, comprising:
   (i) collecting red blood cells from a transgenic pig producing human Yoshizuka hemoglobin in at least some its red cells;
   (ii) releasing the contents of the collected red blood cells to produce a lysate;
   (iii) applying the lysate of step (ii) to a High Q resin column equilibrated with 10 mM Tris-C1 and 20 mM Glycine at a pH 8.7;
   (iv) eluting the column with a linear containing 10 mM Tris-C1, 20 mM Glycine, 250 mM NaCl at pH 8.7; and
   (v) collecting the fractions that contain purified human Presbyterian Hb.

* * * * *